ial) United States Patent  
Widmer et al.

(10) Patent No.: US 9,726,518 B2
(45) Date of Patent: Aug. 8, 2017

(54) SYSTEMS, METHODS, AND APPARATUS FOR DETECTION OF METAL OBJECTS IN A PREDETERMINED SPACE

(71) Applicant: QUALCOMM Incorporated, San Diego, CA (US)

(72) Inventors: Hanspeter Widmer, Wohlenschwil (CH); Markus Bittner, Sarmenstorf (CH); Lukas Sieber, Olten (CH); Marcel Fischer, Boniswil (CH)

(73) Assignee: QUALCOMM Incorporated, San Diego, CA (US)

( * ) Notice: Subject to any disclaimer, the term of this patent is extended or adjusted under 35 U.S.C. 154(b) by 542 days.

(21) Appl. No.: 13/791,585

(22) Filed: Mar. 8, 2013

(65) Prior Publication Data
US 2014/0015329 A1 Jan. 16, 2014

Related U.S. Application Data

(60) Provisional application No. 61/671,498, filed on Jul. 13, 2012.

(51) Int. Cl.
*H01F 38/14* (2006.01)
*G01D 5/20* (2006.01)
(Continued)

(52) U.S. Cl.
CPC ............ *G01D 5/2006* (2013.01); *B60L 3/003* (2013.01); *B60L 3/0038* (2013.01); *B60L 3/0046* (2013.01);
(Continued)

(58) Field of Classification Search
CPC ......... G01V 3/10; H04B 5/0037; B60L 11/14; B60L 11/182; B60L 11/1824;
(Continued)

(56) References Cited

U.S. PATENT DOCUMENTS 4,027,303 A 5/1977 Neuwirth et al.
4,527,153 A 7/1985 Suzuki et al.
(Continued)

FOREIGN PATENT DOCUMENTS

CN 101232311 A 7/2008
CN 201580217 U 9/2010
(Continued)

OTHER PUBLICATIONS

Conductix-Wampfler AG, Abschlussbericht zum Verbundvorhaben "Kabelloses Laden von Elektrofahrzeugen", im Rahmen des FuE-Programms "Förderung von Forschung and Entwicklung im Bereich der Elektromobilität", Weil am Rhein, Oct. 2011, with Machine Translation of Executive Summary.
(Continued)

*Primary Examiner* — Rexford Barnie
*Assistant Examiner* — Terrence Willoughby
(74) *Attorney, Agent, or Firm* — Knobbe, Martens, Olson & Bear, LLP

(57) ABSTRACT

This disclosure provides systems, methods and apparatus for detecting foreign objects. In one aspect an apparatus for detecting a presence of an object is provided. The apparatus includes a resonant circuit having a resonant frequency. The resonant circuit includes a sense circuit including an electrically conductive structure. The apparatus further includes a coupling circuit coupled to the sense circuit. The apparatus further includes a detection circuit coupled to the sense circuit via the coupling circuit. The detection circuit is configured to detect the presence of the object in response to detecting a difference between a measured characteristic that depends on a frequency at which the resonant circuit is resonating and a corresponding characteristic that depends on the resonant frequency of the resonant circuit. The coupling circuit is configured to reduce a variation of the
(Continued)

resonant frequency by the detection circuit in the absence of the object.

39 Claims, 32 Drawing Sheets

(51) Int. Cl.
*G01N 27/72* (2006.01)
*B60L 3/00* (2006.01)
*B60L 3/04* (2006.01)
*B60L 11/14* (2006.01)
*B60L 11/18* (2006.01)
*H02J 50/12* (2016.01)
*H02J 50/60* (2016.01)
*H04B 5/00* (2006.01)
*G01V 3/10* (2006.01)

(52) U.S. Cl.
CPC ............... *B60L 3/04* (2013.01); *B60L 11/14* (2013.01); *B60L 11/182* (2013.01); *B60L 11/1803* (2013.01); *B60L 11/1824* (2013.01); *B60L 11/1833* (2013.01); *B60L 11/1835* (2013.01); *B60L 11/1842* (2013.01); *B60L 11/1844* (2013.01); *B60L 11/1846* (2013.01); *B60L 11/1877* (2013.01); *G01N 27/725* (2013.01); *H01F 38/14* (2013.01); *H02J 50/12* (2016.02); *H02J 50/60* (2016.02); *H04B 5/0043* (2013.01); *B60L 2200/12* (2013.01); *B60L 2200/22* (2013.01); *B60L 2210/30* (2013.01); *B60L 2210/40* (2013.01); *B60L 2230/16* (2013.01); *B60L 2240/36* (2013.01); *B60L 2240/525* (2013.01); *B60L 2250/16* (2013.01); *B60L 2270/147* (2013.01); *B60L 2270/32* (2013.01); *B60L 2270/34* (2013.01); *G01V 3/10* (2013.01); *H04B 5/0037* (2013.01); *Y02E 60/721* (2013.01); *Y02T 10/70* (2013.01); *Y02T 10/7005* (2013.01); *Y02T 10/705* (2013.01); *Y02T 10/7077* (2013.01); *Y02T 10/7088* (2013.01); *Y02T 10/7241* (2013.01); *Y02T 90/121* (2013.01); *Y02T 90/122* (2013.01); *Y02T 90/125* (2013.01); *Y02T 90/127* (2013.01); *Y02T 90/128* (2013.01); *Y02T 90/14* (2013.01); *Y02T 90/163* (2013.01); *Y02T 90/169* (2013.01); *Y04S 10/126* (2013.01); *Y04S 30/14* (2013.01)

(58) Field of Classification Search
CPC .............. B60L 11/1833; B60L 11/1842; B60L 11/1844; B60L 11/1846; B60L 11/1803
See application file for complete search history.

(56) References Cited

U.S. PATENT DOCUMENTS

| | | | | |
|---|---|---|---|---|
| 4,754,862 A * | 7/1988 | Rawicz-Szczerbo | .... | G07D 5/08 194/317 |
| 5,287,111 A | 2/1994 | Shpater | | |
| 5,892,300 A | 4/1999 | Rydval | | |
| 6,216,540 B1 | 4/2001 | Nelson et al. | | |
| 6,914,552 B1 | 7/2005 | McEwan | | |
| 7,068,028 B2 | 6/2006 | Reining | | |
| 7,095,221 B2 | 8/2006 | Bosselmann et al. | | |
| 7,772,838 B2 | 8/2010 | Bailey et al. | | |
| 8,264,401 B1 | 9/2012 | Kavaler | | |
| 2002/0013526 A1 | 1/2002 | Su et al. | | |
| 2006/0133633 A1 | 6/2006 | Hyvonen et al. | | |
| 2010/0244580 A1* | 9/2010 | Uchida et al. | ................ | 307/104 |
| 2011/0128015 A1 | 6/2011 | Dorairaj et al. | | |
| 2012/0077537 A1 | 3/2012 | Muratov et al. | | |
| 2012/0112538 A1 | 5/2012 | Kesler et al. | | |
| 2012/0119576 A1 | 5/2012 | Kesler et al. | | |
| 2012/0146580 A1 | 6/2012 | Kitamura | | |
| 2012/0187757 A1 | 7/2012 | Wechlin et al. | | |
| 2014/0015522 A1 | 1/2014 | Widmer et al. | | |

FOREIGN PATENT DOCUMENTS

| | | |
|---|---|---|
| CN | 101917040 A | 12/2010 |
| CN | 102165669 A | 8/2011 |
| CN | 102457106 A | 5/2012 |
| CN | 102548789 A | 7/2012 |
| CN | 103069689 A | 4/2013 |
| EP | 0029673 A1 | 6/1981 |
| EP | 0541392 A1 | 5/1993 |
| EP | 0541392 B1 | 2/1996 |
| EP | 0816870 A2 | 1/1998 |
| JP | 2012016125 A | 1/2012 |
| TW | 201215005 A | 4/2012 |
| WO | 2011006758 A2 | 1/2011 |
| WO | 2011006876 A2 | 1/2011 |
| WO | WO-2012002063 A1 | 1/2012 |

OTHER PUBLICATIONS

IEC 60364-4-42 (May 2010) "Low-voltage electrical installations—Part 4-42: Protection for safety—Protection against thermal effects", Abstract.
Kuyvenhoven et al., "Development of a Foreign Object Detection and Analysis Method for Wireless Power Systems," 2011 IEEE Symposium on Product Compliance Engineering (PSES), pp. 1-6.
Li et al., "A microwave measurement system for metallic object detection using swept-frequency radar", Millimetre Wave and Terahertz Sensors and Technology, Proc. of SPIE vol. 7117 71170K-1, 2008.
Ringbeck et al., "A 3D time of flight camera for object detection", Optical 3-D Measurement Techniques, ETH Zürich, Plenary Session 1: Range Imaging I, Jul. 9-12, 2007.
VDE-AR-E 2122-4-2 Anwendungsregel:2011-03 Elektrische AusrUstung von Elektro-Straflenfahrzeugen—Induktive Ladung von Elektrofahrzeugen—Teil 4-2: Niedriger Leistungsbereich, Mar. 2011, with English Abstract only.
Wikipedia, "Metal detector," retrieved from http://en.wikipedia.org/wiki/Metal_detector on Jul. 12, 2012.
Wikipedia, "RANSAC," retrieved from http://en.wikipedia.org/wiki/RANSAC on Jul. 12, 2012.
International Search Report and Written Opinion—PCT/US2013/049935—ISA/EPO—Feb. 10, 2014.
Partial International Search Report—PCT/US2013/049935—ISA/EPO—Oct. 24, 2013.
Taiwan Search Report—TW102125283—TIPO—Oct. 6, 2015.
Taiwan Search Report—TW104123934—TIPO—Apr. 14, 2016.
Wei H-B., et al., "Technical Analysis of Wireless Power Transmission in the Electric Power System", Journal of Southwest University, Sep. 20, 2009, vol. 31, No. 9, pp. 163-167.

* cited by examiner

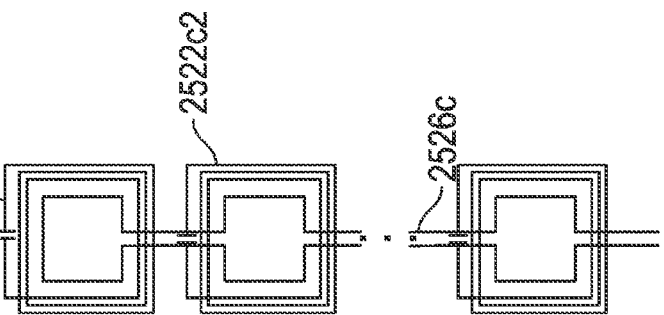
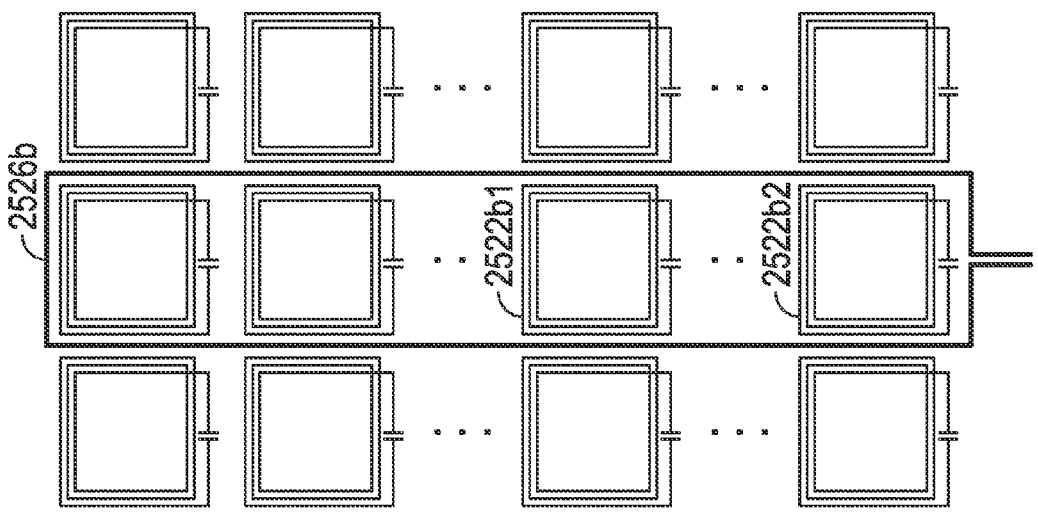
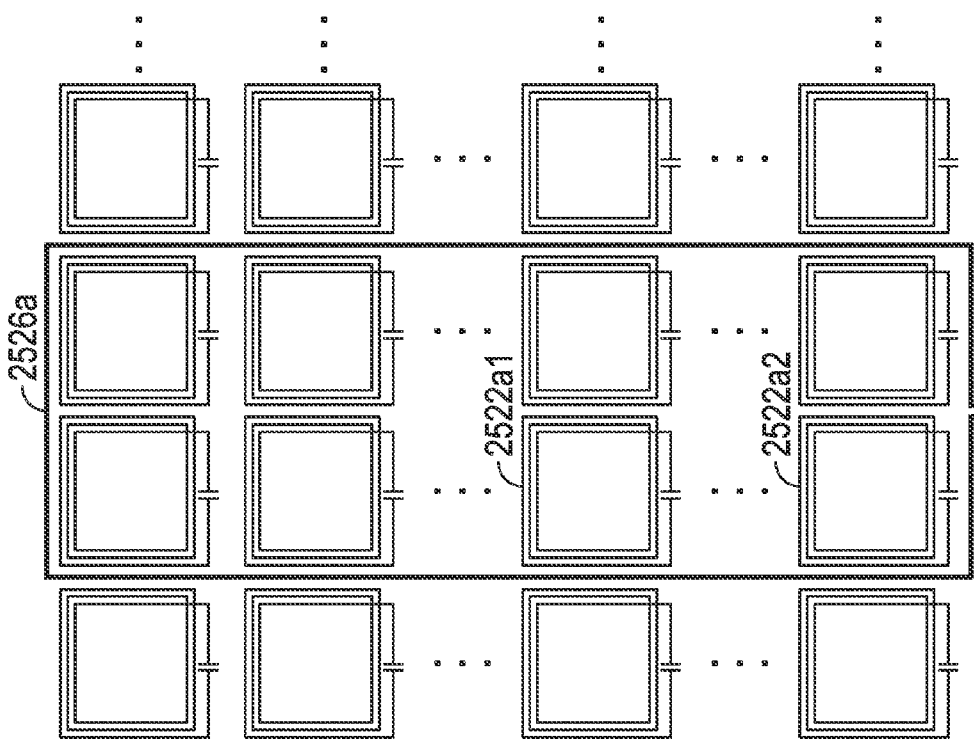
FIG. 25A
FIG. 25B
FIG. 25C

SYSTEMS, METHODS, AND APPARATUS FOR DETECTION OF METAL OBJECTS IN A PREDETERMINED SPACE

CROSS REFERENCE TO RELATED APPLICATIONS

This application claims priority to and the benefit under 35 U.S.C. §119(e) of U.S. Provisional Patent Application No. 61/671,498 entitled "SYSTEMS, METHODS, AND APPARATUS FOR DETECTION OF METAL OBJECTS IN A PREDETERMINED SPACE" filed on Jul. 13, 2012, the disclosure of which is hereby incorporated by reference in its entirety.

FIELD

The present disclosure relates generally to wireless power transfer, and more specifically to devices, systems, and methods related to wireless power transfer to remote systems such as vehicles including batteries. More specifically the present disclosure relates to the detection of foreign objects.

BACKGROUND

Remote systems, such as vehicles, have been introduced that include locomotion power derived from electricity received from an energy storage device such as a battery. For example, hybrid electric vehicles include on-board chargers that use power from vehicle braking and traditional motors to charge the vehicles. Vehicles that are solely electric generally receive the electricity for charging the batteries from other sources. Battery electric vehicles (electric vehicles) are often proposed to be charged through some type of wired alternating current (AC) such as household or commercial AC supply sources. The wired charging connections require cables or other similar connectors that are physically connected to a power supply. Cables and similar connectors may sometimes be inconvenient or cumbersome and have other drawbacks. Wireless charging systems that are capable of transferring power in free space (e.g., via a wireless field) to be used to charge electric vehicles may overcome some of the deficiencies of wired charging solutions. As such, wireless charging systems and methods that efficiently and safely transfer power for charging electric vehicles are desirable.

SUMMARY

Various implementations of systems, methods and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

One aspect of the disclosure provides an apparatus for detecting a presence of an object. The apparatus includes a resonant circuit having a resonant frequency. The resonant circuit includes a sense circuit including an electrically conductive structure. The apparatus further includes a coupling circuit coupled to the sense circuit. The apparatus further includes a detection circuit coupled to the sense circuit via the coupling circuit. The detection circuit is configured to detect the presence of the object in response to detecting a difference between a measured characteristic that depends on a frequency at which the resonant circuit is resonating and a corresponding characteristic that depends on the resonant frequency of the resonant circuit. The coupling circuit is configured to reduce a variation of the resonant frequency by the detection circuit in the absence of the object.

Another aspect of the disclosure provides an implementation of a method for detecting a presence of an object. The method includes applying a signal to a resonant circuit having a resonant frequency. The resonant circuit includes a sense circuit including an electrically conductive structure. A coupling circuit is coupled to the sense circuit. The method further includes detecting the presence of the object via a detection circuit coupled to the sense circuit via the coupling circuit in response to detecting a difference between a measured characteristic that depends on a frequency at which the resonant circuit is resonating and a corresponding characteristic that depends on the resonant frequency of the resonant circuit. The coupling circuit is configured to reduce a variation of the resonant frequency by the detection circuit in the absence of the object.

Yet another aspect of the disclosure provides an apparatus for detecting a presence of an object. The apparatus includes means for resonating at a resonant frequency. The apparatus further includes means for detecting the presence of the object in response to detecting a difference between a measured characteristic that depends on a frequency at which the resonating means is resonating and a corresponding characteristic that depends on the resonant frequency of the resonating means. The apparatus further includes means for reducing variation of the resonant frequency by the detection means in the absence of the object.

Another aspect of the subject matter described in the disclosure provides an apparatus for detecting a presence of an object. The apparatus includes a first sense circuit including a first electrically conductive structure. At least the first sense circuit forms a first resonant circuit having a first resonant frequency. The apparatus further includes a second sense circuit including a second electrically conductive structure. At least the second sense circuit forms a second resonant circuit having a second resonant frequency. The second resonant frequency is different than the first resonant frequency. The apparatus further includes a detection circuit coupled to the first and second sense circuits. The detection circuit is configured detect the presence of the object in response to detecting a difference between a first measured characteristic that depends on a frequency at which the first resonant circuit is resonating and a first corresponding characteristic that depends on the first resonant frequency, or a difference between a second measured characteristic that depends on a frequency at which the second resonant circuit is resonating and a second corresponding characteristic that depends on the second resonant frequency.

Another aspect of the subject matter described in the disclosure provides an implementation of a method for detecting a presence of an object. The method includes applying a first signal to a first sense circuit including a first electrically conductive structure. At least the first sense circuit forms a first resonant circuit having a first resonant frequency. The method further includes applying a second signal to a second sense circuit including a second electrically conductive structure. At least the second sense circuit forms a second resonant circuit having a second resonant frequency. The second resonant frequency is different than the first resonant frequency. The method further includes detecting the presence of the object via a detection circuit in response to detecting a difference between a first measured characteristic that depends on a frequency at which the first resonant circuit is resonating and a first corresponding characteristic that depends on the first resonant frequency or a difference between a second measured characteristic that depends on a frequency at which the second resonant circuit is resonating and a second corresponding characteristic that depends on the second resonant frequency.

Another aspect of the subject matter described in the disclosure provides an apparatus for detecting a presence of an object. The apparatus includes a first means for resonating at a first resonant frequency. The apparatus further includes a second means for resonating at a second resonant frequency. The second resonant frequency is different than the first resonant frequency. The apparatus further includes means for detecting the presence of the object in response to detecting a difference between a first measured characteristic that depends on a frequency at which the first resonating means is resonating and a first corresponding characteristic that depends on the first resonant frequency or a difference between a second measured characteristic that depends on a frequency at which the second resonating means is resonating and a second corresponding characteristic that depends on the second resonant frequency.

Another aspect of the subject matter described in the disclosure provides an apparatus for detecting a presence of an object in a magnetic field. The apparatus includes a power circuit configured to generate the magnetic field and transfer power wirelessly at a level sufficient to power or charge a load via the magnetic field. The magnetic field causes a vibration of the object. The apparatus further includes a detection circuit configured to transmit signals and detect, based on a reflection of the transmitted signals, a frequency of the vibration of the object caused by the magnetic field.

Another aspect of the subject matter described in the disclosure provides an implementation of a method for detecting a presence of an object in a magnetic field. The method includes generating the magnetic field and transferring power wirelessly at a level sufficient to power or charge a load via the magnetic field. The magnetic field causes a vibration of the object. The method further includes transmitting signals and detecting, based on a reflection of the transmitted signals, a frequency of the vibration of the object caused by the magnetic field.

Another aspect of the subject matter described in the disclosure provides an apparatus for detecting a presence of an object in a magnetic field. The apparatus includes means for generating the magnetic field and transferring power wirelessly at a level sufficient to power or charge a load via the magnetic field. The magnetic field causes a vibration of the object. The apparatus further includes means for transmitting signals and means for detecting, based on a reflection of the transmitted signals, a frequency of the vibration of the object caused by the magnetic field.

BRIEF DESCRIPTION OF THE DRAWINGS

FIGS. 25A, 25B, 25C, 25D, 25E, and 25F are diagrams of exemplary configurations sense loop arrays inductively or capacitivley coupled to a detection circuit, in accordance with an exemplary embodiment.

Figure 1:
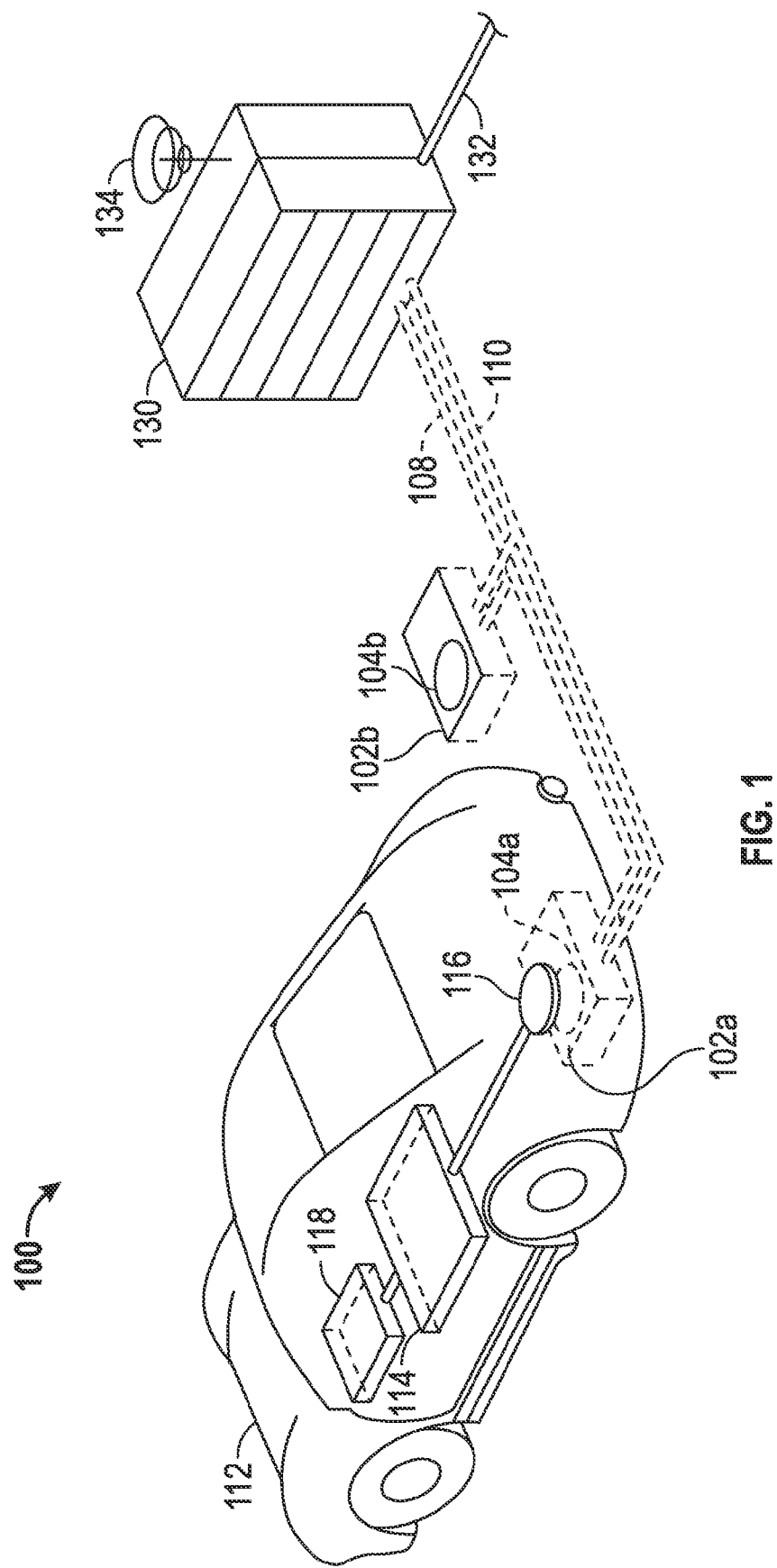
FIG. 1 is a diagram of an exemplary wireless power transfer system for charging an electric vehicle, in accordance with an exemplary embodiment.

The various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

The detailed description set forth below in connection with the appended drawings is intended as a description of exemplary embodiments and is not intended to represent the only embodiments in which the invention may be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments. In some instances, some devices are shown in block diagram form.

Wirelessly transferring power may refer to transferring any form of energy associated with electric fields, magnetic fields, electromagnetic fields, or otherwise from a transmitter to a receiver without the use of physical electrical conductors (e.g., power may be transferred through free space). The power output into a wireless field (e.g., a magnetic field) may be received, captured by, or coupled by a "receiving coil" to achieve power transfer.

An electric vehicle is used herein to describe a remote system, an example of which is a vehicle that includes, as part of its locomotion capabilities, electrical power derived from a chargeable energy storage device (e.g., one or more rechargeable electrochemical cells or other type of battery). As non-limiting examples, some electric vehicles may be hybrid electric vehicles that include besides electric motors, a traditional combustion engine for direct locomotion or to charge the vehicle's battery. Other electric vehicles may draw all locomotion ability from electrical power. An electric vehicle is not limited to an automobile and may include motorcycles, carts, scooters, and the like. By way of example and not limitation, a remote system is described herein in the form of an electric vehicle (EV). Furthermore, other remote systems that may be at least partially powered using a chargeable energy storage device are also contemplated (e.g., electronic devices such as personal computing devices and the like).

FIG. 1 is a diagram of an exemplary wireless power transfer system 100 for charging an electric vehicle 112, in accordance with an exemplary embodiment. The wireless power transfer system 100 enables charging of an electric vehicle 112 while the electric vehicle 112 is parked near a base wireless charging system 102a. Spaces for two electric vehicles are illustrated in a parking area to be parked over corresponding base wireless charging system 102a and 102b. In some embodiments, a local distribution center 130 may be connected to a power backbone 132 and configured to provide an alternating current (AC) or a direct current (DC) supply through a power link 110 to the base wireless charging system 102a. The base wireless charging system 102a also includes a base system induction coil 104a for wirelessly transferring or receiving power. An electric vehicle 112 may include a battery unit 118, an electric vehicle induction coil 116, and an electric vehicle wireless charging system 114. The electric vehicle induction coil 116 may interact with the base system induction coil 104a for example, via a region of the electromagnetic field generated by the base system induction coil 104a.

In some exemplary embodiments, the electric vehicle induction coil 116 may receive power when the electric vehicle induction coil 116 is located in an energy field produced by the base system induction coil 104a. The field corresponds to a region where energy output by the base system induction coil 104a may be captured by an electric vehicle induction coil 116. For example, the energy output by the base system induction coil 104a may be at a level sufficient to charge or power the electric vehicle 112. In some cases, the field may correspond to the "near field" of the base system induction coil 104a. The near-field may correspond to a region in which there are strong reactive fields resulting from the currents and charges in the base system induction coil 104a that do not radiate power away from the base system induction coil 104a. In some cases the near-field may correspond to a region that is within about $\frac{1}{2}\pi$ of wavelength of the base system induction coil 104a (and vice versa for the electric vehicle induction coil 116) as will be further described below.

Local distribution 1130 may be configured to communicate with external sources (e.g., a power grid) via a communication backhaul 134, and with the base wireless charging system 102a via a communication link 108.

In some embodiments the electric vehicle induction coil 116 may be aligned with the base system induction coil 104a and, therefore, disposed within a near-field region simply by the driver positioning the electric vehicle 112 correctly relative to the base system induction coil 104a. In other embodiments, the driver may be given visual feedback, auditory feedback, or combinations thereof to determine when the electric vehicle 112 is properly placed for wireless power transfer. In yet other embodiments, the electric vehicle 112 may be positioned by an autopilot system, which may move the electric vehicle 112 back and forth (e.g., in zig-zag movements) until an alignment error has reached a tolerable value. This may be performed automatically and autonomously by the electric vehicle 112 without or with only minimal driver intervention provided that the electric vehicle 112 is equipped with a servo steering wheel, ultrasonic sensors, and intelligence to adjust the vehicle. In still other embodiments, the electric vehicle induction coil 116, the base system induction coil 104a, or a combination thereof may have functionality for displacing and moving the induction coils 116 and 104a relative to each other to more accurately orient them and develop more efficient coupling therebetween.

The base wireless charging system 102a may be located in a variety of locations. As non-limiting examples, some suitable locations include a parking area at a home of the electric vehicle 112 owner, parking areas reserved for electric vehicle wireless charging modeled after conventional petroleum-based filling stations, and parking lots at other locations such as shopping centers and places of employment.

Charging electric vehicles wirelessly may provide numerous benefits. For example, charging may be performed automatically, virtually without driver intervention and manipulations thereby improving convenience to a user. There may also be no exposed electrical contacts and no mechanical wear out, thereby improving reliability of the wireless power transfer system 100. Manipulations with cables and connectors may not be needed, and there may be no cables, plugs, or sockets that may be exposed to moisture and water in an outdoor environment, thereby improving safety. There may also be no sockets, cables, and plugs visible or accessible, thereby reducing potential vandalism of power charging devices. Further, since an electric vehicle 112 may be used as distributed storage devices to stabilize a power grid, a docking-to-grid solution may be used to increase availability of vehicles for Vehicle-to-Grid (V2G) operation.

A wireless power transfer system 100 as described with reference to FIG. 1 may also provide aesthetical and non-impedimental advantages. For example, there may be no charge columns and cables that may be impedimental for vehicles and/or pedestrians.

As a further explanation of the vehicle-to-grid capability, the wireless power transmit and receive capabilities may be configured to be reciprocal such that the base wireless charging system 102a transfers power to the electric vehicle 112 and the electric vehicle 112 transfers power to the base wireless charging system 102a e.g., in times of energy shortfall. This capability may be useful to stabilize the power distribution grid by allowing electric vehicles to contribute power to the overall distribution system in times of energy shortfall caused by over demand or shortfall in renewable energy production (e.g., wind or solar).

Figure 2:
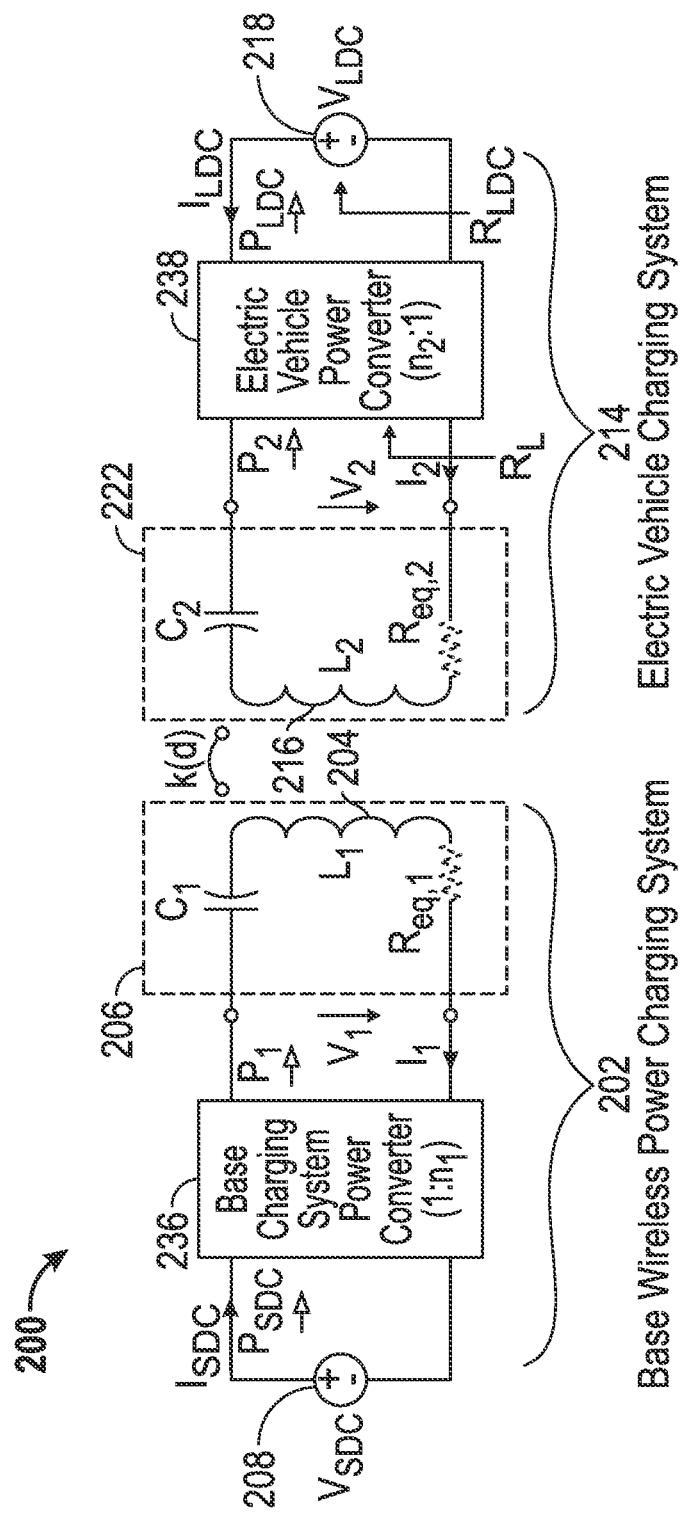
FIG. 2 is a schematic diagram of exemplary core components of the wireless power transfer system of FIG. 1.

FIG. 2 is a schematic diagram of exemplary core components of the wireless power transfer system 100 of FIG. 1. As shown in FIG. 2, the wireless power transfer system 200 may include a base system transmit circuit 206 including a base system induction coil 204 having an inductance $L_1$. The wireless power transfer system 200 further includes an electric vehicle receive circuit 222 including an electric vehicle induction coil 216 having an inductance $L_2$. Embodiments described herein may use capacitively loaded wire loops (i.e., multi-turn coils) forming a resonant structure that is capable of efficiently coupling energy from a primary structure (transmitter) to a secondary structure (receiver) via a magnetic or electromagnetic near field if both primary and secondary are tuned to a common resonant frequency. The coils may be used for the electric vehicle induction coil 216 and the base system induction coil 204. Using resonant structures for coupling energy may be referred to "magnetic coupled resonance," "electromagnetic coupled resonance," and/or "resonant induction." The operation of the wireless power transfer system 200 will be described based on power transfer from a base wireless power charging system 202 to an electric vehicle 112, but is not limited thereto. For example, as discussed above, the electric vehicle 112 may transfer power to the base wireless charging system 102a.

With reference to FIG. 2, a power supply 208 (e.g., AC or DC) supplies power $P_{SDC}$ to the base wireless power charging system 202 to transfer energy to an electric vehicle 112. The base wireless power charging system 202 includes a base charging system power converter 236. The base charging system power converter 236 may include circuitry such as an AC/DC converter configured to convert power from standard mains AC to DC power at a suitable voltage level, and a DC/low frequency (LF) converter configured to convert DC power to power at an operating frequency suitable for wireless high power transfer. The base charging system power converter 236 supplies power $P_1$ to the base system transmit circuit 206 including the capacitor $C_1$ in series with the base system induction coil 204 to emit an electromagnetic field at a desired frequency. The capacitor $C_1$ may be coupled with the base system induction coil 204 either in parallel or in series, or may be formed of several reactive elements in any combination of parallel or series topology. The capacitor $C_1$ may be provided to form a resonant circuit with the base system induction coil 204 that resonates at a desired frequency. The base system induction coil 204 receives the power $P_1$ and wirelessly transmits power at a level sufficient to charge or power the electric vehicle 112. For example, the power level provided wirelessly by the base system induction coil 204 may be on the order of kilowatts (kW) (e.g., anywhere from 1 kW to 110 kW or higher or lower).

The base system transmit circuit 206 including the base system induction coil 204 and electric vehicle receive circuit 222 including the electric vehicle induction coil 216 may be tuned to substantially the same frequencies and may be positioned within the near-field of an electromagnetic field transmitted by one of the base system induction coil 204 and the electric vehicle induction coil 116. In this case, the base system induction coil 204 and electric vehicle induction coil 116 may become coupled to one another such that power may be transferred to the electric vehicle receive circuit 222 including capacitor $C_2$ and electric vehicle induction coil 116. The capacitor $C_2$ may be provided to form a resonant circuit with the electric vehicle induction coil 216 that resonates at a desired frequency. The capacitor $C_2$ may be coupled with the electric vehicle induction coil 204 either in parallel or in series, or may be formed of several reactive elements in any combination of parallel or series topology. Element k(d) represents the mutual coupling coefficient resulting at coil separation. Equivalent resistances $R_{eq,1}$ and $R_{eq,2}$ represent the losses that may be inherent to the induction coils 204 and 216 and the anti-reactance capacitors $C_1$ and $C_2$. The electric vehicle receive circuit 222 including the electric vehicle induction coil 316 and capacitor $C_2$ receives power $P_2$ and provides the power $P_2$ to an electric vehicle power converter 238 of an electric vehicle charging system 214.

The electric vehicle power converter 238 may include, among other things, a LF/DC converter configured to convert power at an operating frequency back to DC power at a voltage level matched to the voltage level of an electric vehicle battery unit 218. The electric vehicle power converter 238 may provide the converted power $P_{LDC}$ to charge the electric vehicle battery unit 218. The power supply 208, base charging system power converter 236, and base system induction coil 204 may be stationary and located at a variety of locations as discussed above. The battery unit 218, electric vehicle power converter 238, and electric vehicle induction coil 216 may be included in an electric vehicle charging system 214 that is part of electric vehicle 112 or part of the battery pack (not shown). The electric vehicle charging system 214 may also be configured to provide power wirelessly through the electric vehicle induction coil 216 to the base wireless power charging system 202 to feed power back to the grid. Each of the electric vehicle induction coil 216 and the base system induction coil 204 may act as transmit or receive induction coils based on the mode of operation.

While not shown, the wireless power transfer system 200 may include a load disconnect unit (LDU) to safely disconnect the electric vehicle battery unit 218 or the power supply 208 from the wireless power transfer system 200. For example, in case of an emergency or system failure, the LDU may be triggered to disconnect the load from the wireless power transfer system 200. The LDU may be provided in addition to a battery management system for managing charging to a battery, or it may be part of the battery management system.

Further, the electric vehicle charging system 214 may include switching circuitry (not shown) for selectively connecting and disconnecting the electric vehicle induction coil 216 to the electric vehicle power converter 238. Disconnecting the electric vehicle induction coil 216 may suspend charging and also may adjust the "load" as "seen" by the base wireless charging system 102a (acting as a transmitter), which may be used to "cloak" the electric vehicle charging system 114 (acting as the receiver) from the base wireless charging system 102a. The load changes may be detected if the transmitter includes the load sensing circuit. Accordingly, the transmitter, such as a base wireless charging system 202, may have a mechanism for determining when receivers, such as an electric vehicle charging system 114, are present in the near-field of the base system induction coil 204.

As described above, in operation, assuming energy transfer towards the vehicle or battery, input power is provided from the power supply 208 such that the base system induction coil 204 generates a field for providing the energy transfer. The electric vehicle induction coil 216 couples to the radiated field and generates output power for storage or consumption by the electric vehicle 112. As described above, in some embodiments, the base system induction coil 204 and electric vehicle induction coil 116 are configured according to a mutual resonant relationship such that when the resonant frequency of the electric vehicle induction coil 116 and the resonant frequency of the base system induction coil 204 are very close or substantially the same. Transmission losses between the base wireless power charging system 202 and electric vehicle charging system 214 are minimal when the electric vehicle induction coil 216 is located in the near-field of the base system induction coil 204.

As stated, an efficient energy transfer occurs by coupling a large portion of the energy in the near field of a transmitting induction coil to a receiving induction coil rather than propagating most of the energy in an electromagnetic wave to the far-field. When in the near field, a coupling mode may be established between the transmit induction coil and the receive induction coil. The area around the induction coils where this near field coupling may occur is referred to herein as a near field coupling mode region.

While not shown, the base charging system power converter 236 and the electric vehicle power converter 238 may both include an oscillator, a driver circuit such as a power amplifier, a filter, and a matching circuit for efficient coupling with the wireless power induction coil. The oscillator may be configured to generate a desired frequency, which may be adjusted in response to an adjustment signal. The oscillator signal may be amplified by a power amplifier with an amplification amount responsive to control signals. The filter and matching circuit may be included to filter out harmonics or other unwanted frequencies and match the impedance of the power conversion module to the wireless power induction coil. The power converters 236 and 238 may also include a rectifier and switching circuitry to generate a suitable power output to charge the battery.

The electric vehicle induction coil 216 and base system induction coil 204 as described throughout the disclosed embodiments may be referred to or configured as "loop" antennas, and more specifically, multi-turn loop antennas. The induction coils 204 and 216 may also be referred to herein or be configured as "magnetic" antennas. The term "coils" is intended to refer to a component that may wirelessly output or receive energy four coupling to another "coil." The coil may also be referred to as an "antenna" of a type that is configured to wirelessly output or receive power. As used herein, coils 204 and 216 are examples of "power transfer components" of a type that are configured to wirelessly output, wirelessly receive, and/or wirelessly relay power. Loop (e.g., multi-turn loop) antennas may be configured to include an air core or a physical core such as a ferrite core. An air core loop antenna may allow the placement of other components within the core area. Physical core antennas including ferromagnetic or ferromagnetic materials may allow development of a stronger electromagnetic field and improved coupling.

As discussed above, efficient transfer of energy between a transmitter and receiver occurs during matched or nearly matched resonance between a transmitter and a receiver. However, even when resonance between a transmitter and receiver are not matched, energy may be transferred at a lower efficiency. Transfer of energy occurs by coupling energy from the near field of the transmitting induction coil to the receiving induction coil residing within a region (e.g., within a predetermined frequency range of the resonant frequency, or within a predetermined distance of the near-field region) where this near field is established rather than propagating the energy from the transmitting induction coil into free space.

A resonant frequency may be based on the inductance and capacitance of a transmit circuit including an induction coil (e.g., the base system induction coil 204) as described above. As shown in FIG. 2, inductance may generally be the inductance of the induction coil, whereas, capacitance may be added to the induction coil to create a resonant structure at a desired resonant frequency. As a non-limiting example, as shown in FIG. 2, a capacitor may be added in series with the induction coil to create a resonant circuit (e.g., the base system transmit circuit 206) that generates an electromagnetic field. Accordingly, for larger diameter induction coils, the value of capacitance needed to induce resonance may decrease as the diameter or inductance of the coil increases. Inductance may also depend on a number of turns of an induction coil. Furthermore, as the diameter of the induction coil increases, the efficient energy transfer area of the near field may increase. Other resonant circuits are possible. As another non limiting example, a capacitor may be placed in parallel between the two terminals of the induction coil (e.g., a parallel resonant circuit). Furthermore an induction coil may be designed to have a high quality (Q) factor to improve the resonance of the induction coil. For example, the Q factor may be 300 or greater.

As described above, according to some embodiments, coupling power between two induction coils that are in the near field of one another is disclosed. As described above, the near field may correspond to a region around the induction coil in which electromagnetic fields exist but may not propagate or radiate away from the induction coil. Near-field coupling-mode regions may correspond to a volume that is near the physical volume of the induction coil, typically within a small fraction of the wavelength. According to some embodiments, electromagnetic induction coils, such as single and multi-turn loop antennas, are used for both transmitting and receiving since magnetic near field amplitudes in practical embodiments tend to be higher for magnetic type coils in comparison to the electric near fields of an electric type antenna (e.g., a small dipole). This allows for potentially higher coupling between the pair. Furthermore, "electric" antennas (e.g., dipoles and monopoles) or a combination of magnetic and electric antennas may be used.

Figure 3:
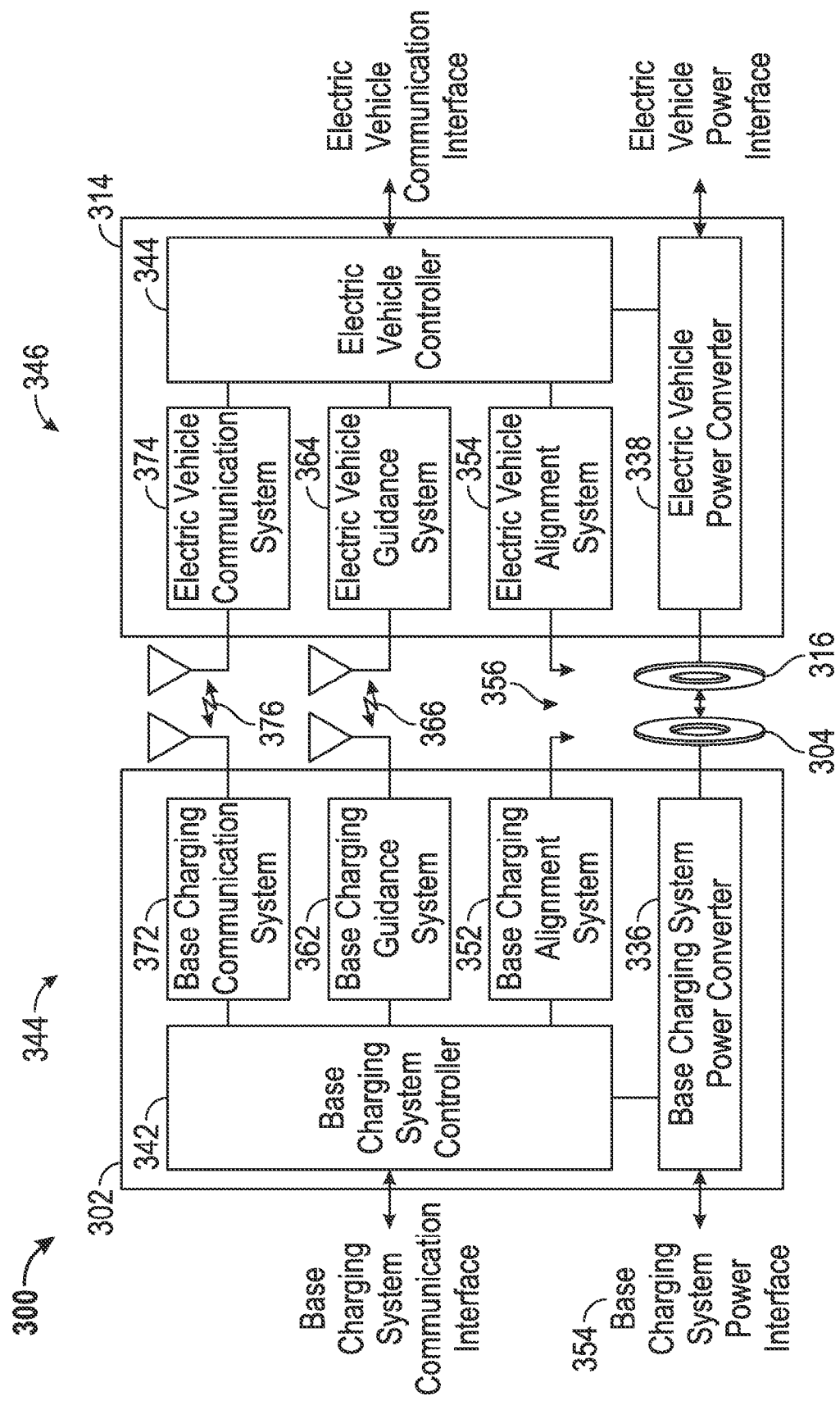
FIG. 3 is another functional block diagram showing exemplary core and ancillary components of the wireless power transfer system of FIG. 1.

FIG. 3 is another functional block diagram showing exemplary core and ancillary components of the wireless power transfer system 300 of FIG. 1. The wireless power transfer system 300 illustrates a communication link 376, a guidance link 366, and alignment systems 352, 354 for the base system induction coil 304 and electric vehicle induction coil 316. As described above with reference to FIG. 2, and assuming energy flow towards the electric vehicle 112, in FIG. 3 a base charging system power interface 354 may be configured to provide power to a charging system power converter 336 from a power source, such as an AC or DC power supply 126. The base charging system power converter 336 may receive AC or DC power from the base charging system power interface 354 to excite the base system induction coil 304 at or near its resonant frequency. The electric vehicle induction coil 316, when in the near field coupling-mode region, may receive energy from the near field coupling mode region to oscillate at or near the resonant frequency. The electric vehicle power converter 338 converts the oscillating signal from the electric vehicle induction coil 316 to a power signal suitable for charging a battery via the electric vehicle power interface.

The base wireless charging system 302 includes a base charging system controller 342 and the electric vehicle charging system 314 includes an electric vehicle controller 344. The base charging system controller 342 may include a base charging system communication interface 162 to other systems (not shown) such as, for example, a computer, and a power distribution center, or a smart power grid. The electric vehicle controller 344 may include an electric vehicle communication interface to other systems (not shown) such as, for example, an on-board computer on the vehicle, other battery charging controller, other electronic systems within the vehicles, and remote electronic systems.

The base charging system controller 342 and electric vehicle controller 344 may include subsystems or modules for specific application with separate communication channels. These communications channels may be separate physical channels or separate logical channels. As non-limiting examples, a base charging alignment system 352 may communicate with an electric vehicle alignment system 354 through a communication link 376 to provide a feedback mechanism for more closely aligning the base system induction coil 304 and electric vehicle induction coil 316, either autonomously or with operator assistance. Similarly, a base charging guidance system 362 may communicate with an electric vehicle guidance system 364 through a guidance link to provide a feedback mechanism to guide an operator in aligning the base system induction coil 304 and electric vehicle induction coil 316. In addition, there may be separate general-purpose communication links (e.g., channels) supported by base charging communication system 372 and electric vehicle communication system 374 for communicating other information between the base wireless power charging system 302 and the electric vehicle charging system 314. This information may include information about electric vehicle characteristics, battery characteristics, charging status, and power capabilities of both the base wireless power charging system 302 and the electric vehicle charging system 314, as well as maintenance and diagnostic data for the electric vehicle 112. These communication channels may be separate physical communication channels such as, for example, Bluetooth, zigbee, cellular, etc.

Electric vehicle controller 344 may also include a battery management system (BMS) (not shown) that manages charge and discharge of the electric vehicle principal battery, a parking assistance system based on microwave or ultrasonic radar principles, a brake system configured to perform a semi-automatic parking operation, and a steering wheel servo system configured to assist with a largely automated parking 'park by wire' that may provide higher parking accuracy, thus reducing the need for mechanical horizontal induction coil alignment in any of the base wireless charging system 102a and the electric vehicle charging system 114. Further, electric vehicle controller 344 may be configured to communicate with electronics of the electric vehicle 112. For example, electric vehicle controller 344 may be configured to communicate with visual output devices (e.g., a dashboard display), acoustic/audio output devices (e.g., buzzer, speakers), mechanical input devices (e.g., keyboard, touch screen, and pointing devices such as joystick, trackball, etc.), and audio input devices (e.g., microphone with electronic voice recognition).

Furthermore, the wireless power transfer system 300 may include detection and sensor systems. For example, the wireless power transfer system 300 may include sensors for use with systems to properly guide the driver or the vehicle to the charging spot, sensors to mutually align the induction coils with the required separation/coupling, sensors to detect objects that may obstruct the electric vehicle induction coil 316 from moving to a particular height and/or position to achieve coupling, and safety sensors for use with systems to perform a reliable, damage free, and safe operation of the system. For example, a safety sensor may include a sensor for detection of presence of animals or children approaching the wireless power induction coils 104a, 116 beyond a safety radius, detection of metal objects near the base system induction coil 304 that may be heated up (induction heating), detection of hazardous events such as incandescent objects on the base system induction coil 304, and temperature monitoring of the base wireless power charging system 302 and electric vehicle charging system 314 components.

The wireless power transfer system 300 may also support plug-in charging via a wired connection. A wired charge port may integrate the outputs of the two different chargers prior to transferring power to or from the electric vehicle 112. Switching circuits may provide the functionality as needed to support both wireless charging and charging via a wired charge port.

To communicate between a base wireless charging system 302 and an electric vehicle charging system 314, the wireless power transfer system 300 may use both in-band signaling and an RF data modem (e.g., Ethernet over radio in an unlicensed band). The out-of-band communication may provide sufficient bandwidth for the allocation of value-add services to the vehicle user/owner. A low depth amplitude or phase modulation of the wireless power carrier may serve as an in-band signaling system with minimal interference.

In addition, some communication may be performed via the wireless power link without using specific communications antennas. For example, the wireless power induction coils 304 and 316 may also be configured to act as wireless communication transmitters. Thus, some embodiments of the base wireless power charging system 302 may include a controller (not shown) for enabling keying type protocol on the wireless power path. By keying the transmit power level (amplitude shift keying) at predefined intervals with a predefined protocol, the receiver may detect a serial communication from the transmitter. The base charging system power converter 336 may include a load sensing circuit (not shown) for detecting the presence or absence of active electric vehicle receivers in the vicinity of the near field generated by the base system induction coil 304. By way of example, a load sensing circuit monitors the current flowing to the power amplifier, which is affected by the presence or absence of active receivers in the vicinity of the near field generated by base system induction coil 104a. Detection of changes to the loading on the power amplifier may be monitored by the base charging system controller 342 for use in determining whether to enable the oscillator for transmitting energy, to communicate with an active receiver, or a combination thereof.

To enable wireless high power transfer, some embodiments may be configured to transfer power at a frequency in the range from 10-60 kHz. This low frequency coupling may allow highly efficient power conversion that may be achieved using solid state devices. In addition, there may be less coexistence issues with radio systems compared to other bands.

Figure 4:
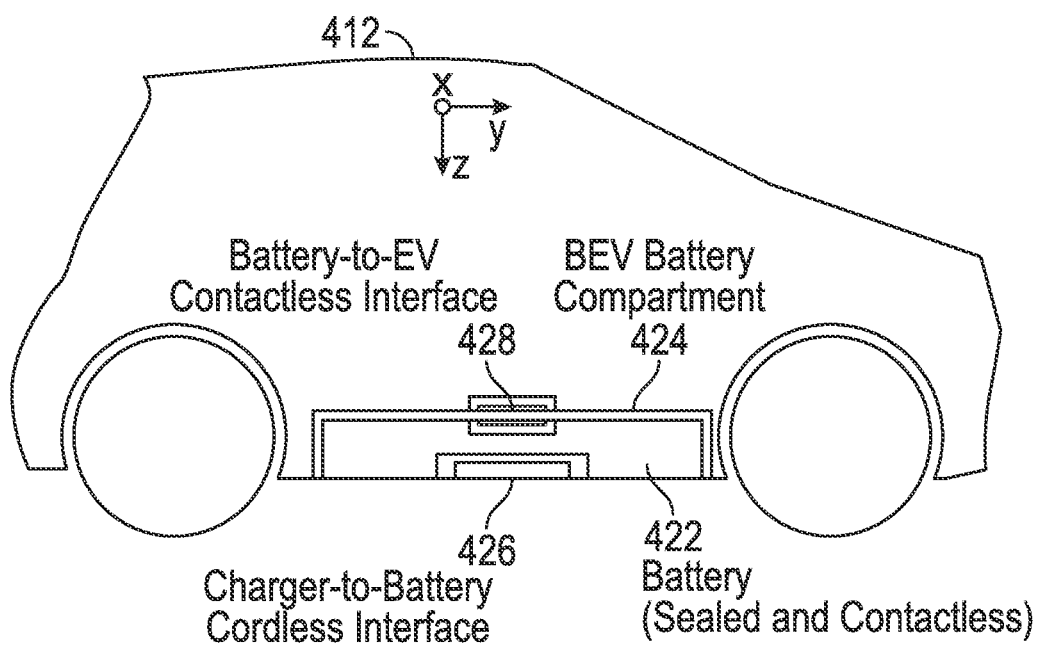
FIG. 4 is a functional block diagram showing a replaceable contactless battery disposed in an electric vehicle, in accordance with an exemplary embodiment.

The wireless power transfer system 100 described may be used with a variety of electric vehicles 102 including rechargeable or replaceable batteries. FIG. 4 is a functional block diagram showing a replaceable contactless battery disposed in an electric vehicle 412, in accordance with an exemplary embodiment. In this embodiment, the low battery position may be useful for an electric vehicle battery unit that integrates a wireless power interface (e.g., a charger-to-battery cordless interface 426) and that may receive power from a charger (not shown) embedded in the ground. In FIG. 4, the electric vehicle battery unit may be a rechargeable battery unit, and may be accommodated in a battery compartment 424. The electric vehicle battery unit also provides a wireless power interface 426, which may integrate the entire electric vehicle wireless power subsystem including a resonant induction coil, power conversion circuitry, and other control and communications functions as needed for efficient and safe wireless energy transfer between a ground-based wireless charging unit and the electric vehicle battery unit.

It may be useful for the electric vehicle induction coil to be integrated flush with a bottom side of electric vehicle battery unit or the vehicle body so that there are no protrusive parts and so that the specified ground-to-vehicle body clearance may be maintained. This configuration may require some room in the electric vehicle battery unit dedicated to the electric vehicle wireless power subsystem. The electric vehicle battery unit 422 may also include a battery-to-EV cordless interface 422, and a charger-to-battery cordless interface 426 that provides contactless power and communication between the electric vehicle 412 and a base wireless charging system 102a as shown in FIG. 1.

In some embodiments, and with reference to FIG. 1, the base system induction coil 104a and the electric vehicle induction coil 116 may be in a fixed position and the induction coils are brought within a near-field coupling region by overall placement of the electric vehicle induction coil 116 relative to the base wireless charging system 102a. However, in order to perform energy transfer rapidly, efficiently, and safely, the distance between the base system induction coil 104a and the electric vehicle induction coil 116 may need to be reduced to improve coupling. Thus, in some embodiments, the base system induction coil 104a and/or the electric vehicle induction coil 116 may be deployable and/or moveable to bring them into better alignment.

Figure 5A:
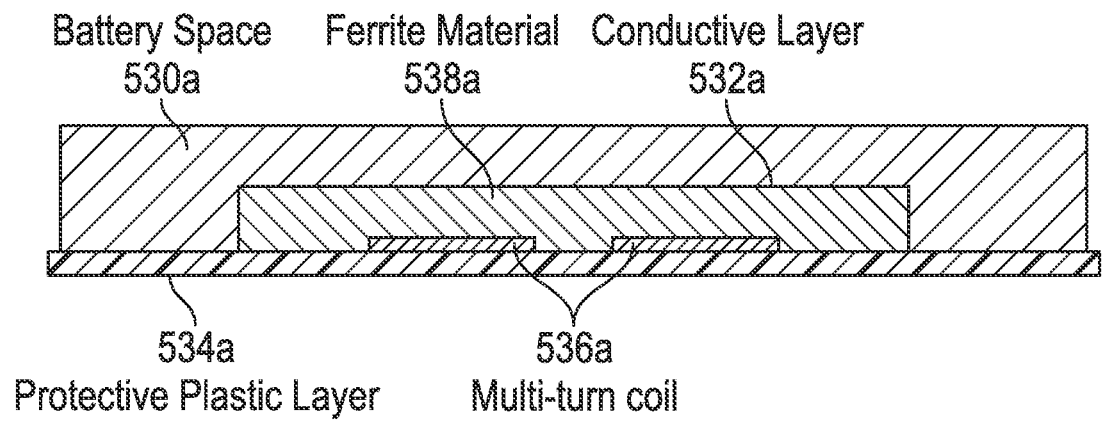
FIGS. 5A, 5B, 5C, and 5D are diagrams of exemplary configurations for the placement of an induction coil and ferrite material relative to a battery, in accordance with exemplary embodiments.

FIGS. 5A, 5B, 5C, and 5D are diagrams of exemplary configurations for the placement of an induction coil and ferrite material relative to a battery, in accordance with exemplary embodiments. FIG. 5A shows a fully ferrite embedded induction coil 536a. The wireless power induction coil may include a ferrite material 538a and a coil 536a wound about the ferrite material 538a. The coil 536a itself may be made of stranded Litz wire. A conductive shield 532a may be provided to protect passengers of the vehicle from excessive EMF transmission. Conductive shielding may be particularly useful in vehicles made of plastic or composites.

Figure 5B:
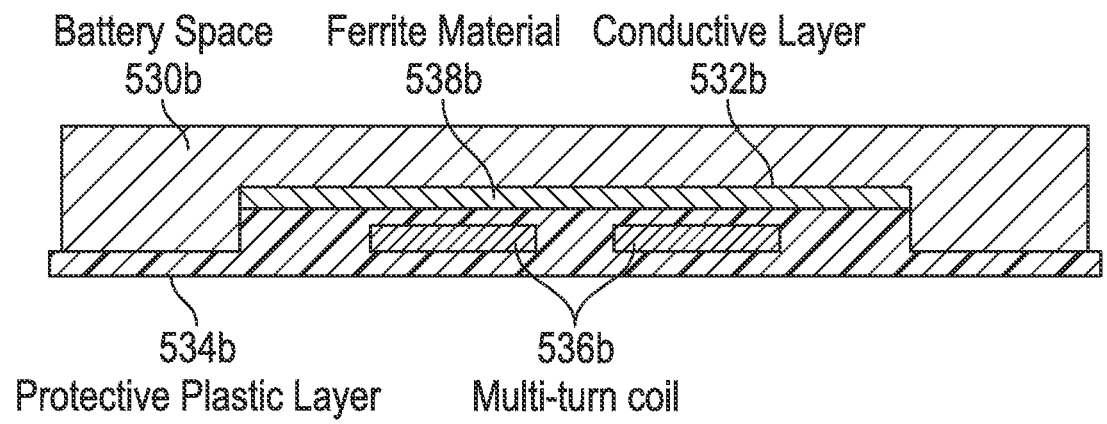

FIG. 5B shows an optimally dimensioned ferrite plate (i.e., ferrite backing) to enhance coupling and to reduce eddy currents (heat dissipation) in the conductive shield 532b. The coil 536b may be fully embedded in a non-conducting non-magnetic (e.g., plastic) material. For example, as illustrated in FIG. 5A-5D, the coil 536b may be embedded in a protective housing 534b. There may be a separation between the coil 536b and the ferrite material 538b as the result of a trade-off between magnetic coupling and ferrite hysteresis losses.

Figure 5C:
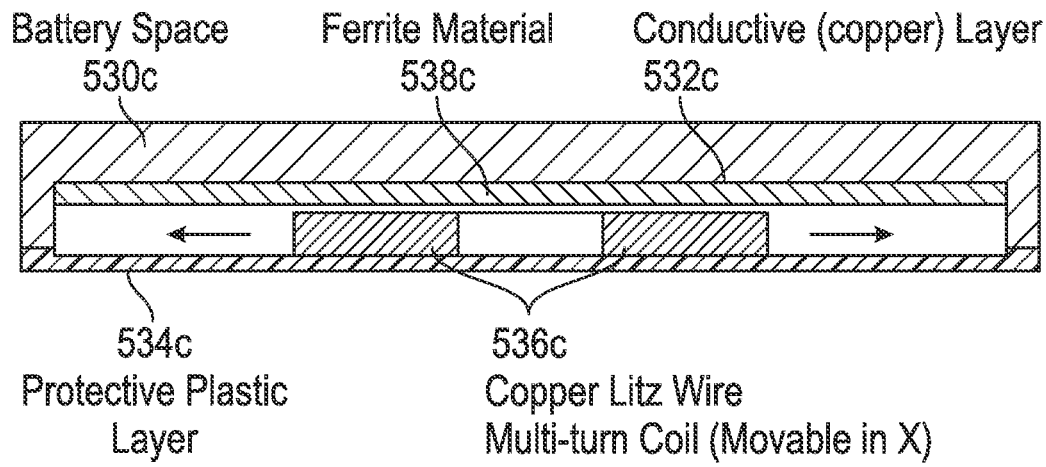
Figure 5D:
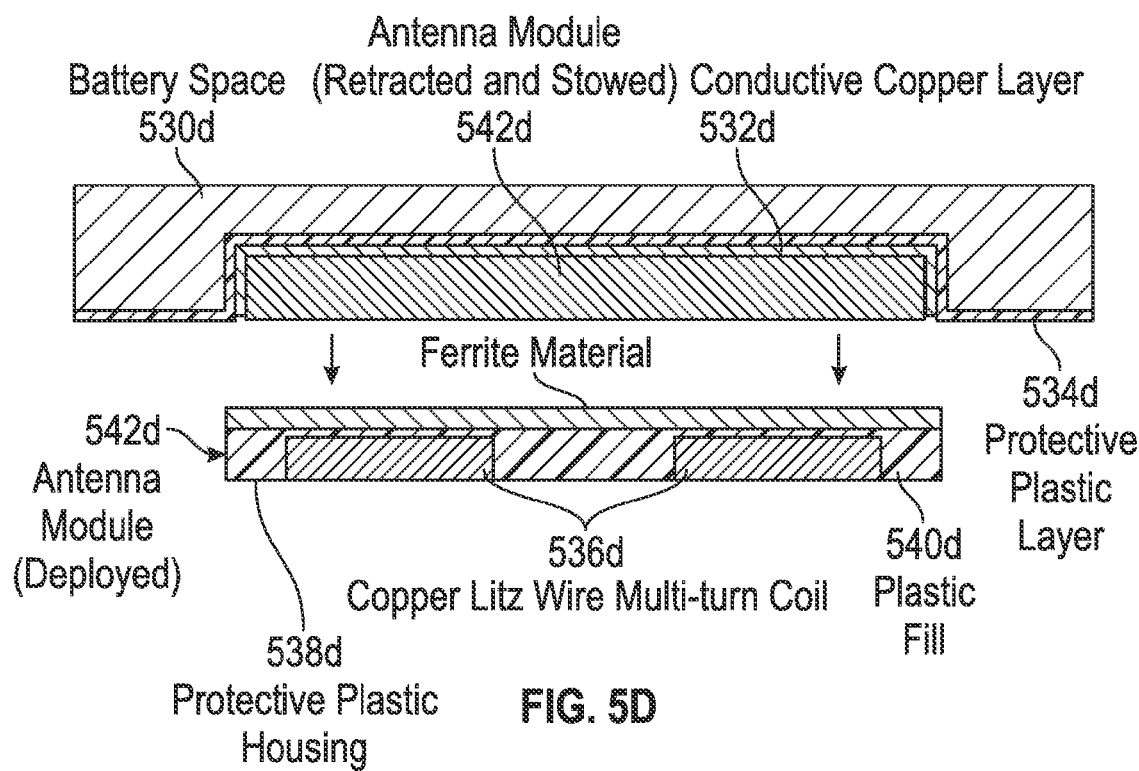

FIG. 5C illustrates another embodiment where the coil 536c (e.g., a copper Litz wire multi-turn coil) may be movable in a lateral ("X") direction. FIG. 5D illustrates another embodiment where the induction coil module is deployed in a downward direction. In some embodiments, the battery unit includes one of a deployable and non-deployable electric vehicle induction coil module 540d as part of the wireless power interface. To prevent magnetic fields from penetrating into the battery space 530d and into the interior of the vehicle, there may be a conductive shield 532d (e.g., a copper sheet) between the battery space 530d and the vehicle. Furthermore, a non-conductive (e.g., plastic) protective layer 533d may be used to protect the conductive shield 532d, the coil 536d, and the ferrite material 5d38 from environmental impacts (e.g., mechanical damage, oxidization, etc.). Furthermore, the coil 536d may be movable in lateral X and/or Y directions. FIG. 5D illustrates an embodiment wherein the electric vehicle induction coil module 540d is deployed in a downward Z direction relative to a battery unit body.

The design of this deployable electric vehicle induction coil module 542b is similar to that of FIG. 5B except there is no conductive shielding at the electric vehicle induction coil module 542d. The conductive shield 532d stays with the battery unit body. The protective layer 533d (e.g., plastic layer) is provided between the conductive shield 432d and the electric vehicle induction coil module 542d when the electric vehicle induction coil module 542d is not in a deployed state. The physical separation of the electric vehicle induction coil module 542 from the battery unit body may have a positive effect on the induction coil's performance.

As discussed above, the electric vehicle induction coil module 542d that is deployed may contain only the coil 536d (e.g., Litz wire) and ferrite material 538d. Ferrite backing may be provided to enhance coupling and to prevent from excessive eddy current losses in a vehicle's underbody or in the conductive shield 532d. Moreover, the electric vehicle induction coil module 542d may include a flexible wire connection to power conversion electronics and sensor electronics. This wire bundle may be integrated into the mechanical gear for deploying the electric vehicle induction coil module 542d.

With reference to FIG. 1, the charging systems described above may be used in a variety of locations for charging an electric vehicle 112, or transferring power back to a power grid. For example, the transfer of power may occur in a parking lot environment. It is noted that a "parking area" may also be referred to herein as a "parking space." To enhance the efficiency of a vehicle wireless power transfer system 100, an electric vehicle 112 may be aligned along an X direction and a Y direction to enable an electric vehicle induction coil 116 within the electric vehicle 112 to be adequately aligned with a base wireless charging system 102a within an associated parking area.

Furthermore, the disclosed embodiments are applicable to parking lots having one or more parking spaces or parking areas, wherein at least one parking space within a parking lot may comprise a base wireless charging system 102a. Guidance systems (not shown) may be used to assist a vehicle operator in positioning an electric vehicle 112 in a parking area to align an electric vehicle induction coil 116 within the electric vehicle 112 with a base wireless charging system 102a. Guidance systems may include electronic based approaches (e.g., radio positioning, direction finding principles, and/or optical, quasi-optical and/or ultrasonic sensing methods) or mechanical-based approaches (e.g., vehicle wheel guides, tracks or stops), or any combination thereof, for assisting an electric vehicle operator in positioning an electric vehicle 112 to enable an induction coil 116 within the electric vehicle 112 to be adequately aligned with a charging induction coil within a charging base (e.g., base wireless charging system 102a).

As discussed above, the electric vehicle charging system 114 may be placed on the underside of the electric vehicle 112 for transmitting and receiving power from a base wireless charging system 102a. For example, an electric vehicle induction coil 116 may be integrated into the vehicles underbody preferably near a center position providing maximum safety distance in regards to EM exposure and permitting forward and reverse parking of the electric vehicle.

Figure 6:
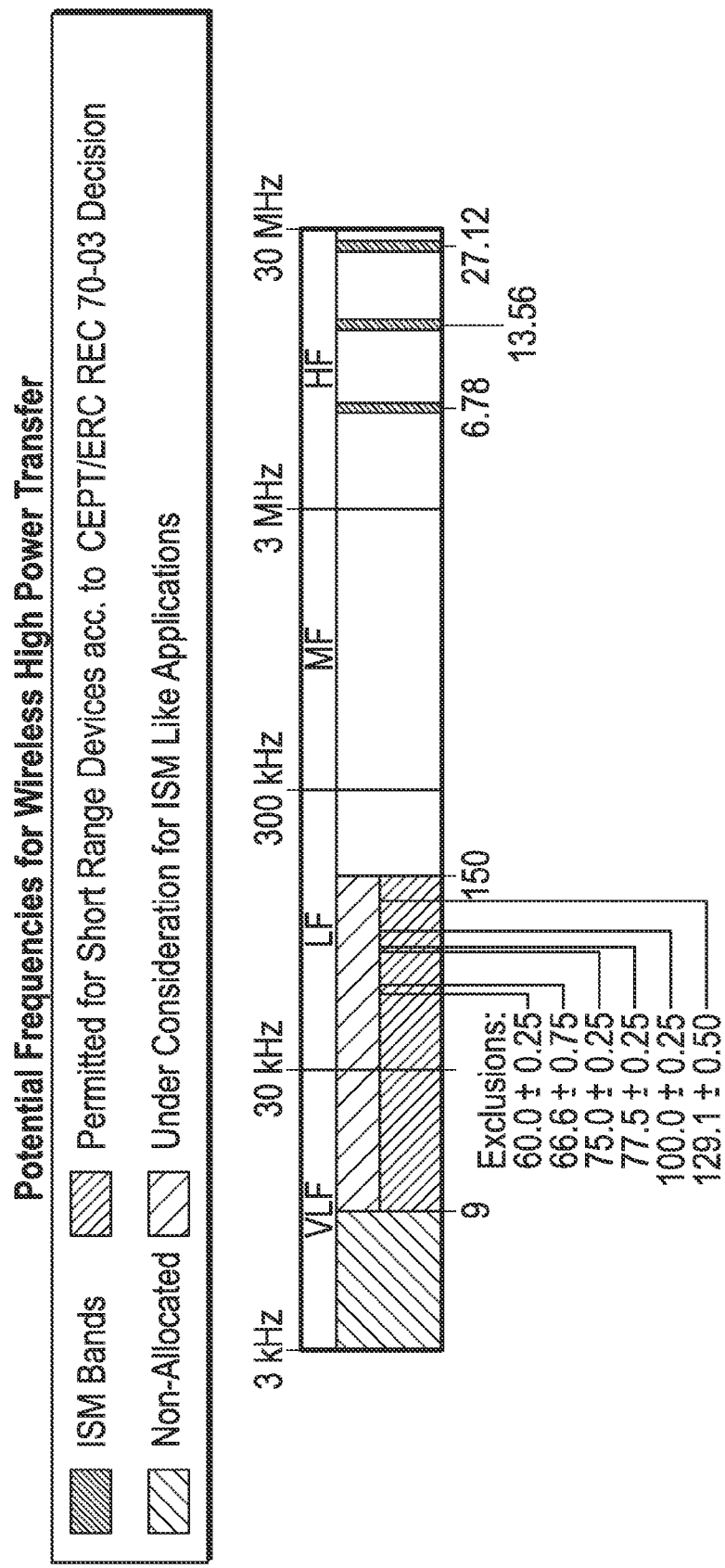
FIG. 6 is a chart of a frequency spectrum showing exemplary frequencies that may be available for wireless charging an electric vehicle, in accordance with an exemplary embodiment.

FIG. 6 is a chart of a frequency spectrum showing exemplary frequencies that may be used for wireless charging an electric vehicle, in accordance with an exemplary embodiment. As shown in FIG. 6, potential frequency ranges for wireless high power transfer to electric vehicles may include: VLF in a 3 kHz to 30 kHz band, lower LF in a 30 kHz to 150 kHz band (for ISM-like applications) with some exclusions, HF 6.78 MHz (ITU-R ISM-Band 6.765-6.795 MHz), HF 13.56 MHz (ITU-R ISM-Band 13.553-13.567), and HF 27.12 MHz (ITU-R ISM-Band 26.957-27.283).

Figure 7:
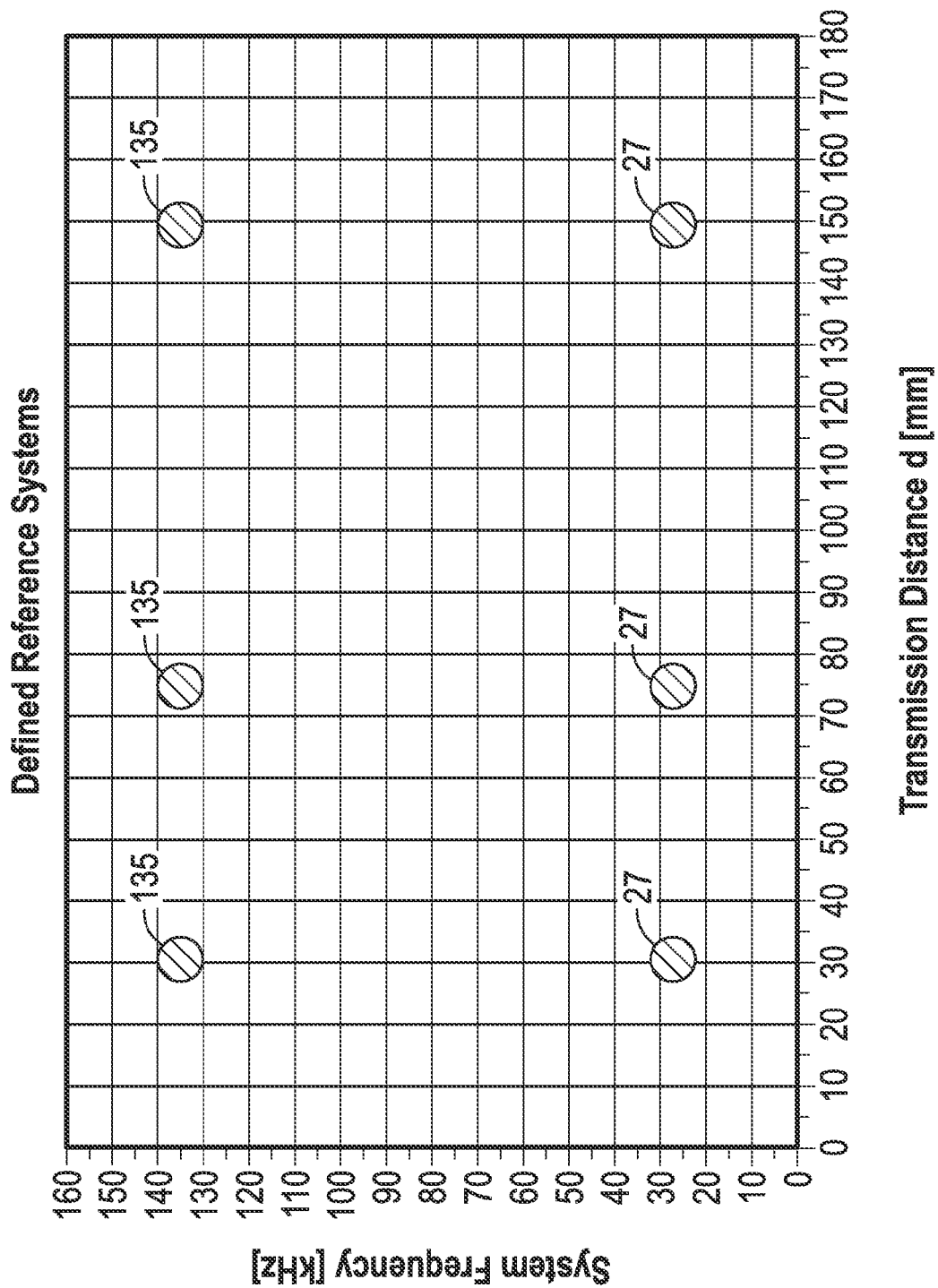
FIG. 7 is a chart showing exemplary frequencies and transmission distances that may be useful in wireless charging electric vehicles, in accordance with an exemplary embodiment.

FIG. 7 is a chart showing exemplary frequencies and transmission distances that may be useful in wireless charging electric vehicles, in accordance with an exemplary embodiment. Some example transmission distances that may be useful for electric vehicle wireless charging are about 30 mm, about 75 mm, and about 150 mm. Some exemplary frequencies may be about 27 kHz in the VLF band and about 135 kHz in the LF band.

Aspects of various embodiments described herein are directed to the detection of objects, for example, metal objects within specified region. Systems and methods for detection of metal objects as described herein may be incorporated into the systems described above for wireless power transfer. For example, embodiments for detection of objects as described below may be incorporated as a part of systems, such as those described above for inductive transfer of electrical energy from a primary structure to a secondary structure across an air gap. Exemplary frequencies for inductive transfer of energy may be in the range from 20 kHz to 150 kHz, but is not limited to this frequency range. More specifically, one application of the embodiments for detection of objects and methods described herein is inductive charging of stationary electric road vehicles and particularly embodiments where there is a magnetic structure (charging pad) on ground and a pick-up pad mounted at bottom side (underbody) of the vehicle. Other applications may be inductive powering or charging of electric vehicles on the move (dynamic charging), inductive charging of portable electrical and electronic devices, induction heating or any other systems generating strong alternating magnetic fields.

Moreover, while certain embodiments may be used in wireless power transfer systems, it should be appreciated that the various embodiments described herein may be applicable to other applications for detecting metal objects in a predetermined space unrelated to systems generating alternating magnetic fields. For example, aspects of embodiments described herein may be used in antitheft detectors for detecting metal objects that are removed from a predetermined space, security systems, quality assurance systems, electronic article surveillance, electronic article management, and the like.

The following acronyms may be used herein:
EMF Electro-Magnetic Field
FOD Foreign Object Detection
HF High Frequency
IF Intermediate frequency
LF Low Frequency
LMS Least Mean Square
MTBF Mean Time Between Failures
MUX Multiplexer
NCO Numerically Controlled Oscillator
PCB Printed Circuit Board
PSTN Public Switched Telephone Network
PWB Printed Wire Board
SNR Signal-to-Noise Ratio Certain descriptions of principles, methods and embodiments described herein refer to induction charging of electric vehicles (EV) or hybrid electric vehicles (HEV) and have to be regarded in this context. Some of the basic principles may be also useful for other applications as mentioned above. However, the embodiments may be modified and adapted to the specific requirements of these applications.

With respect to induction charging, depending on the energy transfer rate (power level), operating frequency, size and design of the primary and secondary magnetic structures and the distance between them, the flux density in the air gap at some locations may exceed 0.5 mT and may reach several Millitesla. If an object that includes a certain amount of well conductive material (e.g., metal) is inserted into the space between the primary and secondary structures, eddy currents are generated in this object (Lenz's law), that may lead to power dissipation and subsequent heating effects. This induction heating effect depends on the magnetic flux density, the frequency of the alternating magnetic field, the size, shape, orientation and conductivity of the object's conducting structure. When the object is exposed to the magnetic field for a sufficiently long time, it may heat up to temperatures that may be considered hazardous in regards to:

Self-ignition, if the object includes inflammable materials or if it is in direct contact with such materials e.g., a cigarette package including a thin metalized foil;
Burnings of the hand of a persons that may pick-up such a hot object e.g., a coin or a key; or
Damaging the plastic enclosure of the primary or secondary structure e.g., an object melting into the plastic.

A temperature increase may be also expected in objects including ferromagnetic materials that may be substantially non-conducting but exhibiting a pronounced hysteresis effect or in materials that generate both hysteresis and eddy current losses. As such, detecting such objects is beneficial to avoid corresponding harmful consequences. If the object detection system is integrated within a system for providing wireless power, in response to detecting a harmful object, the system may reduce a power level or shut down until measures may be taken to remove the harmful object.

In certain applications of inductive power transfer such as charging of electric vehicles in domestic and public zones, it may be compulsory for reasons of safety of persons and equipment to be able to detect foreign objects that have the potential to heat up to critical temperatures. This may be particularly true in systems where the critical space is open and accessible such that foreign objects may get accidentally or may be put intentionally into this space (e.g., in case of sabotage).

For example, the German VDE/DKE guideline for inductive charging of electric road vehicles (VDE-AR-E 2122-4-2 Elektrische Ausrüstung von Elektro-Straßenfahrzeugen—Induktive Ladung von Elektrofahrzeugen—Teil 4-2: Niedriger Leistungsbereich) (hereinafter "VDE-AR-E") e.g., defines protection limits for thermal effects in the functional space of an inductive charging system. These limits have been chosen following an international standard (IEC 60364-4-42:2010-05 "Low-voltage electrical installations—Part 4-42: Protection for safety—Protection against thermal effects") on low voltage electrical installations. The German guideline VDE-AR-E also defines reference objects to be used for compliance testing e.g., a € 5 cent coin and an aluminum coated foil.

Embodiments described herein are directed to automatically detecting hazardous foreign objects in the following (e.g., 'metal objects') that may be located in a pre-defined space. In particular, certain embodiments are directed to detecting small metal objects (e.g., a coin) located adjacent to a surface of the primary or secondary magnetic structure where magnetic flux density may exceed a particular value (e.g., 0.5 mT).

Metal detection has many applications in various industrial, military and security-related areas. Metal detectors are used e.g., for de-mining (detection of land mines), the detection of weapons such as knives and guns e.g., in airport security, geophysical prospecting, archaeology, and treasure hunting. Metal detectors are also used to detect foreign objects in food, and in the construction industry to detect steel reinforcing bars in concrete and pipes and wires buried in walls and floors.

In many applications, metal detectors achieve the required high sensitivity by frequently recalibrating their sensors and circuits. In these applications, presence of metal objects may be excluded during a process of recalibration based on user input. In contrast, high power induction charging application may have to operate largely automatically, autonomously and unattended by humans. As such, certain aspects of various embodiments are directed to object detection systems configured to provide inherent detection sensitivity and stability over years without the need for substantial recalibration.

Passive optical sensing (described in Conductix-Wampfler, Abschlussbericht zum Verbundvorhaben "Kabelloses Laden von Elektrofahrzeugen", im Rahmen des FuE-Programms "Förderung von Forschung and Entwicklung im Bereich der Elektromobilität", Weil am Rhein, Oktober 2011) (hereinafter "Conductix-Wampfler") using a camera sensitive in visible light and/or in shortwave infrared may be used to detect foreign objects in a predetermined area. Since 'metal objects' in general do not have peculiar characteristics in this wavelength range, this method may not provide sufficient selectivity, so that any foreign object will be detected including those that do not represent a hazard. This may be undesirable for users of the system in some cases. Moreover, optical sensors may not be particularly suitable in the harsh environment as expected beneath a vehicle, where there is normally strong pollution and risk of damage from mechanical impacts. Special protective measures such as automatic cleaning, etc. may be needed.

Active optical sensing of foreign objects by emitting light signals in the visible or short wave IR range may be provided. This technique is used in conjunction with 3D cameras based on time-of-flight ranging techniques described in Ringbeck, T, Hagebeuker, B. "A 3D time of flight camera for object detection", Optical 3-D Measurement Techniques, ETH Zürich, Plenary Session 1: Range Imaging I, 09-12 Jul. 2007 (hereinafter "Rinkbeck"). In some cases, using active optical sensing may not be able to resolve a small and thin object (e.g., a coin) sitting on the surface of an energy transfer pad. Furthermore, as with passive optical sensing, the method may not be able to distinguish metal objects from non-metal objects. Any object that appears opaque at optical wavelengths may be detected.

Since hazardous objects are those objects that have the potential for heating up to critical temperatures, thermal sensing described in Conductix-Wampfler is another approach ignoring environmental factors. One solution may be achieved by integrating temperature sensors into the enclosure of the energy transfer pads. To localize small hot objects, a high sensor density may be provided e.g., with a raster size of 30 mm. Since sensors need to be mechanically protected, they may be embedded in to the plastic enclosure at sufficient depth, which may decrease their sensitivity and increase their detection latency due to the heat propagation delay. Such approach may be slow and unreliable in regards to detecting objects with high risk of inflammation e.g., a thin metalized paper foil.

The use of pyro-electric passive infrared (PIR) sensors described in Conductix-Wampfler and described in WO 2011/006876 A2 (Wechlin M., Green, A. (Conductix-Wampfler AG), 'Device for the inductive transfer of electric energy') may provide an alternative thermal sensing solution. These sensors that are normally used for detecting persons by their motion are sensitive in the long-wave IR range where radiation spectral density becomes maximal for objects at temperatures below 100° C. (Wien's law). As the result of a trade-off between number of sensors per unit area and costs, a PIR sensor array may not provide adequate spatial resolution for detecting objects as small as 20 mm on a larger area such as an electric vehicle inductive charging pad. This may be particularly true if the temperature difference between a foreign object and the pad surface becomes low e.g., in case of pad heating by sun irradiation that may have happened before vehicle was parked for charging. Apart from the limited sensitivity, this solution may be vulnerable to pollution and mechanical impacts.

IR cameras described in Conductix-Wampfler based on bolometer focal arrays may provide sufficient resolution in the optimum wavelength range. However, they may be costly. This may be particularly true for rugged designs e.g., suitable for installation beneath a vehicle. Such cameras may require special protective measures such as a mechanical shutter that are closed if thermal detection is not used and the vehicle is on the move. Additionally, automatic cleaning of the IR lens protecting window using little wipers or similar concepts may be required. In addition, a vehicle bottom mounted camera may have an unfavorable angle of view for monitoring the entire critical space and the limited space for mounting the camera if a minimum ground clearance has to be respected. Customized ultra wide angle IR lenses may be needed if the camera is mounted close to the magnetic structures or high resolution (high number of pixels) if the camera is mounted in some distance where the scenery appears highly perspective and not well matched to a commercial-off-the-shelf bolometer array.

Acoustic sensing described in Conductix-Wampfler may be an alternative approach for detecting foreign objects. Acoustic sensing may be performed actively using radar principles by emitting ultrasonic signals and analyzing the received response. Ultrasonic frequencies e.g., above 200 kHz may provide sufficient resolution for detecting presence of a small and thin object e.g., a coin sitting on the surface of an energy transfer pad. However, all objects of a certain mass density may be detected thus prone to false alarms.

As opposed to ultrasonic radar, passive acoustic sensing described in Conductix-Wampfler has the potential for selectively detecting metal objects. When exposed to strong magnetic fields, electrically conductive objects begin to vibrate due to forces occurring between moving charges (currents) of the magnetic structure and of the foreign object (eddy currents). These forces can be explained by Lenz's law and Lorentz forces. These forces alternate at the first harmonic (double frequency) of the alternating magnetic field. For magnetic field frequencies above 20 kHz, these acoustic emissions may be above 40 kHz in the ultra-sonic range. Therefore, metal objects may be detected by their acoustic emissions at double frequency or even at harmonics thereof. Since the entire magnetic structure is vibrating at that frequency, high spatial resolution may be provided in order to detect presence of small objects. This may be achieved at ultrasonic frequencies using phased array technology requiring a high number of transducers. Because of induction heating and unacceptable eddy current losses, it may be difficult, in some cases, to integrate sensors into the pad's surface. Sensors may have to be arranged e.g., along the periphery of the vehicle pad as suggested in Conductix-Wampfler, a solution likely not providing sufficient resolution for reliably detecting small objects. As with the optical and IR sensors, ultrasonic transducers may be prone to pollution and damage from mechanical impacts.

Capacitive sensing described in Conductix-Wampfler is an approach based on electric field sensing. Capacitive sensing is used in touch screens. A capacitive sensor array may be accomplished e.g., using a thin open loop wire structure generating leakage electric fields. This wire structure may be embedded into the pad's plastic enclosure. As with optical sensing, capacitive sensing cannot provide selective detection of metals. Capacitive sensing may sense any object that changes an electric field thus a capacitance. This includes conductive materials and non-conductive dielectric materials e.g., little stones, wet leaves, etc.

In accordance with certain embodiments, inductive sensing based on magnetic fields may be preferably used since objects that can be sensed via the magnetic field may be objects that are potentially hazardous. Magnetic field sensing may be highly selective on electrically conductive and ferromagnetic objects. At frequencies e.g., below 20 MHz where a magnetic field may be considered quasi-stationary, there may be virtually no interaction with non-conductive dielectric objects and almost no interaction with badly conducting materials such as water with high salinity, or water-drenched paper, wet wood and foliage, etc.

In some cases, it may be somewhat difficult to detect small objects due to limited range. Smaller objects may be detected, in some cases, if they are in close proximity to a sensor. There may be locations in the space in which objects need to be detected, where smaller objects cannot be detected. This is particularly true if for reasons of mechanical protection and robustness, magnetic field sensors are integrated into the enclosure of an energy transfer pad.

WO 2011/006758A2 (Wechlin, M., Green, A. (Conductix-Wampfler AG), 'Device for the inductive transfer of electric energy') (hereinafter "Wechlin") discloses a device for detecting presence of metal object that is located within a predetermined space between a primary and secondary inductance. This has at least one unit for measuring inductance, a measuring unit for measuring the impedance of the measuring inductance and an evaluation unit that is connected to the measuring unit.

According to Wechlin, measuring inductance can be similar to the primary inductance, and the primary inductance is used for detecting a metal object. This may be applicable to solutions requiring less detection sensitivity e.g., for larger objects. To increase detection sensitivity e.g., for objects significantly smaller than the primary structure, the size of the measuring inductance may be reduced.

The sensing device of Wechlin may be equipped with a plurality of smaller measuring inductances, which form a regular two-dimensional arrangement extending approximately in one plane. The plane lies perpendicular to the main direction of the magnetic field that is generated by the primary inductance during operation. In regards to a lower cost and easier production, these measuring inductances may be planar coils on a common substrate (e.g., a multi-layer PCB). For achieving an increased coil packaging density (coils overlapping), Wechlin describes integration of a second coil array with an equal raster size but offset relative to the first array by one half of the raster size.

Wechlin also describes that measuring inductances are connected together forming groups and there is an impedance measuring unit per group. In another embodiment, Wechlin describes a common impedance measuring unit for the entire array. In this embodiment, the impedance measuring unit may be connected to single measuring inductances or groups of measuring inductances via an analog multiplexer (switch).

The evaluation unit as described in Wechlin compares measured impedance values with pre-stored reference values and provides outputs to indicate a deviation exceeding predetermined values. These outputs may be connected to a control unit and an indicator device to output an optical or acoustic alert signal. The control unit may also output a command to deactivate inductive energy transfer.

In Conductix-Wampfler, an alternative method for detecting electrically conductive or magnetizable objects is described. This method uses a number of measuring coils placed on top of the primary structure. In this method, detecting of metal objects or ferromagnetic objects is based on their effect of altering or perturbing the magnetic field as present at the surface of the primary structure. Conductix-Wampfler, describes measuring the voltage that is induced into each of the coils at inductive power transmission frequency. Conductix-Wamplfer also indicates that this method is sensitive to displacement in x and y likely but not explicitly referring to the displacement (alignment offset) of the secondary vs. the primary structure.

Conductix-Wampfler also describes another method called 'trafo'. The 'trafo' method uses capacitively loaded coils tuned to a frequency near 1 MHz forming a resonant transformer. Metal objects placed on the transformer coils change the field and thus the transmitted power.

Figure 8A:
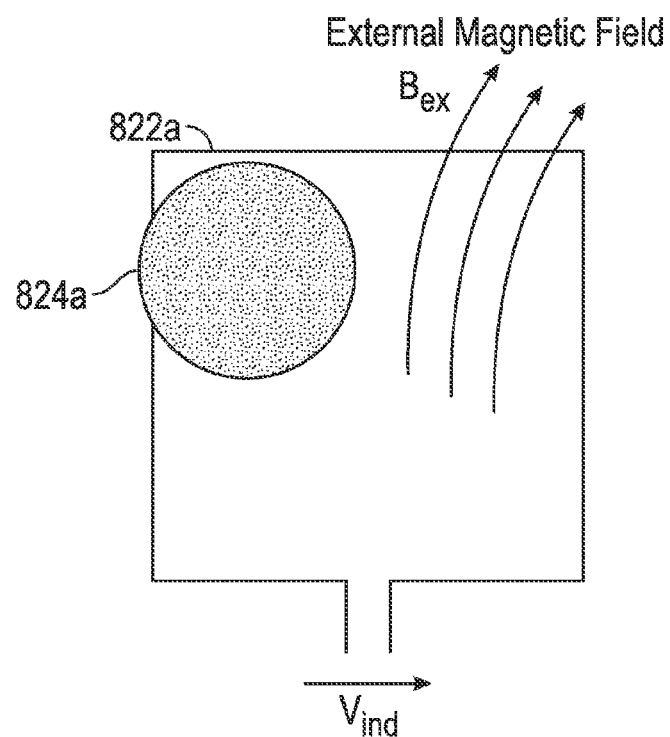
FIGS. 8A, 8B, and 8C are diagrams of portions of exemplary object detection circuitry, in accordance with exemplary embodiments.

FIG. 8A is a diagram of a portion of exemplary object detection circuitry configured to detect an object 824a via measuring the voltage induced into a sense loop 822a, in accordance with an embodiment. In accordance with various embodiments, the sense loop 822a may be a multi-turn loop (coil) e.g., for increasing sensitivity. Eddy currents in a metal object 824a placed in the proximity of the loop change the magnetic flux through the loop and thus the induced voltage. The magnetic field $B_{ex}$ is an external field that is generated for inductive energy transfer at an operating frequency. For example, the base system induction coil 104a may generate the magnetic field $B_{ex}$. The sense loop induced voltage in general changes in both amplitude and phase depending on the electric and magnetic properties of the object.

Figure 8B:
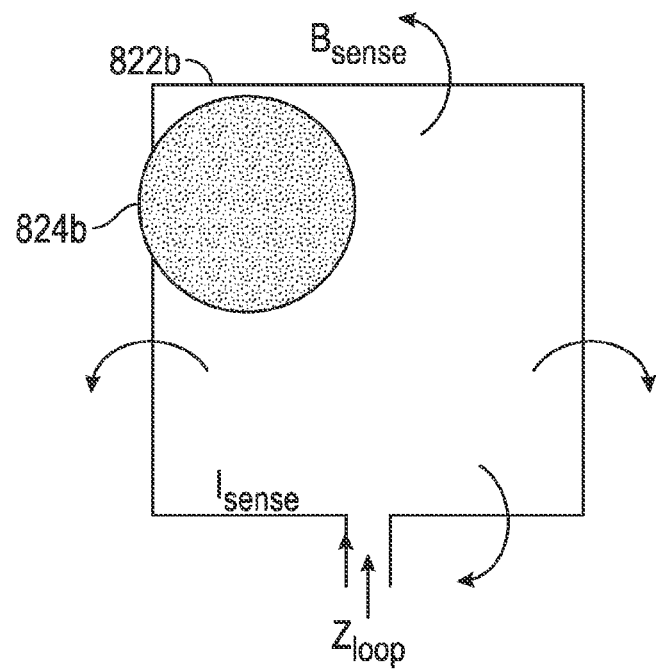

FIG. 8B is another diagram of a portion of exemplary object detection circuitry configured to detect an object 824b via measuring a sense loop impedance, in accordance with an embodiment. In general, a sense loop 822b may be a multi-turn loop (coil). To measure the loop impedance, a small high frequency sense current $I_{sense}$ is injected into the sense loop 822b. The metal object 824b in proximity of the loop modifies the magnetic flux as generated by the sense loop current $I_{sense}$ and thus modifies the loop's inductance and resistance (imaginary and real part of the impedance).

A frequency differing from the external magnetic field (e.g., another magnetic field provided for wireless energy transfer) may be used for impedance measurements in order to avoid interference from the fundamental or harmonics of the external magnetic field.

Figure 8C:
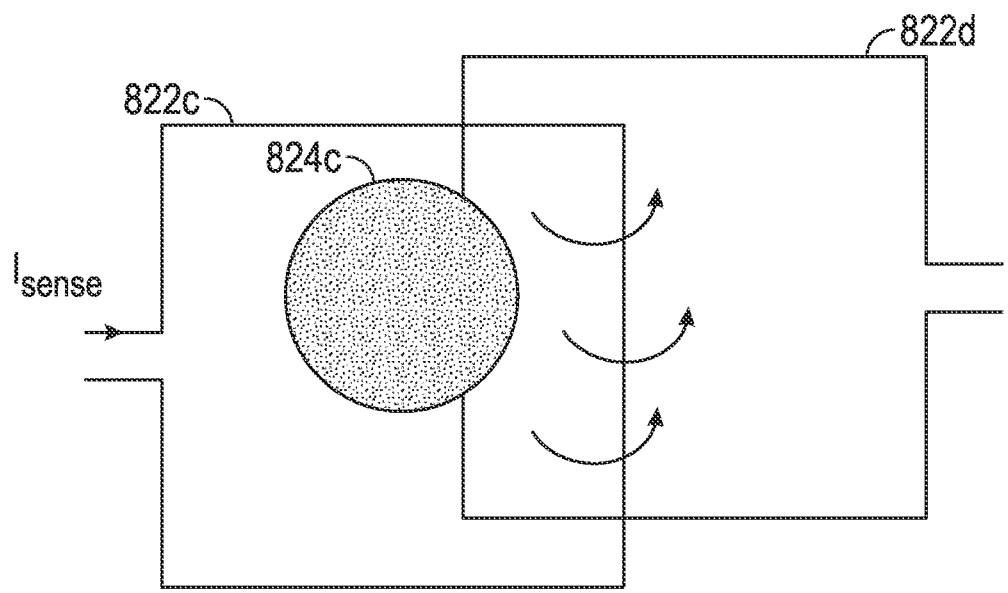

FIG. 8C is yet another diagram of a portion of exemplary object detection circuitry configured to detect an object 824c via measuring the coupling or the mutual impedance (mutual inductance) between a primary and a secondary sense loop structure 822c and 822d, in accordance with an embodiment. In general, the sense loops 822c and 822d may be multi-turn loops (coils). A change in mutual inductance or mutual impedance may be sensed by injecting a small high frequency current into the primary loop 822c and measuring the open circuit voltage at the secondary loop (amplitude and phase). Alternatively, the secondary loop may be resistively loaded and energy transfer into the load is measured. Here, the metal object modifies the magnetic flux that is generated by the primary loop current $I_{sense}$ and that is passing through the secondary loop, thus the mutual impedance that has an imaginary and a real part in general.

The mutual impedance method may also be understood as the loop induced voltage method however with the difference that the external magnetic field (e.g., as used for wireless power transfer) is supplanted by a magnetic field that is generated particularly for the purposes of metal detection by a dedicated primary sense loop 822c at a frequency differing from the frequency of the external magnetic field as used e.g., for energy transfer. The primary loop may cover the entire area or a substantial portion of the area to be protected.

Inductive Sensing

In accordance with certain aspects of certain embodiments, inductive sensing or magnetic field sensing may provide several benefits, for example:

Inductive sensing may be highly selective on well conducting (metallic) objects

No impairments by other non-metallic (dielectric) objects are expected;

Inductive sensing circuitry may be integrated into the plastic enclosure of an energy transfer pad to protect sensors from environmental impacts (pollution, mechanical) with minor performance degradation; and Inductive sensing circuitry may be incorporated into the charging base since in most cases objects may be laying on the base pad surface. This may allow for cost savings in the vehicle onboard equipment.

Methods and Concepts to Enhance Inductive Sensing

As stated above, large loops may not provide sufficiently high sensitivity as needed for detecting a coin, a key, or a lid of a beverage can, which may be significantly smaller than the area to be protected. In accordance with various embodiment, for detecting small objects, a plurality of smaller loops may be used according to various embodiments.

Figure 9:
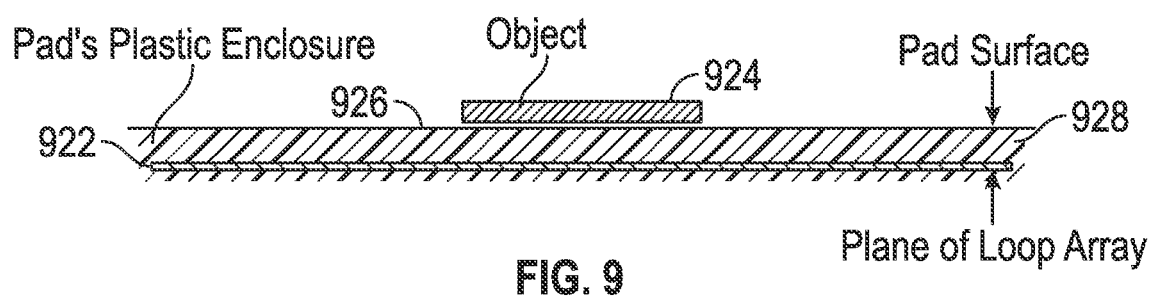
FIG. 9 is a side view of a sense loop configured to detect an object embedded within a magnetic pad, in accordance with an embodiment.

FIG. 9 is a side view of a sense loop 922 embedded within a wireless charging pad 926, the sense loop 922 configured to detect an object 924, in accordance with an exemplary embodiment. The pad has a plastic enclosure 928 and may be configured to hold a planar sense loop 922 and detect an object placed anywhere on the surface of the pad 926. The charging pad 926 may further include a base system induction coil 104*a* (FIG. 1) and associated circuitry as described above with reference to FIGS. 1-3 and may be configured to detect an object on the pad 926. Further examples of pad configurations are shown in FIGS. 5A-5D.

The innate sensitivity of a sensor may be defined as the percentage change of the measured quantity (e.g., loop induced voltage, loop impedance) as caused by the presence of the smallest object (reference object) if placed at a worst case position. The overall sensitivity of a foreign object detector depends on the innate sensitivity of the sensor and on the performance of additional post processing methods that may be part e.g., of the evaluation unit.

For objects smaller than the loop size, the innate sensitivity increases with decreasing loop size. Decreasing loop size implies increasing the number of loops required to cover a given area resulting in increased complexity and costs and higher probability of false alarm and failure.

In accordance with certain embodiments, an adequate trade-off between innate sensitivity and circuit complexity may be achieved with a loop raster size of equal or double the size of the smallest object to be detected. For example, if the smallest object is a coin of 20 mm diameter, an adequate loop raster size may be 30 mm. This may be for both the loop induced voltage method and the loop impedance method.

Figure 10:
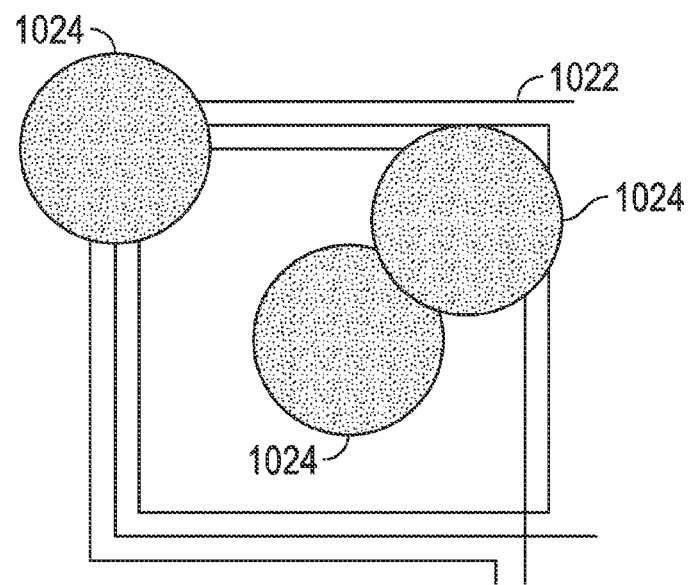
FIG. 10 is a diagram of a portion of exemplary object detection circuitry for detecting an object located at different positions relative to a sense loop, in accordance with an exemplary embodiment.

FIG. 10 is a diagram of a portion of exemplary object detection circuitry for detecting an object 1024 located at different positions relative to a sense loop 1022, in accordance with an exemplary embodiment. As an example, FIG. 10 may illustrate changes of loop induced voltage at 40 kHz in percent using a coin 1024 (e.g., of diameter 25 mm and thickness 1.7 mm) placed at different positions on a rectangular wire loop 1022. The loop may be made of 3 turns of thin enamel copper wire. The coin may be placed at a height above the loop structure in regards to a possible future integration of the loop array into a plastic enclosure 928 of a magnetic pad 926 as shown in FIG. 9. For example, when the object 1024 is placed in the upper left corner of the sense loop 1022, a change in percent of loop induced voltage may be on the order of, for example, negative six percent. When the object 1024 is placed in the center of the sense loop 1022, a change in percent of loop induced voltage may be on the order of, for example, negative twenty-two percent. When the object 1024 is placed towards the upper right corner of the sense loop 1022, a change in percent of loop induced voltage may be on the order of for example, negative fifteen percent. These values are provided to illustrate relative degrees of changes in percent of loop induced voltage when an object 1024 is located in different positions and are merely exemplary.

Likewise, changes in loop impedance may also be provided for different positions for the configuration shown in FIG. 10. For the object 1024, measured impedance changes are changes due substantially to its changing inductance. For example, when the object 1024 is placed in the upper left corner of the sense loop 1022, a change in percent of loop impedance may be on the order of, for example, negative two percent. When the object 1024 is placed in the center of the sense loop 1022, a change in percent of loop impedance may be on the order of, for example, negative eight percent. When the object 1024 is placed towards the upper right corner of the sense loop 1022, a change in percent of loop impedance may be on the order of for example, negative five percent. These values are provided to illustrate relative degrees of changes in percent of impedance when an object 1024 is located in different positions and are merely exemplary.

Though showing higher innate sensitivity, the induction loop method may need to cope with significant changes of the magnetic field as caused by the varying position (offset and distance) of the adjacent magnetic pad, the vehicle's underbody structure or a conductive ground. These effects may need to be taken into account.

On the other hand, the loop impedance method exhibits lower innate sensitivity, but may also be less sensitive on changes in its metallic and ferromagnetic environment. As opposed to the induction loop method, its sensitivity may slightly degrade if measured via the connecting lead. Depending on the size of the loop array and the location of the impedance analyzer, a possible worst-case lead length may be 1 m, assuming the impedance analyzer is integrated into the magnetic pad 926.

For both methods, the object 924 may have the strongest impact if placed in the center of the loop 922 and weakest impact if placed on an edge and particularly in the corner. It shall be noticed however that for 'edge' and 'corner' position, impedance/induced voltage may also change in adjacent loops, assuming an array of loops. Simultaneous changes in adjacent loops can be exploited in post processing to improve overall detection sensitivity in accordance with various embodiments.

Shape, Orientation and Packing of Sense Loops

Figure 11A:
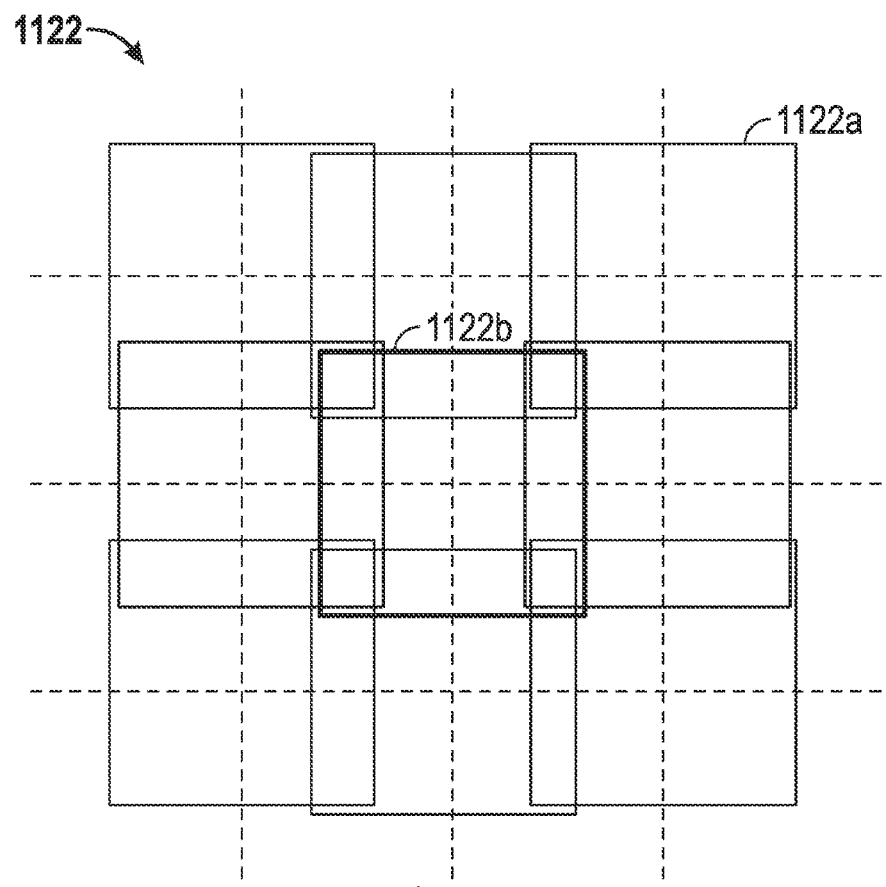
FIGS. 11A, 11B, and 11C are diagrams of different exemplary configurations for sense loops configured to detect an object, in accordance with exemplary embodiments.
Figure 11B:
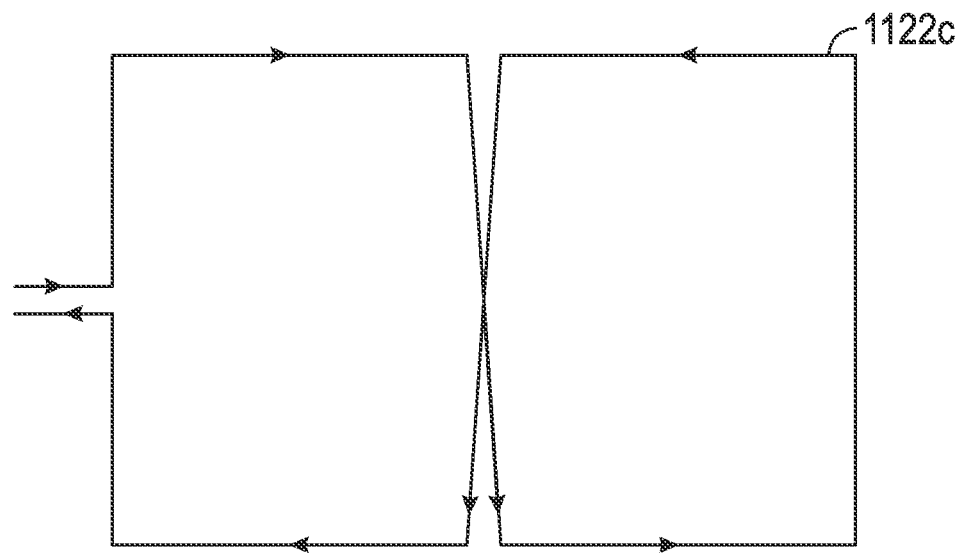
Figure 11C:
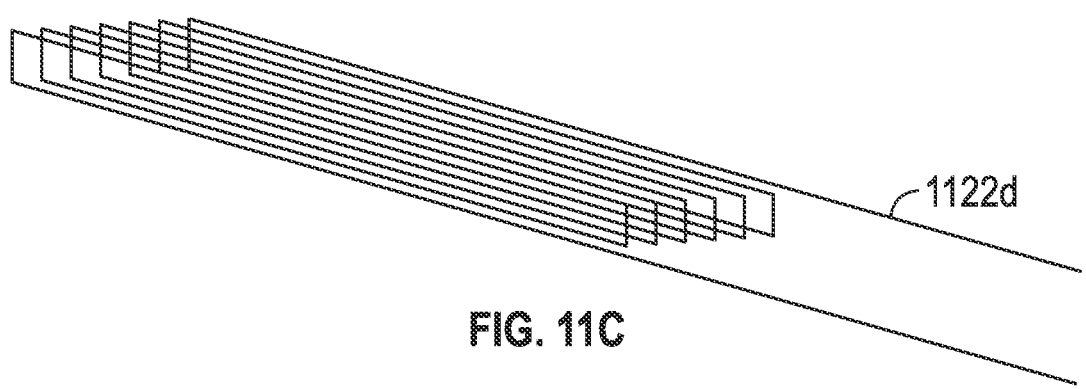

FIGS. 11A, 11B, and 11C are diagrams of different exemplary configurations for sense loops configured to detect an object, in accordance with exemplary embodiments. Using an array 1122 of overlapping loops 1122*a* and 1122*b* as illustrated in, for example as shown in FIG. 11A, may improve innate sensitivity of an inductive sensor system. In this arrangement, loops 1122*a* and 1122*b* are somewhat larger than the raster size of the array. Overlapping the loops as shown in FIG. 11A improves worst case sensitivity at the expense of the best case sensitivity (coin centered in the loop). Overlapping reduces the sensitivity ripple on a sense loop array 1122. For an embodiment using a printed circuit board, overlapping in rows and columns may use, for example, at least 4 copper layers.

Innate sensitivity variations may be equalized by dimensioning the loops slightly larger than the raster size equally in both x and y direction. A ratio of overlapping area to non-overlapping area may be in the range from 0.5 to 2 that may provide various benefits.

Instead of using a square or a rectangular shape, loops 1122*a* and 1122*b* may be circular-, hexagonal-, triangular-shaped in accordance with various embodiments. In a loop array 1122, densely packed hexagonal loops may provide improved sensitivity with a non-overlapping structure requiring a lower number of copper layers when implemented in a printed circuit board.

Moreover, the loop's size, shape or raster size may be adapted to local sensitivity requirements. On a surface with local variations of the magnetic flux density e.g., there may exist areas/zones with lower potential for thermal effects thus relaxed sensitivity requirements. Larger loops may be placed in these less critical areas, trading-off sensitivity, wiring and circuit complexity.

For the loop impedance measuring method, other loop topologies such as double loops as shown in FIG. 11B, triple loops (clover leave), or even quadruple loops, producing a magnetic flux arch from one pole area to another pole area when driven by a sense current. FIG. 11B shows a topology for a double loop 1122c showing sense current directions. These structures may be used for an optimized detection performance e.g., in applications where a predominant horizontal field component was useful for detecting metal objects.

Combinations of structures generating differently oriented magnetic fields (e.g., double loop plus single loop) generates a rotating magnetic vector field if driven with 90° phase offset. The use of such circular or elliptically polarized fields may also lead to improved detection performance in certain applications.

In accordance with an embodiment, innate sensitivity of the loop induced voltage method may be considerably increased by using wire loops 922 in a plane that is substantially parallel to the magnetic field lines such that there is virtually zero flux passing through the loops. For its integration into the enclosure of a charging pad 926, low profile solenoid coils 1122 as illustrated in FIG. 11C where the solenoid coils 1122 may be in a plane substantially parallel to the direction of the magnetic field.

Even a small metal object may dramatically raise the flux through the loop as it changes the direction of the magnetic field lines. The phase of the loop induced voltage in this case generally is offset relative to the external magnetic field. As already stated above, this phase offset depends on the electric and magnetic properties of the object. A conductive object produces a different phase shift than a ferromagnetic object.

An increased flux and a phase shift may however also be experienced if magnetic pads are displaced or pad currents change. Resonant inductive energy transfer is characterized by a 90 degrees phase shift between primary and secondary current. This may also cause a phase shift in the sensed voltage.

In accordance with some embodiments, using an orthogonal loop system (loops substantially in perpendicular planes e.g., a planar coil and a solenoid) may also enhance sensitivity of the loop induced voltage method. Since metal objects may generally change the direction of the magnetic field in their surroundings, sensing flux components by an orthogonal loop arrangement may provide additional information to improve the detector's performance.

Moreover, the induction balance using a pair of loops e.g., in a double 'D' arrangement is a technique implemented in metal detectors e.g., as used for detection of mines. Balance is maintained by continuously running a calibration process. A foreign object may slightly change the flux passing through the two coils. This change in general may be unequal in the two loops thus temporarily unbalancing the bridge. This method may be sensitive to situations where the magnetic field may be changing due to other factors.

An inductive balance may be also accomplished based on the loop impedance of FIG. 8A or the mutual impedance method using two coupled loops of FIG. 8C. For the latter, loops 822c and 822d may be positioned in a manner such that flux generated by the primary loop 822c virtually or substantially cancels out in the secondary loop 822d (zero coupling). When an object is placed in the sensitive area of these loops 822c and 822d, it unbalances flux through the secondary thus dramatically increasing coupling. The pad's magnetic structure may also unbalance the system. Even if these effects were taken into account in the printed circuit board layout, the solution may be extremely sensitive on fabrication tolerances.

To avoid excessive heating and consecutive damage of the PWB in the unlikely event of a short circuit in a sense loop, the loops may be fused. A fuse may be accomplished by design using thin wire or thin PWB traces or if electric resistance increase is not permissible by inserting a diminution in the PWB traces at defined locations.

A Method for Enhancing the Magnetic Field Sensing

Figure 12:
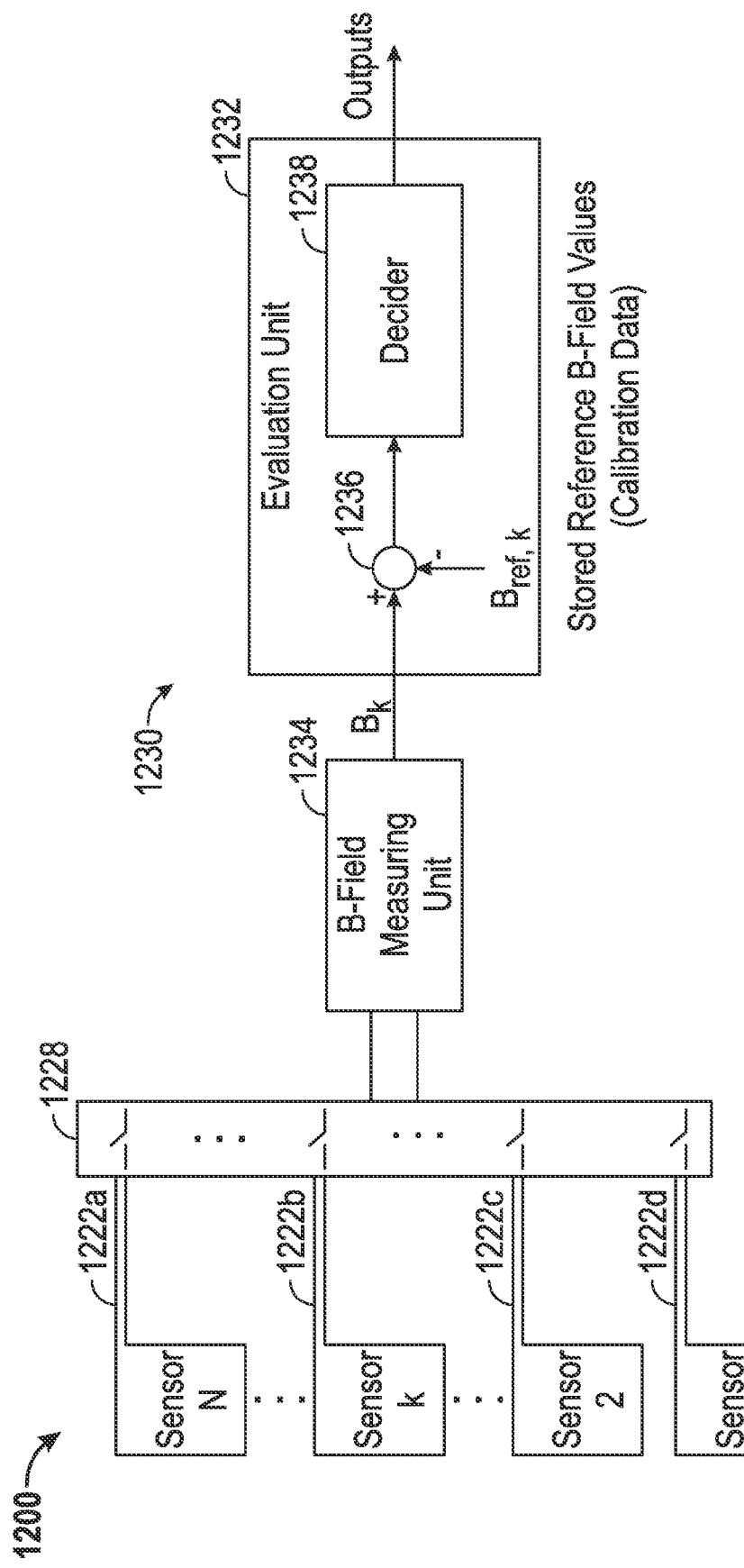
FIG. 12 is a functional block diagram of an exemplary circuit configured to detect an object based on magnetic field sensing, in accordance with exemplary embodiments.

FIG. 12 is a functional block diagram of an exemplary circuit 1200 configured to detect an object based on magnetic field sensing, in accordance with exemplary embodiments. This section describes an embodiment for enhancing performance of a metal object detector that is based on sensing a magnetic field (flux density) as generated by a magnetic structure e.g., a charging pad 926 over a predetermined area. The charging pad 926 may correspond to a charging system as described above with reference to FIGS. 1-3. The circuit 1200 may include several sense loops 1222a, 1222b, 1222c, and 1222d (referred to herein after collectively as sense loops 1222). The sense loops 1222 may form a part of an array of densely packed loops that cover an area to be protected in which metal objects may be detected. As described above, detecting an object 924 may be accomplished by measuring the voltage induced into the sense loops 1222. The circuit 1200 includes a detection circuit 1230 that selectively couples to each of the sense loops 1222 via a multiplexer 1228. The detection circuit 1230 includes a magnetic field measuring unit 1234 configured to measure a magnetic field strength of each of the sense loops 1222. A measured value of the sense loop $B_k$ is provided to an evaluation unit 1232 including a comparator 1236 and a decider 1238. The comparator receives the measured magnetic field value $B_k$ and compares the value $B_k$ with a reference magnetic field value $B_{ref,k}$. The reference magnetic field value may correspond to an expected value of the magnetic field for a sense loop 1222a in the absence of any object to be detected. Based on the output of the comparator 1236, the decider 1238 is configured to determine whether an object is present. For example, the decider 1238 may determine that the difference between the measured value $B_k$ and the reference value is greater than a threshold and output a signal that an object is detected in response. The decider 1238 may further compensate the output of the comparator based on known operating characteristics that may impact the result to increase.

Alternatively, with respect to the circuit in FIG. 12, an array of Hall effect sensors or sensors may be used that are based on the Giant Magnetic Resistance (GMR) effect or any other method suitable to sense a magnetic field.

It may be also useful to sense at least one of an x-component, y-component, and z-component of the magnetic field vector separately.

Embodiments according to the circuit of FIG. 12 may be useful in use cases where there is a magnetic field on the base pad surface that is subject to temporal changes (perturbations, distortions) e.g., due to the presence of the vehicle pick-up pad and the vehicle's metallic underbody structure that may be at different vertical and horizontal positions (different alignment offsets). Evaluation may be based on a least mean square error criterion and may be implemented into the detector's evaluation unit 1232. Other more sophisticated methods using other error metrics and iterative processes e.g., RANSAC (Random Sample Consensus method) may also be used.

An exemplary process for detecting an object may be formulated as follows:

Find a small metal object that excerpts a little impact (distortion, perturbation, disturbance) on the magnetic field pattern as present on a magnetic charging pad's surface. This field pattern may exhibit strong variations in flux density due to an inhomogeneous magnetic structure (coil, ferrites) and additionally temporary variations (distortions) due to the different positions of the vehicle pad and the vehicle's metallic underbody structure. For example, there may be significant field distortion and other impact from pad alignment offset.

However, the impact on the magnetic field on a surface of a pad 936 exerted by a small metal object (e.g., a coin particularly if placed in the order of four adjacent loops where innate sensitivity per loop is lower) may be small in comparison to field distortions due to alignment offsets. In such as case, an impact on a magnetic flux density pattern may be small.

The impact of the object 924 however may be made visible by subtracting the field pattern as measured in absence of the object 924 (the reference field pattern) from the field pattern measured in presence of the object.

In some cases, it may be difficult if the object 924 has to be detected in a magnetic field pattern that is distorted relative to the reference pattern. The reference pattern may be taken and stored in the system as part of a calibration procedure in zero offset conditions and at a defined air gap distance. The object however may have to be detected in different conditions as resulting in realistic use cases. The method of computing the differential field patter may not be sufficient in some cases due to errors due to the field distortion in offset conditions may be far greater than the impact of the object requiring a more sophisticated methods.

As such, in accordance with an embodiment, an improved detection method may be based on a least mean square approach as follows:

DEFINITIONS $B_{ref}(x_i, y_j)$: Reference flux density values (reference field pattern extending in x- and y-direction) e.g., as stored in foreign object detection system and obtained by calibration in predetermined conditions at production in factory $\tilde{B}(x_i, y_j)$: Actual flux density values (distorted field pattern) as measured in a realistic scenario e.g., in presence of offsets and different air gap distance $\gamma(x_i, y_j; a_1, a_2, \ldots, a_L)$: a correction function with multiple parameters compensating for the distortion effect in the actual field pattern. In the simplest case, this function may be a plane whose z-offset and x- and y-slope can be modified by parameters $a_1, a_2, a_3$.

The method may include computing mean square error in differential field values as resulting after applying correction function to the actually measured field values and subtracting the reference flux density values $$\overline{\epsilon^2}(a_1, a_2, \ldots, a_L) = \sum_{i=0}^{N} \sum_{j=0}^{M} [\tilde{B}(x_i, y_j)\gamma(x_i, y_j; a_1, a_2, \ldots, a_L) - B_{ref}(x_i, y_j)]^2$$

In addition, a method may include determining optimum values for parameter set $a_1, a_2, a_L$, minimizing the mean square error $$a_{1\_opt}, a_{2\_opt}, \ldots, a_{L\_opt} \rightarrow \min_{a_1, a_2, \ldots, a_L} \overline{\epsilon^2}$$

The method further includes applying a correction function with optimum parameters to measured field pattern and perform object detection on the resulting LMS differential pattern $$\Delta B(x_i, y_j) = \tilde{B}(x_i, y_j)\gamma(x_i, y_j; a_{1\_opt}, a_{2\_opt}, \ldots, a_{L\_opt}) - B_{ref}(x_i, y_j)$$

The following decision rule may apply:
Hypothesis 'Object present', if at least one differential flux density value exceeds a predefined threshold.
Hypothesis: 'No object', else.

This method may be significantly improved by using a set of reference patterns instead of a single reference pattern $B_{ref}(x_i, y_j)$. These reference patterns may have been obtained in different offset and air gap conditions as part of a calibration procedure performed at factory. The reference pattern that results in the least mean square error is chosen to compute the differential field pattern.

The least mean square method may not perform in the expected way in presence of a large metal object. Since such large objects may easily be recognized, the leas mean square method may be conditionally used or adapted accordingly.

Alternative Concepts for Enhancing the Loop Impedance Sensing Method

Several methods and embodiments are further described herein that improve performance and/or reduce wiring and circuit complexity of a loop impedance based metal object detector. These are in particular:

Using an array of resonant loops and measuring their resonant frequency to sense a metal object Using weakly coupled resonant loops e.g., using either inductive or capacitive coupling.

Figure 13:
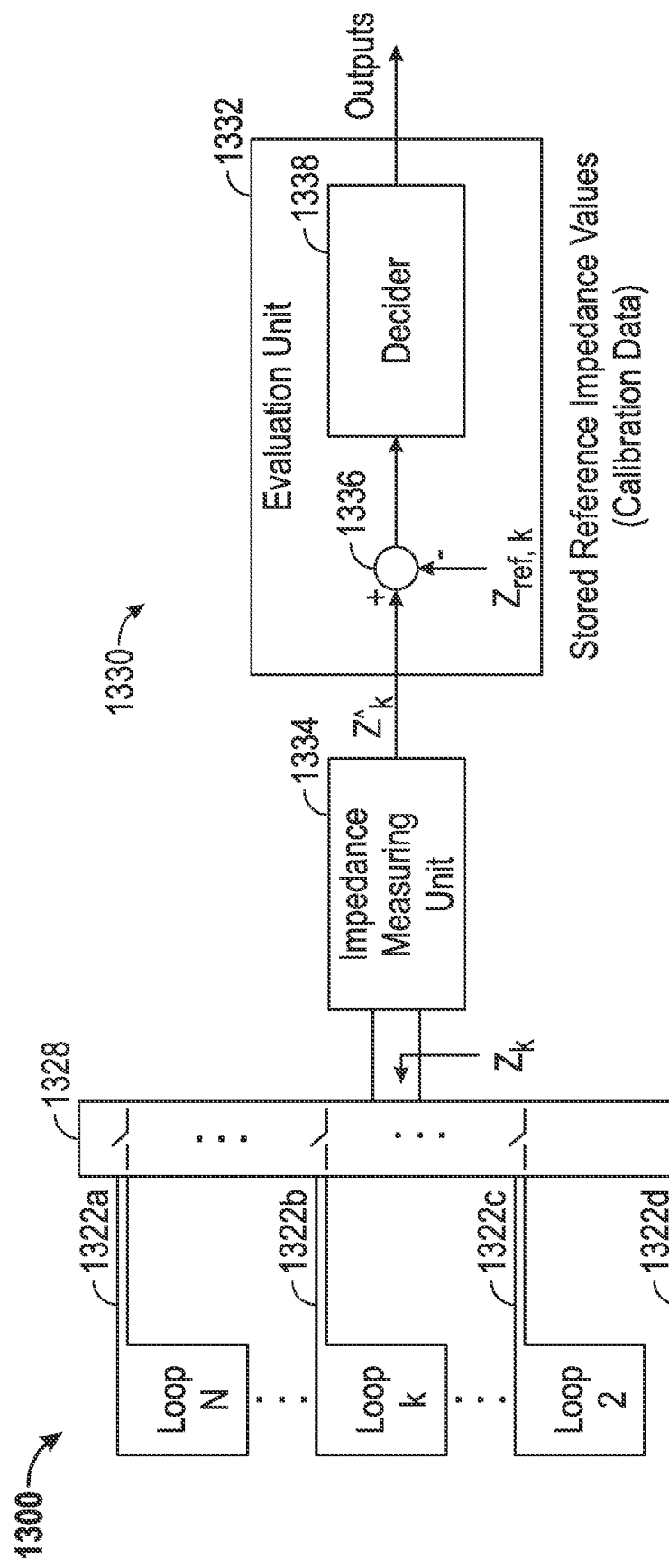
FIG. 13 is a functional block diagram of an exemplary circuit configured to detect an object based on sense loop impedance measurements, in accordance with exemplary embodiments.

Using canonical structures of inductively or capacitively coupled resonant loops forming a coupled resonator filter acting as a signal propagation medium Resonant Loops and Measuring their Resonant Frequency FIG. 13 is a functional block diagram of an exemplary circuit 1300 configured to detect an object based on sense loop impedance measurements, in accordance with exemplary embodiments. The circuit 1300 may include several sense loops 1322a, 1322b, 1322c, and 1322d (referred to herein after collectively as sense loops 1322). The sense loops 1322 may form a part of an array of densely packed wire loops that cover an area to be protected in which metal objects may be detected. The circuit 1300 includes a detection circuit 1330 that selectively couples to each of the sense loops 1322 via a multiplexer 1328. The detection circuit 1330 includes an impedance measuring unit 1334. Impedance $Z_k$ at the multiplexer port is measured for each loop 1322 selected by the multiplexer 1328 sequentially and periodically via the impedance measuring unit 1334. A measured value of the sense loop $B_k$ is provided to an evaluation unit 1332 including a comparator 1336 and a decider 1338. An object 924 is detected based on the differential impedance as resulting by subtracting a reference impedance value $Z_{ref,k}$ from the measured impedance value $Z^\wedge_k$ for k=1 ... N as shown by the comparator 1336. A decider unit 1338 receives input from the comparator 1336 and determines whether an object is detected. For example, if the difference between a measured value and the reference value exceeds a threshold and may incorporate any of the functionality as described above, for example, with reference to the least mean square method.

Figure 14A:
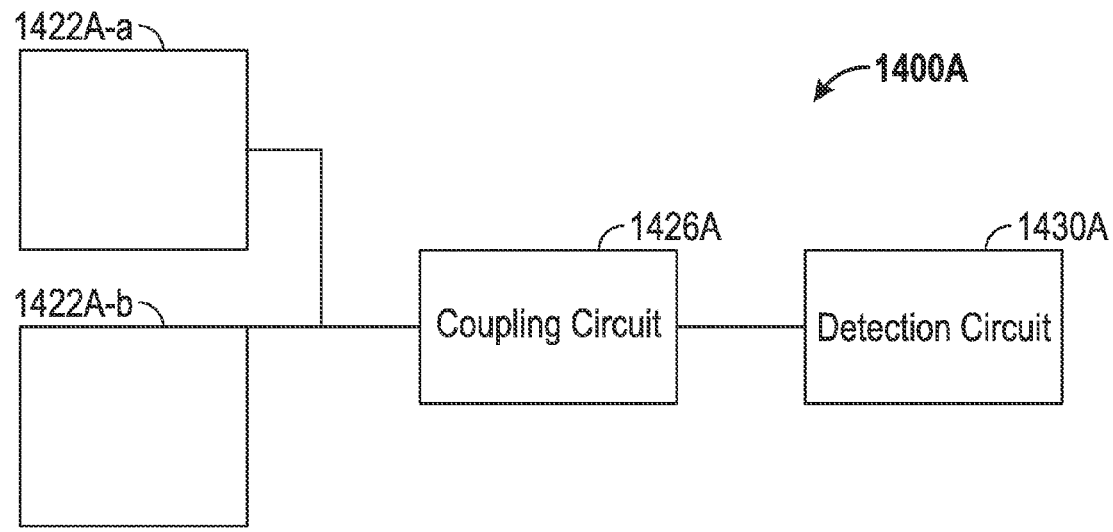
FIG. 14A is a functional block diagram of an exemplary circuit configured to detect an object based on sense loop resonant frequency measurements, in accordance with exemplary embodiments.

FIG. 14A is a functional block diagram of an exemplary circuit 1400A configured to detect an object 924 based on sense loop resonant frequency measurements, in accordance with an embodiment. The circuit 1400A may be configured to detect an object 924 based on measuring a loop impedance to determine a resonant frequency. The circuit 1400A includes sense loops 1422A-a and 1422A-b. The sense loops may have an inductance L. As used herein, a sense loop 1422A-a may be referred to as or be configured as a sense circuit. The sense loops 1422A-a and 1422A-b are coupled to a detection circuit 1430A via a coupling circuit 1426A. Some combination of the coupling circuit 1426A and the sense loops 1422A-a and 1422A-b form resonant circuits. For example, in an embodiment, the sense loops 1422A-a and 1422A-b include reactive components (e.g., a capacitor) to form resonant circuits configured to resonate at a particular frequency. In another embodiment, the coupling circuit 1426A includes reactive components electrically coupled to each of the sense loops 1422A-a and 1422A-b to form resonant circuits configured to resonate at a particular frequency. Either series or parallel tuning may be used. Exemplary embodiments for configuration of the resonant circuits are described below. In some embodiments, the frequencies of the resonant circuits formed at least by each sense loop 1422A-a and 1422A-b may be the same while in some embodiments they may be different. The coupling circuit 1426A may include a multiplexer to selectively couple each of the sense loops 1422A-a and 1422A-b to the detection circuit 1430A. The coupling circuit 1426 is configured to reduce a variation of the resonant frequencies of the sense loops 1422A-a and 1422A-b by the detection circuit 1430A in the absence of an object.

The detection circuit 1426A is configured to detect objects based on the change of the resonant frequency of each sense loop 1422a and 1422b relative to a reference/calibration value e.g., stored in a look up table as part of the system. For example, the detection circuit 1426A may be configured to measure first and second characteristics that depend on the first and second resonant frequencies of the sense loops 1422A-a and 1422A-b, respectively. The detection circuit 1426A is configured to detect presence of an object in response to detecting a difference between the first measured characteristic and a corresponding characteristic that depends on the first resonant frequency or a difference between the second characteristic and a corresponding characteristics that depends on the second resonant frequency. The characteristic may be a measured resonant frequency, a quality factor, or other characteristic from which a frequency at which a sense loop 1422A-a is resonating is determined. Furthermore, the use of multiple sense loops 1422A-a and 1422A-b may allow for the detection circuit to detect a position of the object 924 relative to at least one of the sense loops 1422A-a and 1422A-b. The sense loops 1422A-a and 1422A-b may be a part of an array of densely packed sense loops arranged in a planar form to cover an area, for example of a wireless charging pad 936 to be protected. Each of the sense loops including sense loops 1422A-a and 1422A-b may be selectively coupled to the detection circuit 1430A and allow for determining position information of an object 924 to be detected in a pre-determined space.

Figure 14B:
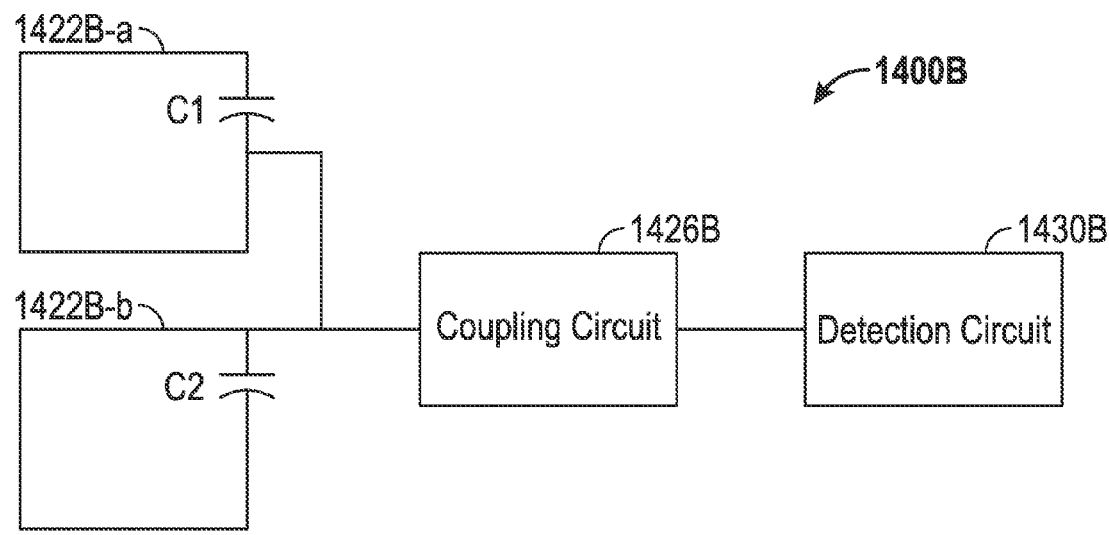
FIG. 14B is a functional block diagram of an exemplary circuit configured to detect an object based on sense loop resonant frequency measurements, in accordance with an embodiment.

FIG. 14B is a functional block diagram of an exemplary circuit 1400B configured to detect an object 924 based on sense loop resonant frequency measurements, in accordance with an embodiment. The circuit 1400B includes sense loops 1422B-a and 1422B-b. The sense loops may have an inductance L. As compared to FIG. 14A, the sense loops 1422B-a and 1422B-b include reactive components such as capacitors C1 and C2 such that each sense loop 1422B-a and 1422B-b forms a resonant circuit. Either series or parallel tuning may be used. The sense loops 1422B-a and 1422B-b are coupled to a detection circuit 1430B via a coupling circuit 1426B. The coupling circuit 1426B may not form a part of a resonant circuit in accordance with the embodiment shown in FIG. 14B. In some embodiments, the frequencies of the resonant circuits formed at least by each sense loop 1422B-a and 1422B-b may be the same while in some embodiments they may be different. The coupling circuit 1426B is configured to reduce a variation of the resonant frequencies of the sense loops 1422B-a and 1422B-b by the detection circuit 1430B in the absence of an object. The detection circuit 1430B may function similarly as the detection circuit 1430A of FIG. 14A.

To measure the loop impedance and particularly the resonant frequency, a frequency significantly higher than that of the alternating magnetic field used for wirelessly transferring power, preferably in the Megahertz range may be used. The sense frequency however may not be too high e.g., <20 MHz if sensitivity on dielectric objects has to be kept low.

Figure 15:
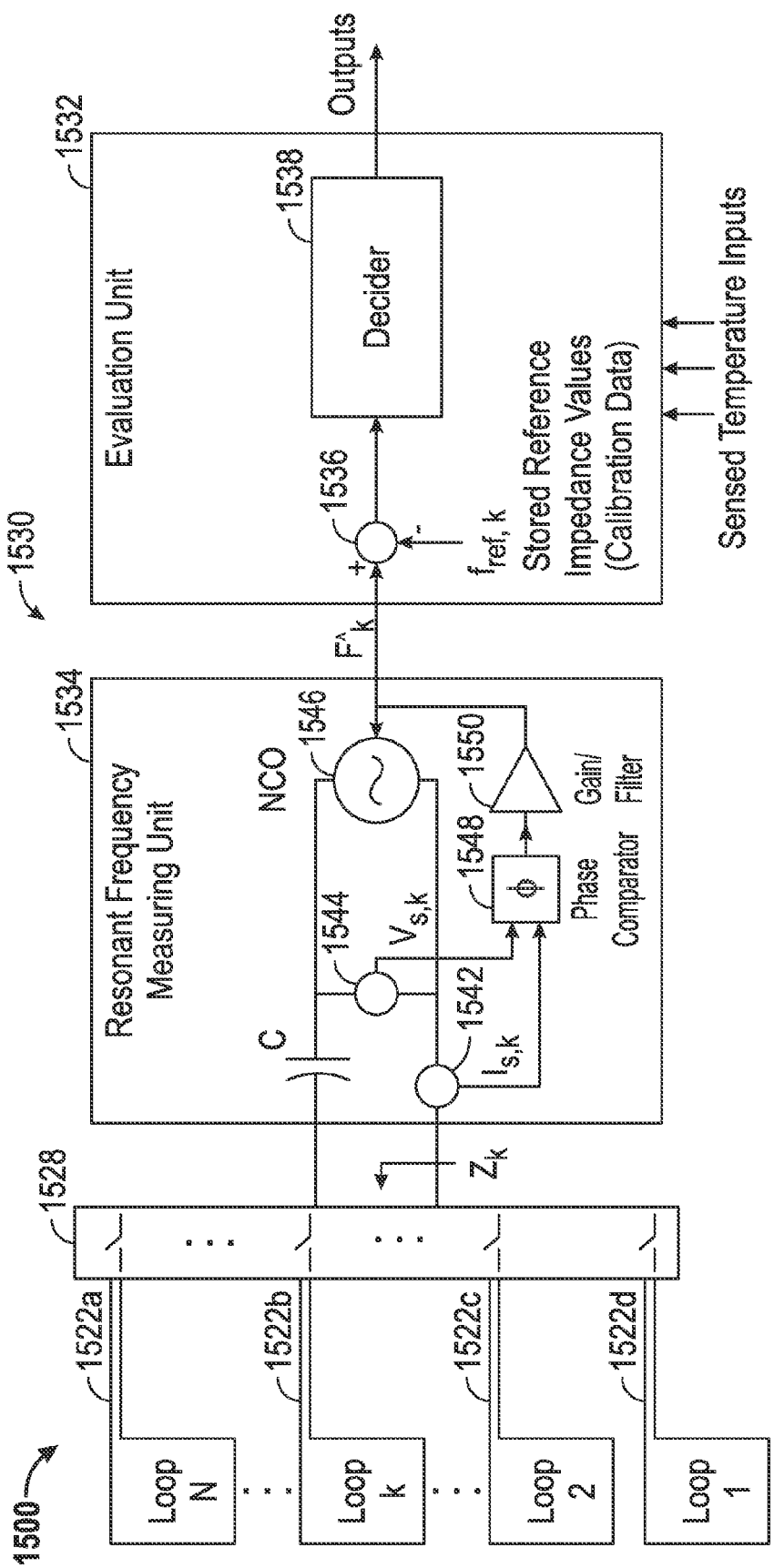
FIG. 15 is another functional block diagram of an exemplary circuit configured to detect an object based on sense loop resonant frequency measurements, in accordance with exemplary embodiments.

FIG. 15 is another functional block diagram of an exemplary circuit 1500 configured to detect an object 924 based on sense loop resonant frequency measurements, in accordance with an exemplary embodiment. The circuit includes sense loops 1522a, 1522b, 1522c and 1522d (hereinafter referred to collectively as sense loops 1522) that may be part of an array of sense loops. In some embodiments, the sense loops 1522 may substantially be configured to define a common plane over a predetermined area to be protected. The sense loops 1522 are coupled to a detection circuit 1530 via a multiplexer 1528 configured to selectively couple each of the sense loops 1522 to the detection circuit 1530 including a resonant frequency measuring unit 1534 and an evaluation unit 1532. The resonant frequency measuring unit 1534 includes a capacitor C such that a sense loop 1522a coupled to the resonant frequency measuring unit 1534 forms a resonant circuit configured to resonant a particular resonant frequency. It is noted that with reference to FIG. 14A, a coupling circuit 1426A may include the multiplexer 1528 and the resonant frequency measuring unit 1534 including capacitor C shared by all sense loops 1522 to form each resonant circuit. The resonant frequency measuring unit 1534 includes an oscillator 1546 configured to drive a coupled sense loop 1522a over a range of frequencies to cause the sense loop 1522a to resonate at a particular frequency. The resonant frequency measuring unit 1534 further includes a phase comparator 1548 configured to detect a phase between a measured voltage and current (e.g., a zero-crossing of a phase function). In addition, a gain/filter 1550 may also be included.

The output of the resonant frequency measuring unit 1534 may correspond to a measured resonant frequency of a sense loop 1522a that is provided to an evaluation unit 1532 of the detection circuit 1530. The evaluation unit 1532 includes a comparator 1536 configured to compare the received measured resonant frequency value for a sense loop 1522a with a reference frequency value. The output of the comparator 1536 is provided to a decider 1538 configured to determine, based at least in part on a difference between the measured and reference value if an object 924 is detected. Combining information from multiple loops 1522 may allow for determining position information regarding an object 924 to be detected. In addition, as is further described below, the evaluation unit 1532 may receive sense temperature inputs to compensate for operating conditions that may impact the measured resonant frequency due to conditions other than foreign objects.

In some aspects, the resonant loop method as described with reference to FIGS. 14 and 15 and further below (e.g., FIG. 16) may provide various benefits, at least including:

Measuring a resonant frequency may be simpler and more accurate than measuring an impedance or inductance. A detection circuit 1430 or 1530 may have less components and in some aspects limited to using an oscillator and a phase comparator detecting the phase between measured voltage and current e.g., the zero-crossing of the phase function.

The capacitor may be also already provided to suppress voltage induced by the strong alternating magnetic field used for wireless power transfer as present on the pad's surface and harmonics noise thereof. As such adding the capacitor does not add extra complexity. The resonance may act as a sense signal pre-conditioning (noise reduction) filter that also moves accordingly if a loop 1522a is detuned by a metal object.

Any temperature drift or aging of the capacitor may have a common effect on all resonant frequencies thus can be easily estimated and corrected in the evaluation unit (see section below).

Figure 16:
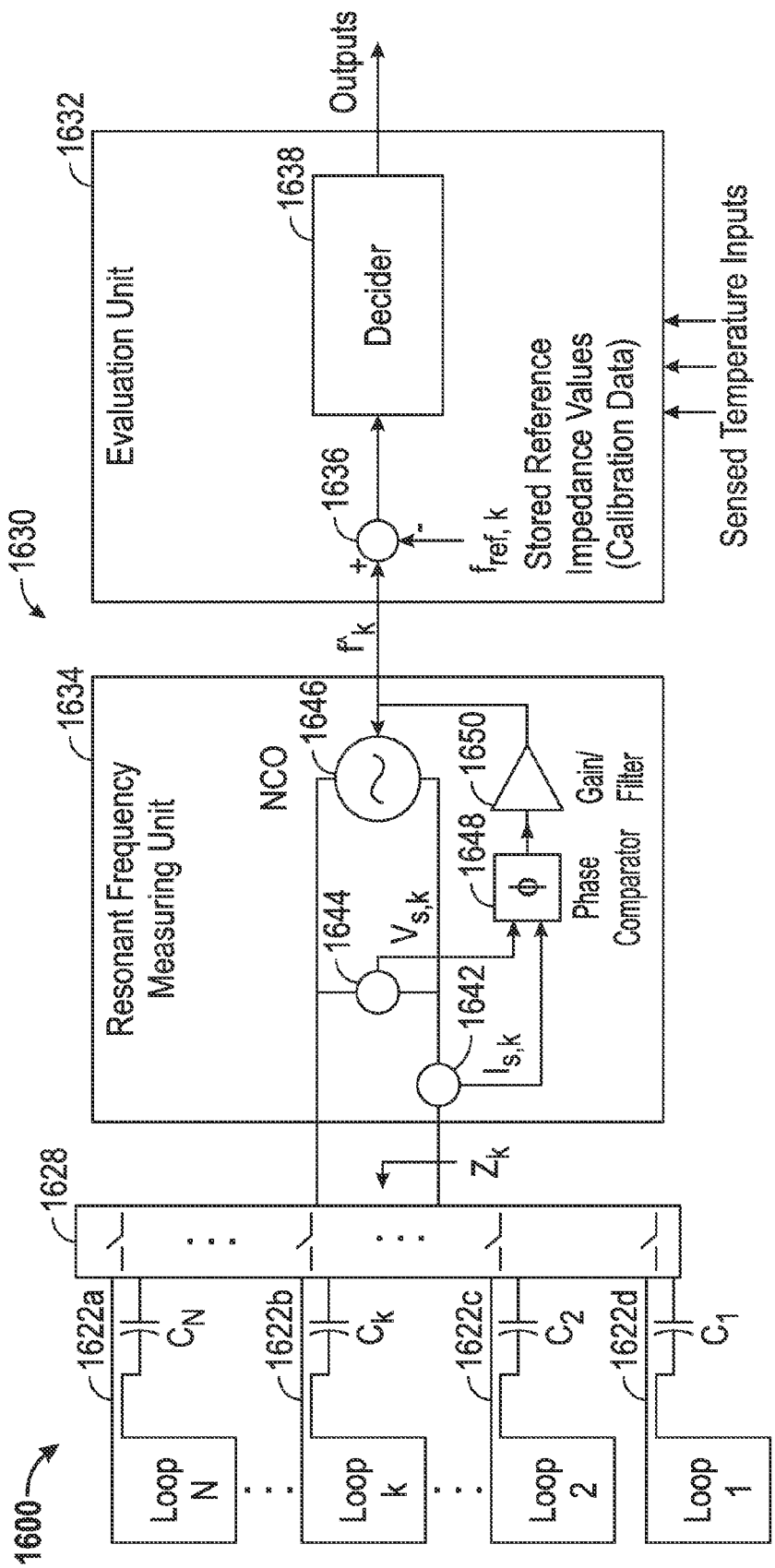
FIG. 16 is another functional block diagram of an exemplary circuit configured to detect an object based on sense loop resonant frequency measurements, in accordance with exemplary embodiments.

FIG. 16 is yet another functional block diagram of an exemplary circuit 1600 configured to detect an object based on sense loop resonant frequency measurements, in accordance with an exemplary embodiment. Each of the sense loops 1622a, 1622b, 1622c, and 1622d is electrically coupled to a resonance capacitor $C_1$, $C_2$, $C_k$, and $C_N$. It is noted that with reference to FIG. 14A, a coupling circuit 1426A may include a capacitor $C_N$. As such, each resonant circuit includes the capacitor $C_N$ of the coupling circuit 1426A and the corresponding sense loop 1622a. The capacitor $C_N$ is configured to reduce a variation of the resonant frequency by the multiplexer 1628 and further circuitry of the detection circuit 1630. For example, the each capacitor $C_1$, $C_2$, $C_k$, and $C_N$ is configured to be a low pass filter configured attenuate frequencies lower than the resonant frequency (e.g., attenuate frequencies corresponding to the frequency of a field used for wireless power transfer). The capacitors further provide isolation between components of the detection circuit 1630 including the multiplexer 1628 and the sense loops. The further components shown in FIG. 16 are similar to those described above with reference to FIG. 15. It is noted that with reference to the detection circuits 1530 and 1630 of FIGS. 15 and 16 and other detection circuits as described below, the detection circuits 1530 and 1630 may be configured to measure a characteristic dependent on or a function of the resonant frequency of each of the resonant circuits including the sense loops. For example, in addition to measuring a frequency at which each resonant circuit resonates, a Q-factor or other characteristic may be measured and compared to stored corresponding Q-factors or other corresponding characteristics of the native resonant circuit (i.e., unchanged by external items) to determine the presence of an object.

In some aspects, the embodiment shown in FIG. 16 may provide additional benefits. For example, the capacitance of each loop 1622 may removes the low frequency component as induced by the strong magnetic field on the pad's surface prior to multiplexing, thus relaxing requirements on the analog front-end circuitry, which preferably uses semiconductor (FET) type switches. It shall be appreciated that nonlinear distortion effects may occur in the analog multiplexer 1628 as the result of the low frequency induced that may reach several Volts. This is particularly true for multi-turn loops providing higher innate detection sensitivity but also higher induced voltages. Each capacitor may reduce variation of the resonant frequency that may be caused by the multiplexer 1628.

In one aspect, temperature drift of the loops' resonant frequencies may be unequal and specific for each sense loop therefore more difficult to assess and compensate for in the evaluation unit. Using capacitors with high temperature stability e.g., NP0 types, temperature drifts can be minimized and largely reduced to those of the sense loops.

With reference to FIG. 15 (and additionally applicable to FIG. 16), the high frequency oscillator 1546 for measuring the resonant frequency may be a Numerically Controlled Oscillator (NCO). An additional signal 1550 amplifier may be needed to generate sufficient sense current in the loops and as a buffer to provide a low impedance output (voltage source-like output). The low impedance output may be advantages to preserve the Q-factor of the sense loop circuit and thus the slope of the phase function at resonance (see below).

At least one voltage and one current sensor 1544 and 1542 respectively is used to provide inputs for analyzing the impedance or phase function of the sense loop 1522a as seen at the input port of the resonant frequency measuring unit 1534.

In an embodiment, the phase comparator 1548 may implement a heterodyne receiver approach e.g., by mixing the sense signals down to a narrow-band low intermediate frequency (IF) amplifier and performing phase comparison at IF. This approach may be chosen to increase the signal-to-noise ratio and thus measurement accuracy.

The resonant frequency search may be performed by a swept frequency generator using the oscillator 1546 e.g., starting at a frequency somewhat lower than the expected resonant frequency of the sense loop of concern and stopping the sweep when the differential phase reaches a predetermined value. To expedite the detection process and minimize response time, particularly in case of a large sensor array, the start frequencies may be derived from the reference values as used in the evaluation unit 1532, minimizing sweep range, thus minimizing sense time per loop.

Instead of a swept frequency generator, an impulse generator (not shown) or any other pseudo-random noise generator may be used to analyze the impedance function and measure the resonant frequency. Spectral analysis techniques such as Fourier Transform techniques (DFT, FFT, Gortzel algorithm) and similar techniques operating in the numeric domain may be used. These techniques may require sampling and digitizing the sense signals (voltage and current) using an adequate analog-to-digital converter.

To suppress sense loop induced transient noise as possibly generated by the energy transfer system, sweeping or pulsing may be performed in intervals between the low frequency switching transients. This method may effectively reduce noise without extra filtering requirements.

The embodiments as described with reference to FIGS. 13-16 and further herein may be enhanced by adding temperature sensors (not shown) at different places e.g., in the charging pad (below loop sensor array) and in the impedance measuring unit in order to increase stability against ambient temperature changes. Note that environmental requirements e.g., −30 to +80° C. may apply for a metal object detection solution that is integrated into an outdoor charging pad. Temperature as measured from different sensors may be used to pre-compensate measured impedance or resonant frequency values using a temperature model. Alternatively or additionally, different stored reference values applicable in defined temperature ranges may be used. These reference patterns may have been produced during manufacturing as part of a calibration procedure at different pad and ambient temperature levels.

A method conceptually similar to the least mean square method described above may be used to compensate for 'global' changes in a measured impedance pattern e.g., due to temperature drift and circuit aging (see section below).

Additionally, pattern recognition methods and artificial intelligence may be employed to enhance detection performance and reduce false alarm probability as is further described below.

Resonant Loops and Additionally Measuring their Q-factor

The embodiments described above with reference to FIGS. 14-16 describing detection based on resonant frequency measurements may be further enhanced by additionally measuring the Q-factor of the sense loop 1522a. In case of a series-tuned loop, resonant frequency and Q-factor represent the complex 'zero' of the impedance function Z(f), which may be expressed as $$p = -\sigma_z \pm j\omega_z$$

where $\sigma_p$ and $\omega_p$ denote the dampening coefficient and the resonant frequency, respectively.

The dampening coefficient relates to the Q-factor as follows:

$$\sigma_z = \frac{\omega_z}{2Q}$$

Measuring both to $\omega_z$ and $\sigma_z$ may provide additional information useful to increase detection probability and reduce false alarm probability.

There exist many ways to measure Q-factor using frequency domain and/or time domain analysis techniques as already mentioned in section above. Measuring the slope of the phase or measuring the resistance at resonance may be examples.

Weakly Coupled Resonant Loops

As indicated above, in some aspects, the sense loop leads and the analog multiplexers may excerpt a negative impact on the innate sensitivity of the loop impedance method. This may be particularly true for small loops e.g., 30×30 mm with 3-5 turns and a lead length e.g., above 0.5 m. Note that loops may be made of very thin copper wire/traces to avoid substantial eddy current losses when exposed to the strong magnetic field used for wireless power transfer, which may be unfavorable in regards to the innate sensitivity.

Accuracy of the loop impedance method is related to the slope of the phase in the impedance function, which is in turn related to the loop's Q-factor. A long lead to connect the loops to a central impedance measuring unit may decrease the Q factor and thus the slope of the phase as it adds resistance. The lead may also add considerable inductance. Since the object normally changes only the loop inductance, the relative change in overall impedance may become smaller with increasing lead length. Moreover, temperature and aging stability of the sense circuits may worsen for long lead lengths.

Similar impairments degrading temperature stability and thus the sensor's accuracy and reliability can be attributed to the analog multiplexers adding switch capacitance and significant resistance.

Therefore, the loop impedance method and the related loop resonance frequency method as described above may require the analog multiplexer and the impedance measuring unit to be located as close as possible to the loop array, meaning that active circuits may have to be integrated into the charging pad 926. This may lead to challenging design problems in considering the harsh environment, ground embedding, and MTBF required for infrastructure equipment. However, as indicated above, a capacitor, for example as shown with reference to FIG. 16, in some implementations may be sufficient as a coupling circuit to reduce variation of the resonant frequency by the detection circuitry and multiplexer.

Harmonics noise induced into sense loops at sense frequency may also generally impair the sensor's accuracy.

Figure 17C:
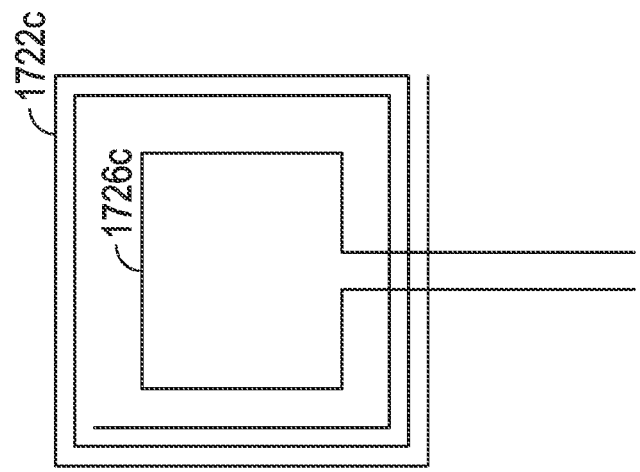
FIGS. 17A, 17B, and 17C are diagrams of exemplary weakly coupled resonant sense loop configurations, in accordance with exemplary embodiments.
Figure 17B:
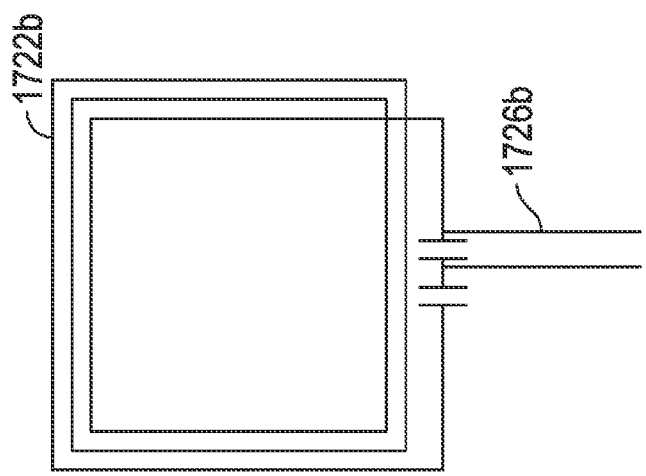
Figure 17A:
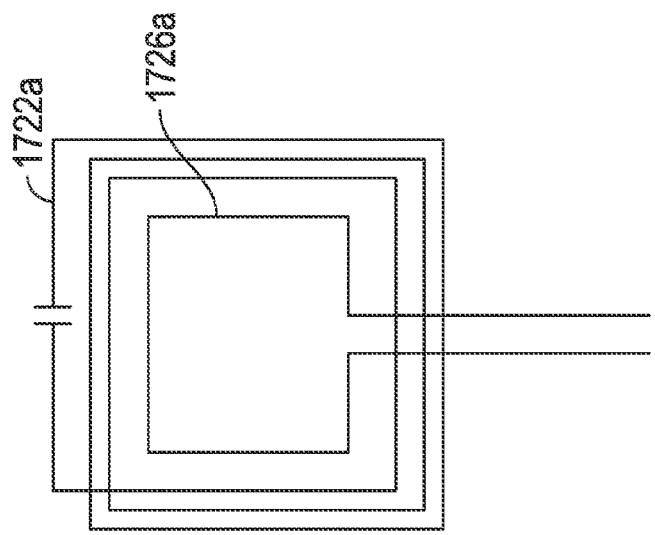

In accordance with further embodiments, at least some of these deficiencies can be remedied by using the coupling circuit or network as described above with reference to FIG. 14A. The coupling circuit 1426 is configured to reduce variation of resonant frequency of a resonant circuit formed at least by a sense loop by the detection circuit including any lead lines. For an example, in accordance with an embodiment an array of weakly coupled resonant loops may be used. Weak coupling may generally refer to coupling the sense loop to the detection circuit in a way that the detection circuit or any lead-lines from the detection circuit to the sense loop reduce an impact on or reduce altering the resonant frequency and/or other electrical characteristics of the sense loop. In some embodiments, loops may be either inductively coupled e.g., using a coupling loop or capacitively coupled e.g., using a capacitive voltage divider. FIGS. 17A, 17B, and 17C are diagrams of exemplary weakly coupled resonant sense loop configuration, in accordance with exemplary embodiments. FIG. 17A shows a resonant sense loop 1722a inductively coupled to a coupling loop 1726a. The coupling loop 1726 forms at least portion of the coupling circuit 1426 as described with reference to FIG. 14A. The coupling loop 1726 is then coupled to a detection circuit as will be further described below. FIG. 17B shows a resonant sense loop 1722b that is capacitively coupled using a capacitive voltage divider. FIG. 17C shows a sense loop 1722c that is self-resonant (e.g., the inherent capacitance of the sense loop 1722c to provide resonance at a distinct frequency) and is inductively coupled to a coupling loop 1726c.

Inductive coupling may principally allow self-resonant loops as illustrated in FIG. 17C with no or only little extra capacitance, which may significantly simplify the loop array and reduce production costs. Here, winding capacitance is used to produce resonance requiring a high L-C ratio design or higher frequency e.g., >20 MHz. Self-resonant loops may be no more predominantly magnetic. They may produce significant E-field making the sensor sensitive to dielectric objects, which may be undesirable in some cases.

Weak coupling may effectively reduce the impact on the resonant frequency and the Q-factor from the connecting leads and multiplexers thus increasing temperature and aging stability.

In some aspects, embodiments based on weakly coupling may provide various benefits. The resonant frequencies and the Q-factor may mainly depend on the sense loop's inductance L, loss resistance R and tuning capacitor C. Thus a small change as produced by a foreign object may become fully effective and is no more compromised by parasitic elements of the lead and the analog multiplexer circuitry. The slope of the phase function as seen by the impedance analyzer at resonance may be that of the resonant loop alone, therefore much steeper. Accuracy of measurements in presence of noise may significantly improve as long as the noise is comparatively small so that resonance can be reliably identified in the measured impedance function.

In a densely packed loop array, the resonant frequency of a sense loop may be influenced by its direct neighbors. Such resonance detuning or even resonance splitting effects may be particularly pronounced if neighboring loops resonate at an equal or a similar frequency. These effects however may not significantly impact sensitivity of this method. It may be useful to intentionally offset resonant frequencies of adjacent loops as will be further described below. Resonant frequencies may be assigned following a frequency reuse pattern.

Loops may be tuned to a desired resonant frequency by design e.g., by appropriately choosing turn count, winding length and selecting a capacitor from a standard value series e.g., an E-series.

In a printed circuit board (PCB) implementation, the capacitor may be embedded into the epoxy of the PCB or mounted in small recesses so that it is non-protrusive and well protected.

Figure 18A:
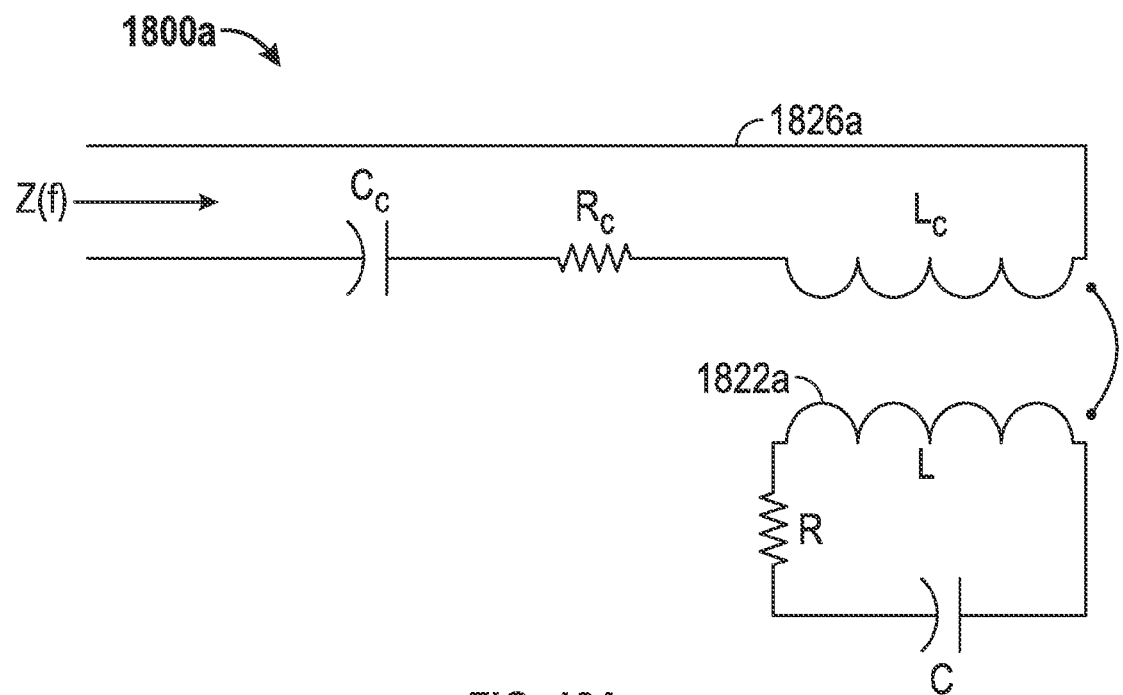
FIGS. 18A and 18B are schematic diagrams of equivalent circuits of an exemplary inductively coupled resonant sense loop, in accordance with an exemplary embodiment.
Figure 18B:
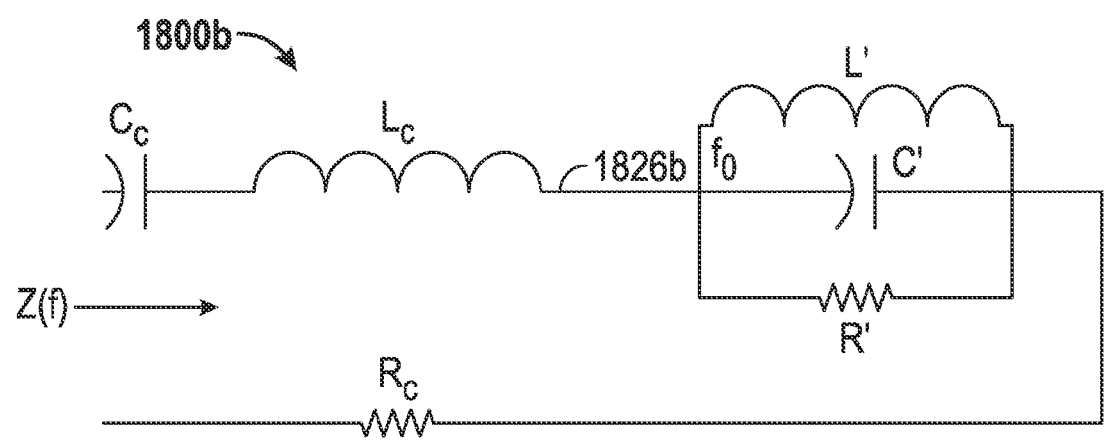

The effect of weak coupling may be explained using the equivalent circuits as shown below for the case of inductive coupling. FIGS. 18A and 18B are schematic diagrams of equivalent circuits 1800a and 1800b of an exemplary inductively coupled resonant sense loop 1822a, in accordance with an exemplary embodiment. The circuit 1800a is comprised of coupling loop 1826a with lead inductance $L_c$, coupling loop/lead loss resistance $R_c$ (e.g., that may form a portion of a coupling circuit 1426A). The capacitor $C_c$ serves to suppress the low frequency magnetic field induced voltage. At sense frequency however, the coupling loop 1826a may be considered non-resonant. The actual sense loop 1822a is composed of loop inductance L, loss resistance R and tuning capacitor C.

The circuit 1800b of FIG. 18B is obtained by reducing the circuit 1800a at the top into the coupling loop 1826. Here the circuit 1800b is shown as a transformed parallel-tuned L-C topology (L', C', R') producing a pronounced and rapid change of impedance Z when sweeping frequency over resonance. From the equivalent circuit 1800b, the resonance and slope of phase at resonance are mainly determined by the elements of the sense loop. They are largely insensitive to the parameters of the coupling loop and the lead length.

Figure 19:
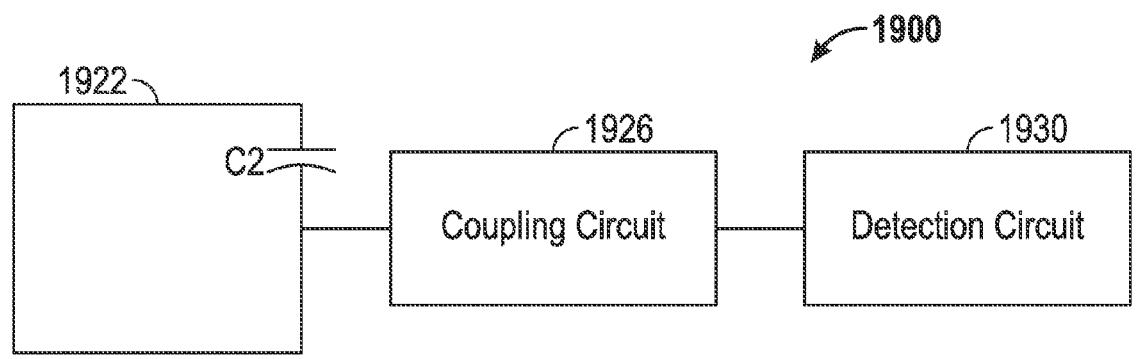
FIG. 19 is a functional block diagram of an exemplary circuit configured to detect an object using a coupling circuit between a detection circuit and a sense circuit, in accordance with an exemplary embodiment.

FIG. 19 is a functional block diagram of an exemplary circuit 1900 configured to detect an object using a coupling circuit 1926 between a detection circuit 1930 and a sense circuit 1922, in accordance with an exemplary embodiment. The circuit 1900 may include a sense circuit 1922 having a sense loop and a capacitor C2 (or inherent capacitance if self-resonant) so as to resonate at a distinct frequency (i.e., the capacitor C2 and sense loop substantially determine the resonant frequency). The circuit 1900 further includes a detection circuit 1930 configured to measure a characteristic that depends on a current resonant frequency of the sense circuit 1922 and configured to detect the presence of an object in response to detecting a difference between the measured characteristic and a corresponding reference characteristic dependent on the resonant frequency. As an example, the detection circuit 1930 may have one or more of the components as described above with reference to the detection circuit 1530 of FIG. 15 and may use any of the methods and/or techniques described herein for detecting objects based on resonant frequency measurements. Furthermore, the circuit 1900 includes a coupling circuit 1926 configured to reduce variation of the resonant frequency of the sense circuit 1922 by the detection circuit 1930. For example, in an embodiment, the coupling circuit 1926 may provide weak coupling between the sense circuit 1922 and the detection circuit 1930. In the embodiment of FIG. 19, the capacitor C2 (or self-capacitance) and the sense loop alone form a resonant sense circuit 1922 that may not include the coupling circuit 1926.

Figure 20:
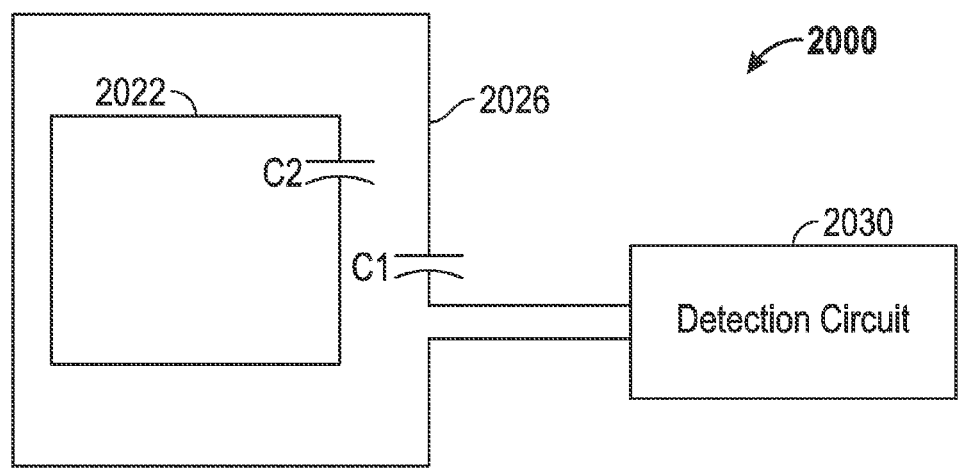
FIG. 20 is a functional block diagram of a circuit as shown in FIG. 19 where the detection circuit is inductively coupled with a sense circuit via a coupling loop, in accordance with an exemplary embodiment.

FIG. 20 is a functional block diagram of a circuit 2000 as shown in FIG. 19 where the detection circuit 2030 is inductively coupled with a sense circuit 2022 via a coupling loop 2026, in accordance with an exemplary embodiment. As such, the coupling circuit 1926 of FIG. 19 may include a coupling loop 2026 optionally having a capacitance C1 that is conductively connected to the detection circuit 2030 and inductively coupled to the sense circuit 2022 including a sense loop and capacitance C2. Stated another way, the sense circuit 2022 is galvanically isolated from the detection circuit 2030. Operation of the coupling loop 2026 may reduce variation of the resonant frequency of the sense circuit 2022 by the detection circuit 2030 including any lead line from the detection circuit 2030 to the coupling loop 2026.

Figure 21:
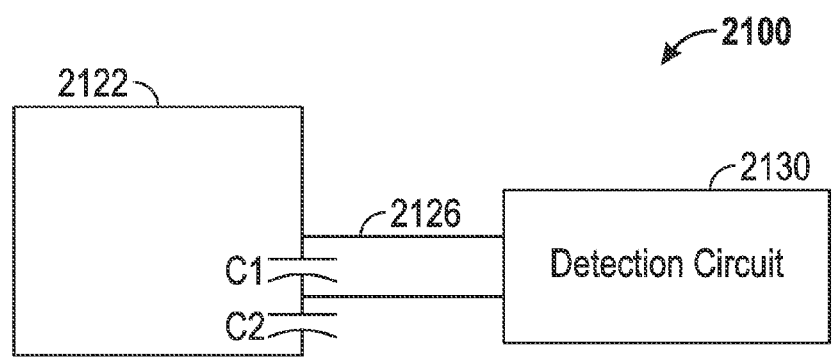
FIG. 21 is a functional block diagram of a circuit as shown in FIG. 19 where the detection circuit is capacitively coupled with a sense circuit, in accordance with an exemplary embodiment.

FIG. 21 is a functional block diagram of a circuit 2100 as shown in FIG. 19 where the detection circuit 2130 is capacitively coupled with a sense circuit 2122, in accordance with an exemplary embodiment. The circuit 2100 includes a capacitive voltage divider including capacitors C1 and C2 between the sense circuit 2122 to form the coupling circuit 2126. The difference in size of the capacitors C1 and C2 may be provided such that the resonant frequency of the sense circuit 2122 (including a sense loop) is primarily defined by the smaller capacitor. The capacitor voltage divider reduces variation of the resonant frequency of the sense circuit 2122 by the detection circuit 2130 or any lead lines from the detection circuit 2130 to the sense circuit 2122.

Embodiments using weak coupling as described above may principally allow for much longer lead length. This may enable embodiments with a fully passive sensor circuit in the charging pad 936 and with the active circuits (foreign object detection electronics such as detection circuit as described above) integrated into a remotely located unit e.g., the charging power supply unit 236 (FIG. 2).

In accordance with an embodiment, the following method may be used and implemented by a detection circuit 1930 for measuring the resonant frequency of the k-th sense loop at the input of the impedance analyzer unit (measurement port). However, as noted above, other characteristics dependent on the resonant frequency may additionally be measured.

1. Measure the complex impedance function $Z_k(f)$ over a sufficiently large frequency range
2. Estimate the coupling loop/lead impedance by analyzing the complex impedance function
3. Subtract the estimated coupling loop/lead impedance function $\hat{Z}_{c,k}(f)$ from the measured impedance function $Z_k(f)$
4. Identify the resonance of the sense loop 1922 in the resulting differential impedance function $\Delta Z_k(f) = Z_k(f) - \hat{Z}_{c,k}(f)$
5. Measure frequency of the corresponding zero crossing of the phase function $\arg\{\Delta Z_k(f)\}$ or the imaginary part of the impedance function $\text{Im}\{\Delta Z_k(f)\}$ and/or measure frequency of the local maximum of the real part of the differential impedance function $\text{Re}\{\Delta Z_k(f)\}$ that is produced at loop's resonance.

As already described above, the Q-factor or the dampening coefficient defined as the real part of the complex pole frequency $$P = -\sigma p \pm j\omega_p$$

may be measured additionally to enhance metal object detection based on the weakly coupled approach.

Wiring complexity and the high number of analog switches that have to be provided is another major issue of inductive sensing using a large number of sense loops. Therefore, methods reducing wiring and circuit complexity are desirable. This may be particularly true if a solution with a purely passive sensor network in the pad and a remotely located detection circuit is targeted.

In fact, the weakly coupled approach may have the potential to significantly reduce wiring and circuit complexity by combining neighboring loops to groups (clusters), each group associated to a single/common coupling network.

This new configuration called multiple coupled resonant loops may generally compromise coupling but may still provide sufficient coupling to unambiguously and accurately determine resonant frequency of each of several loops individually.

Figure 22:
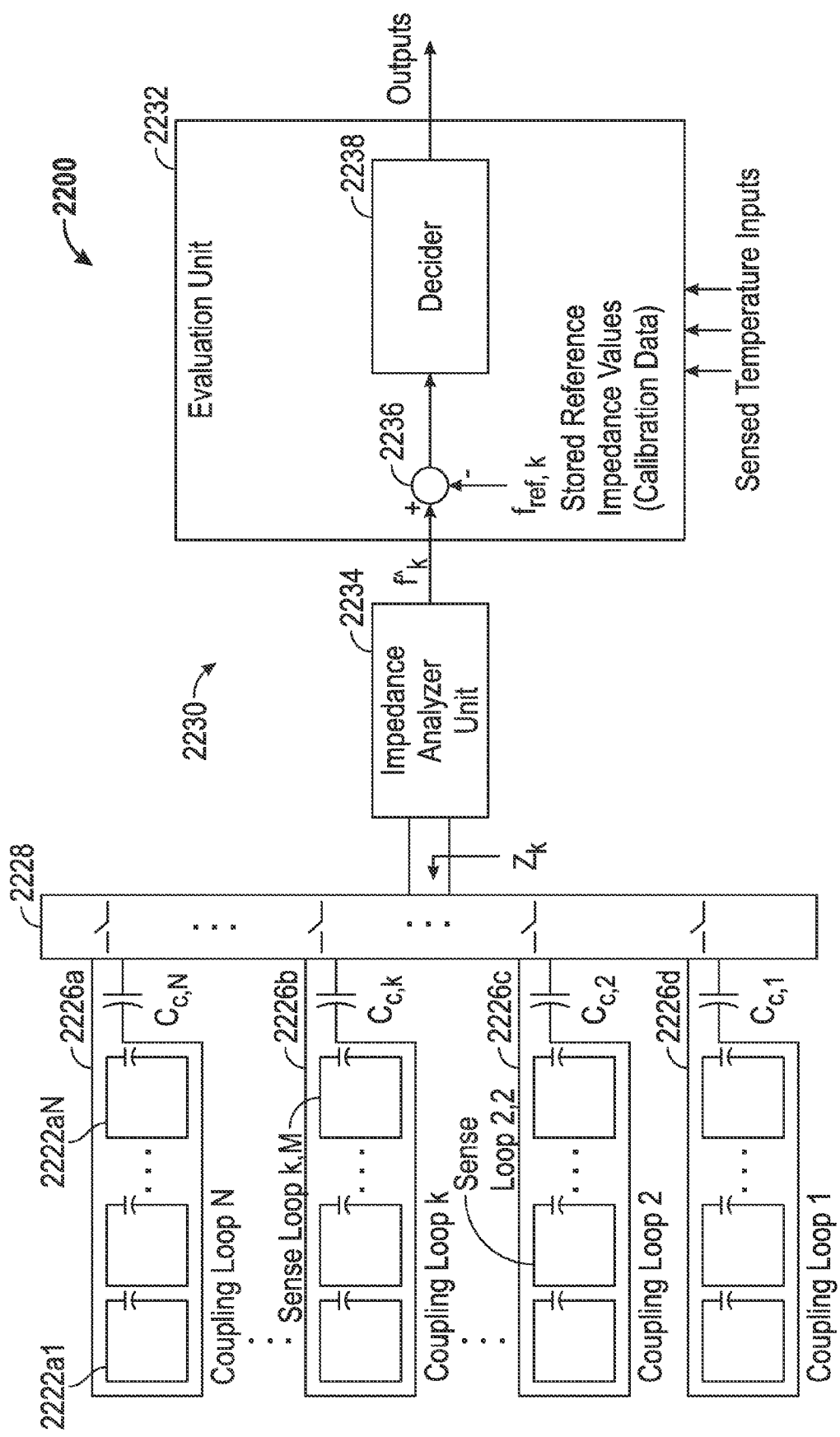
FIG. 22 is a functional block diagram of an exemplary circuit configured to detect an object using a plurality of coupling circuits between a detection circuit and plurality of sense circuits, in accordance with an exemplary embodiment.

FIG. 22 is a functional block diagram of an exemplary circuit 2200 configured to detect an object using a coupling circuit between a detection circuit 2230 and a plurality of sense loops, in accordance with an embodiment. The circuit 2200 includes several coupling networks (e.g., coupling circuits as described above with reference to FIGS. 19 and 20) each including a coupling loop 2226a, 2226b, 2226c, and 2226d. Each of the coupling loops 2226a, 2226b, 2226c, and 2226d are inductively coupled to a plurality of sense circuits each having a sense loop and capacitance (e.g., either self-capacitance or an added capacitor). For example, coupling loop 2226a may form a coupling network including a plurality of sense circuits including sense circuits 2222a1 and 2222aN (referred to herein collectively as 2222 hereinafter). The coupling loops 2226a, 2226b, 2226c, and 2226d are coupled to a multiplexer 2228 such that each of the coupling networks is selectively coupled to a detection circuit 2230 configured to measure the resonant frequency of each sense circuit 2222 coupled to a particular coupling loop 2226a. The coupling loops 2226a, 2226b, 2226c, and 2226d are each configured to reduce variation of the resonant frequency of the each sense circuit 2222 by the detection circuit 2230. The detection circuit 2230 includes an impedance analyzer unit 2234 for measuring resonant frequencies and an evaluation unit 2232 for comparing measured values with reference values and to determine information regarding objects sensed via the sense circuits 2222. The sense circuits 2222 may form a densely packed multi-dimensional array of loops in a plane configured to detect an object placed on a surface of the plane in which the sense circuits 2222 are configured. As noted above, detection circuit 2230 may measure other characteristic that are a function of the resonant frequencies of each of the sense circuits 2222.

In accordance with the embodiment shown in FIG. 22, a plurality of sense loops are therefore combined to a group that is associated to a single/common coupling network. Furthermore, the sense loops 2222 are tuned to different resonant frequencies forming an impedance one port network with distinct poles and zeros, whose relevant pole and/or zero frequencies are distinguishable and measurable under operating conditions.

Poles and zeros as resulting from such a network may be a highly complex function of each inductive and capacitive element including all cross coupling effects (mutual inductances) as they may occur between neighboring loops in a densely packed array. A metal object placed on top of such loop array generally changes some of the poles and zeros, which can be detected using an appropriate method e.g., comparing measured poles and zeros with a reference template. It should be appreciated that while FIG. 22 shows the sense circuits 2222 inductively coupled to the detection circuit via coupling loops 2226a-d, the sense circuits 2222 may be capacitively coupled based on a concept shown in FIG. 21 in accordance with another embodiment.

As described above, in an embodiment, each of the sense circuits 2222 may be inherently configured to have a different resonant frequency in the absence of any objects.

Figure 23:
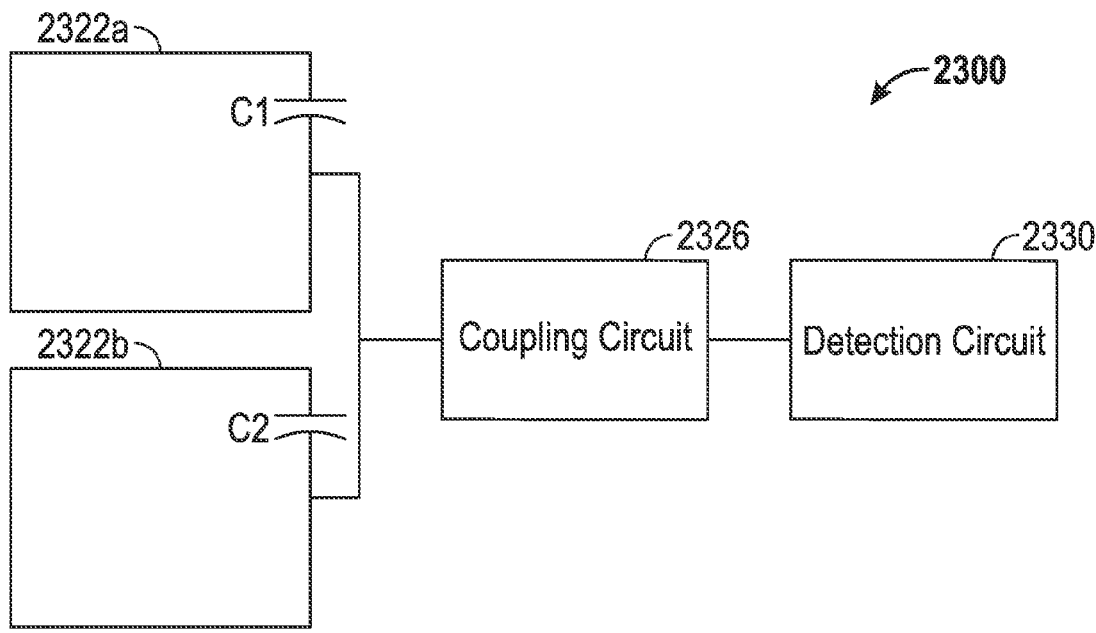
FIG. 23 is a functional block diagram of an exemplary circuit configured to detect an object using a plurality of sense circuits configured to have different resonant frequencies, in accordance with an exemplary embodiment.

FIG. 23 is a functional block diagram of an exemplary circuit 2300 configured to detect an object using a plurality of sense circuits 2322a and 2322b (each having a sense loop) configured to have different resonant frequencies, in accordance with an exemplary embodiment. The circuit 2300 includes sense circuit 2322a having a capacitance C1 and sense circuit 2322b having a capacitance C2 that may be different than C1. Each sense circuit 2322a and 2322b may therefore natively have a particular frequency for which the sense loop 2322a and 2322b is resonant. The circuit 2300 includes a detection circuit 2330 configured to measure a characteristic that is a function of the resonant frequency of each of the sense circuits 2322a and 2322b to determine the presence or absence of an object. The detection circuit 2330 may implement and or include one or more of the techniques and components as described above, for example with reference to FIGS. 13-22. The circuit 2300 includes coupling circuit 2326 coupled between the detection circuit 2330 and the sense circuits 2322a and 2322b. In some embodiments, the coupling circuit 2326 is configured to reduce variation of the resonant frequencies of the sense circuits 2322a and 2322b by the detection circuit 2330 including any lead lines. By using multiple sense circuits 2322a and 2322b, the sensitivity of the detection system may increase such that the detection circuit 2330 is configured to measure a position of an object relative to a position of the sense circuits 2322a and 2322b such that the system may detect the position of an object within the system.

Figure 24:
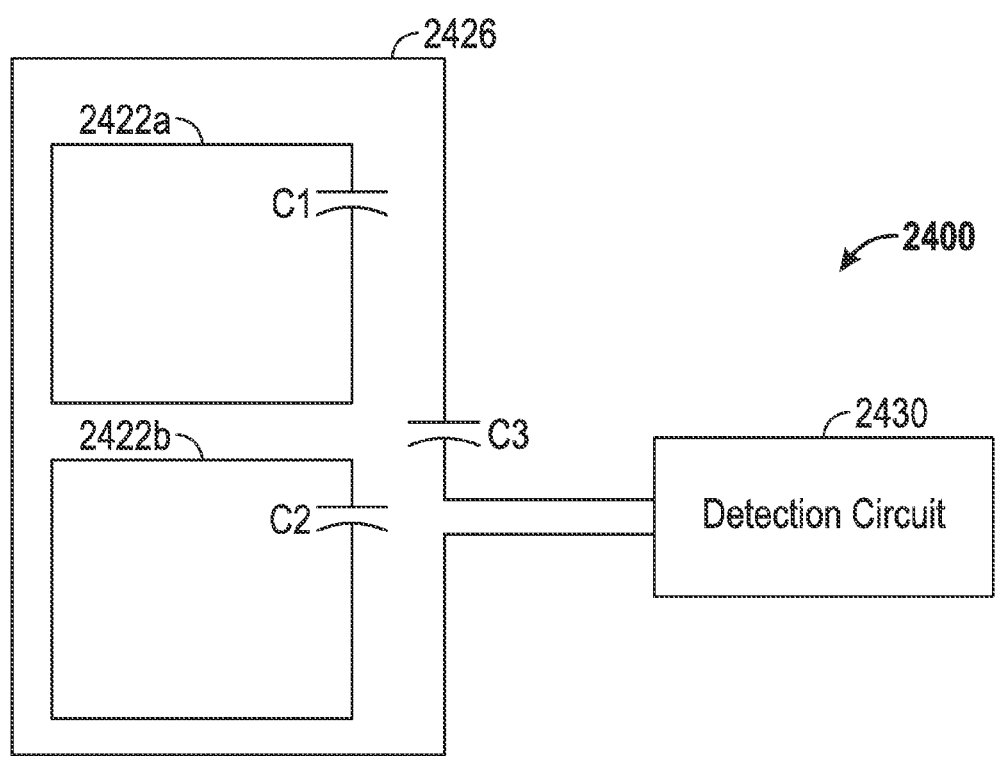
FIG. 24 is a functional block diagram of a circuit as shown in FIG. 23 where the detection circuit is inductively coupled to sense circuits having different resonant frequencies, in accordance with an exemplary embodiment.

Using sense circuits 2322a and 2322b with different resonant frequencies may allow for improving sensitivity and reducing complexity. For example, FIG. 24 is a functional block diagram of a circuit 2400 as shown in FIG. 23 where the detection circuit 2430 is inductively coupled to sense circuits 2422a and 2422b having different resonant frequencies, in accordance with an exemplary embodiment. The detection circuit 2430 may be configured to measure the current resonant frequencies of both of the sense circuits 2422a and 2422b when driving the coupling loop 2426. This may allow for reduced complexity and improved sensitivity as, for example resonant frequencies of a large number of sense circuits 2422a and 2422b may be measured via driving a single coupling loop 2426.

Regardless of the coupling type, the coupling network may be configured to provide optimum and similar coupling to each loop of a group.

In an embodiment, each loop 2222 of a group may be part of the outer contour/perimeter of that group having at least one side/edge on the contour/perimeter line. The group may be encompassed by a coupling loop essentially going along the contour/perimeter of that group. Single column or a double column of loops as shown in the figure below are possible configurations. Coupling may be intentionally reduced for those loops that have more than one edge/side on the contour/perimeter line. This may be accomplished by cropping corners of the coupling loop.

Figure 25D:
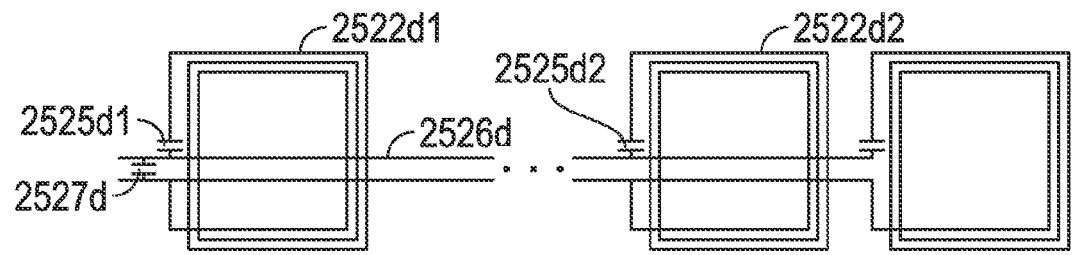

FIGS. 25A, 25B, 25C, 25D, 25E, and 25F are diagrams of exemplary configurations sense loop arrays inductively or capacitivley coupled to a detection circuit, in accordance with an exemplary embodiment. For an example, an embodiment of a sense loop array may be derived from the single loop coupling as shown in FIG. 25A. FIG. 25A includes a coupling loop 2526a inductively coupled to a multi-dimensional array of sense loops including sense loop 2522a1 and 2522a2. FIG. 25B shows another configuration where a coupling loop 2526b is inductively coupled to a column of single sense loops including sense loop 2522b1 and sense loop 2522b2. FIG. 25C shows another embodiment of a coupling loop 2526 inductively coupled to a row of sense loops including sense loop 2522c1 and sense loop 2522c2. The configuration depicted in FIG. 25C also may provide substantially equal coupling factor to each sense loop 2522c1 and 2522c2. Linear rows, meander-shaped or serpentine-shaped arrangements of loops may be connected to a group.

Other arrangements e.g., triple column of loops with the coupling loop not in proximity of all of the sense loops show weaker coupling to the loops in the center. In one aspect, this technique may be used if the loop array is integrated into the enclosure of a magnetic pad additionally attenuating the magnetic field in the center of the coupling loop.

The concept of multiple inductively coupled resonant loops may be expanded to hierarchical (concatenated) structures comprised of groups and subgroups. A group may be formed by a plurality of resonant loops operationally coupled to a coupling loop. The resonant loops of this group in turn may serve as coupling loops for resonant loops belonging to subgroups (lower hierarchy level), and so on.

Alternatively, multiple loops 2522d1 and 2422d2 may be coupled capacitively to a single feed line 2526d using the capacitive voltage divider as shown in FIG. 25D. The resulting topology that is shown in FIG. 25D may be considered as the electrically dual topology of the multiple inductively coupled resonant loops. Each sense loop 2522d1 and 2522d2 in FIG. 25D is coupled in series with a capacitor 2525d1 and 2525d2, respectively, to form a resonant circuit (i.e., they are series tuned). The sense loop 2522d1 and capacitor 2525d1 substantially determine the resonant frequency. A coupling capacitor 2527d common to all sense loops 2522d1 and 2522d2 is coupled in parallel with the resonance capacitors 2525d1 and 2525d2 to form a capacitive voltage divider. In one aspect, the coupling capacitor 2527d is the "larger" capacitor while each of the resonance capacitors 2525d1 and 2525d2 are the "smaller" capacitors. It is noted that with reference to FIG. 14A, a coupling circuit 1426A may include the coupling capacitor 2527d while each sense circuit may include the series tuned sense loop 2522d1 with resonance capacitor 2525d1.

Figure 25E:
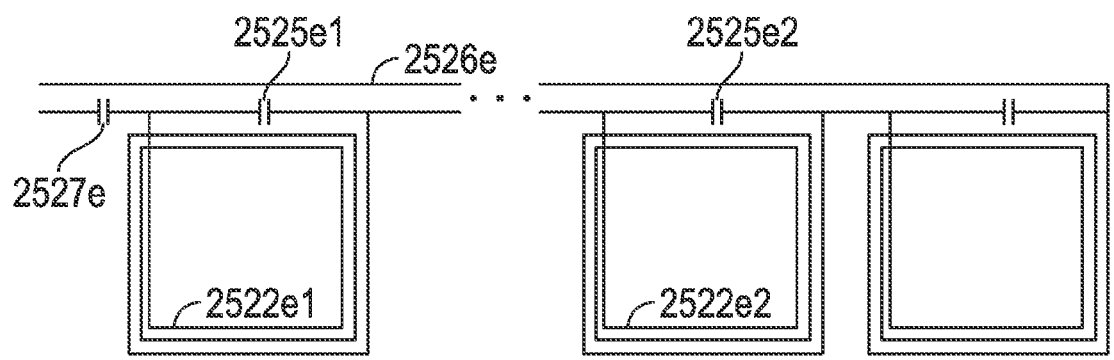

FIG. 25E is another topology using a capacitive voltage divider to provide a weak coupling in accordance with an embodiment. In this case, each sense loop 2522e1 and 2522e1 are parallel tuned using resonance capacitors 2525e1 and 2525e2, respectively. The sense loop 2522e1 and resonance capacitor 2525e1 substantially determine the resonance frequency. A coupling capacitor 2527e common to all sense loops 2522e1 and 2522e2 is coupled in series with resonance capacitors 2525e1 and 2525e2. In one aspect, the coupling capacitor 2527e is the "larger" capacitor while each of the resonance capacitors 2525d1 and 2525d2 are the "smaller" capacitors. It is noted that with reference to FIG. 14A, a coupling circuit 1426A may include the coupling capacitor 2527e while each sense circuit may include the parallel tuned sense loop 2522e1 with resonance capacitor 2525e1.

Figure 25F:
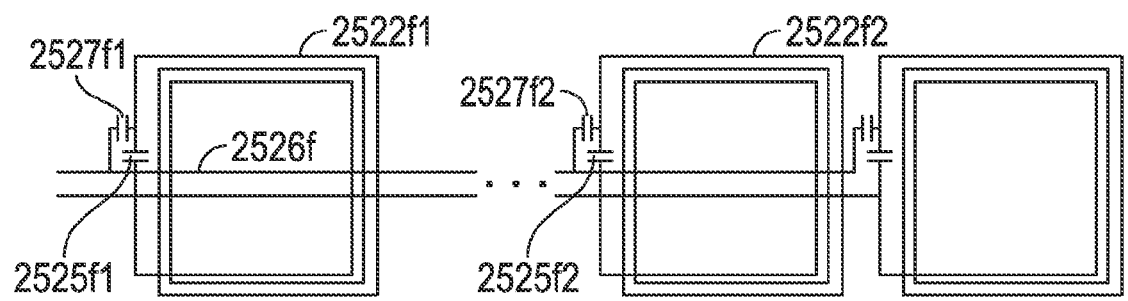

FIG. 25F is another topology using a capacitive voltage divider to provide a weak coupling in accordance with an embodiment. In this case, each sense loop 2522f1 and 2522f1 are parallel tuned using resonance capacitors 2525f1 and 2525f2, respectively. The sense loop 2522f1 and resonance capacitor 2525f1 substantially determine the resonance frequency. Coupling capacitors 2527f1 and 2527f2 are included for each sense loop 2522f1 and 252ssf2 such that each is connected in parallel with resonance capacitors 2525f1 and 2525f2, respectively. In one aspect, each coupling capacitor 2527f1 and 2527f2 are the "larger" capacitors while each of the resonance capacitors 2525d1 and 2525d2 are the "smaller" capacitors. It is noted that with reference to FIG. 14A, there may be multiple coupling circuits that each include coupling capacitors 2527f1 and 2527f2 while each sense circuit may include the parallel tuned sense loop 2522e1 with resonance capacitor 2525e1.

Other e.g., mixed coupling topologies are also possible.

FIGS. 26A, 26B, 26C, 26D, 26E, and 26F are schematic diagrams of exemplary equivalent circuits 2600a and 2600b of an inductively and capacitively coupled resonant loop array, in accordance with an exemplary embodiment. The circuit 2600a includes a coupling loop 2626a including a low frequency suppressing capacitor $C_c$, the coupling loop's/lead's inductance $L_c$ and loss resistance $R_c$. The circuit 2600a includes multiple sense loops 2622a1 and 2622a2 including the L, C, R elements as well as the mutual inductance (coupling coefficient) between coupling loop and each resonant loop. Other possible cross couplings are neglected.

Figure 26A:
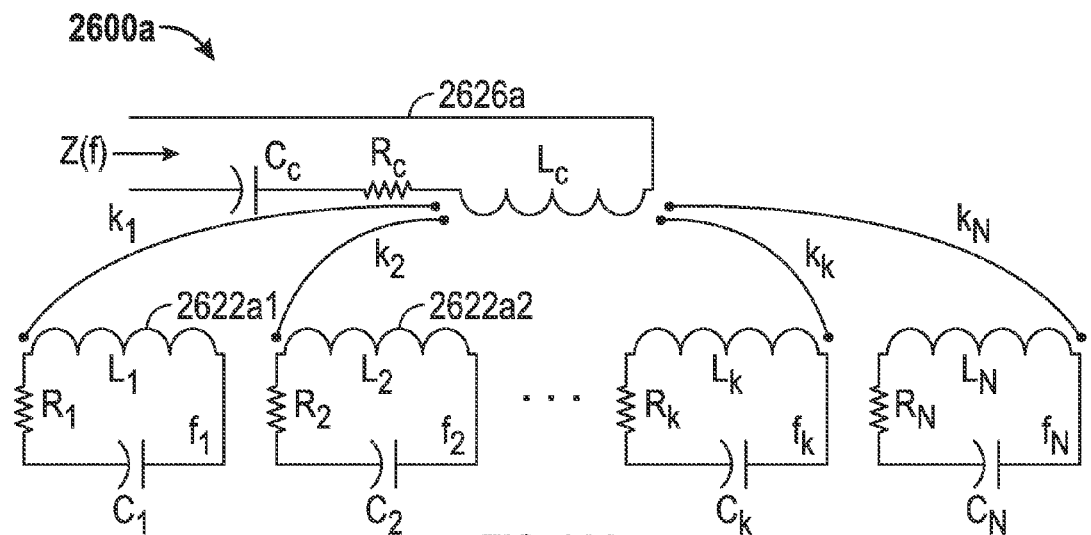
FIGS. 26A, 26B, 26C, 26D, 26E, and 26F are schematic diagrams of exemplary equivalent circuits of inductively or capacitively coupled resonant loop arrays, in accordance with an exemplary embodiment.
Figure 26B:
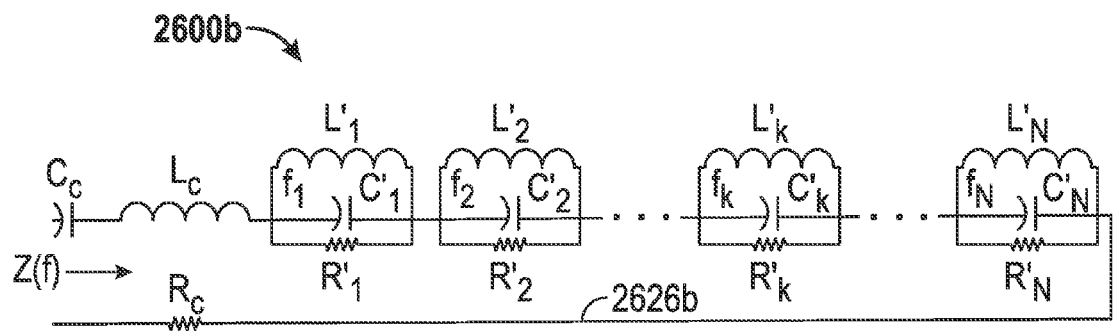

As already described above, the resonant circuits 2622a1 and 2622a2 may be reduced to the primary side (coupling loop) resulting in an equivalent circuit 2600b that may be approximately represented as shown in FIGS. 26B. Here again, each resonant loop 2622a1 and 2622a2 appears as a parallel resonant circuit whose response are visible in the impedance function Z(f).

Figure 26C:
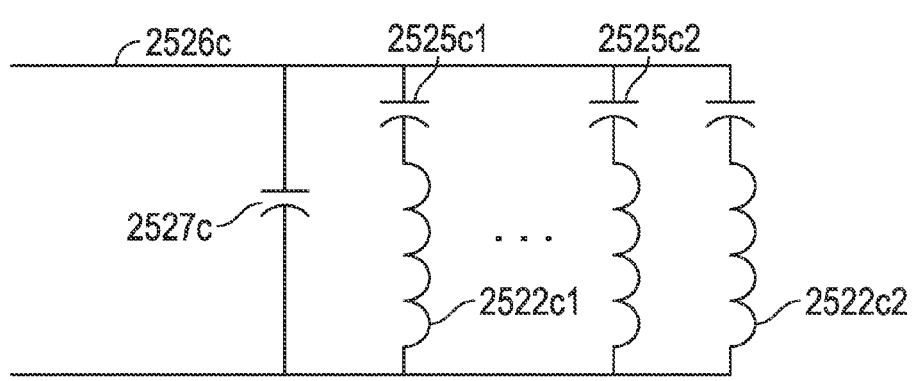
Figure 26D:
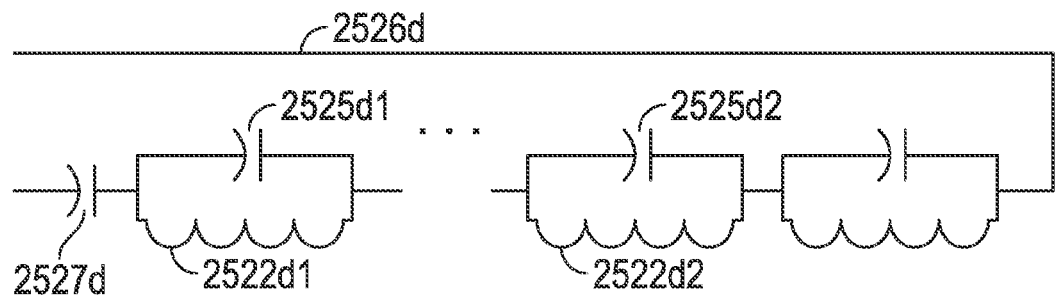
Figure 26E:
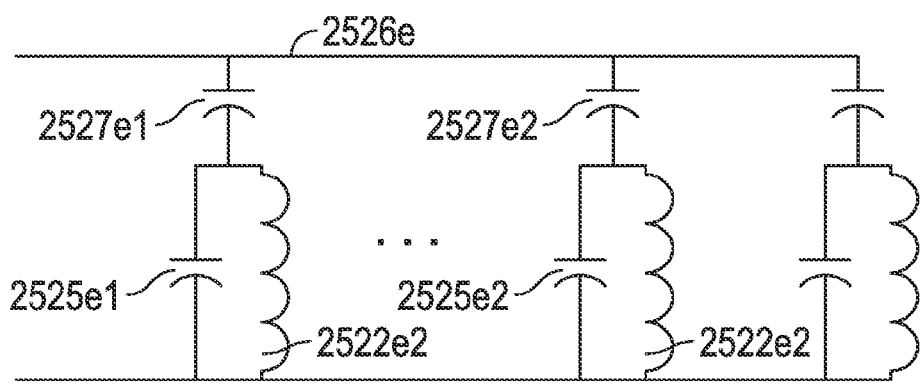
Figure 26F:
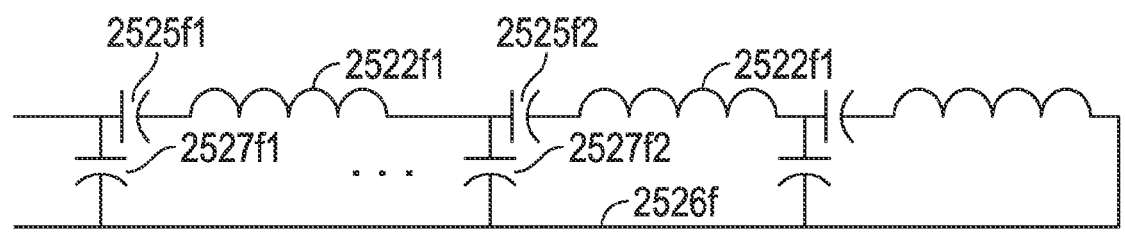

FIG. 26C is an equivalent schematic diagram of the sense loop configuration shown in FIG. 25D. As shown each sense circuit comprising inductance 2522c1 and capacitance 2525c1 is series tuned and all sense circuit are coupled to a common coupling capacitor 2527c in parallel. FIG. 26D is an equivalent schematic diagram of the sense lop configuration shown in FIG. 25E where each sense circuit comprising inductance 2522d1 and capacitance 2525d1 are parallel tuned and each sense circuit is coupled the common coupling capacitor 2527d in series. FIG. 26E is an equivalent schematic diagram of the sense loop configuration shown in FIG. 25F where each sense circuit comprising inductance 2522e1 and capacitance 2525e1 are parallel tuned and coupled to each coupling capacitor 2527e1 and 2527e2 in parallel. Furthermore, FIG. 26F is an equivalent schematic diagram of another sense loop configuration where each sense circuit comprising inductance 2522f1 and 2522f2 and capacitance 2525f1 and 2525f2 are series tuned and coupled to each coupling capacitor 2527f1 and 2527f2 in series. It is noted that in any of the above topologies, either a self-resonant loop may be used having the resonance capacitance inherent therein or an added resonance capacitor may be added.

In accordance with an embodiment, a detection circuit may implement the following method for measuring the resonant frequencies of the k-th array/group of inductively coupled resonant sense loops at the input of the impedance analyzer unit 2234 (FIG. 22) (measurement port). However, as noted above, other characteristics dependent on the resonant frequency may additionally be measured.

1. Measure the complex impedance function $Z_k(f)$ over a sufficiently large frequency range 2. Estimate the coupling loop/lead impedance by analyzing the complex impedance function
3. Subtract an impedance function $Z^{\wedge}_{c,k}(f)$ from the measured impedance function $Z_k(f)$. The impedance function $Z^{\wedge}_{c,k}(f)$ may include the estimated coupling loop/lead impedance function and other correction function as needed to optimally perform the following steps.
4. Identify resonances of each sense loop in the resulting differential impedance function $\Delta Z_k(f) = Z_k(f) - Z^{\wedge}_{c,k}(f)$
5. Measure all frequencies of the corresponding zero crossings of the phase function $\arg\{\Delta Z_k(f)\}$ or the imaginary part of the impedance function $\text{Im}\{\Delta Z_{k,n}(f)\}$ and/or measure all frequencies of the local maxima of the real part of the differential impedance function $\text{Re}\{\Delta Z_k(f)\}$ that are produced at loops' resonances.

Figure 27:
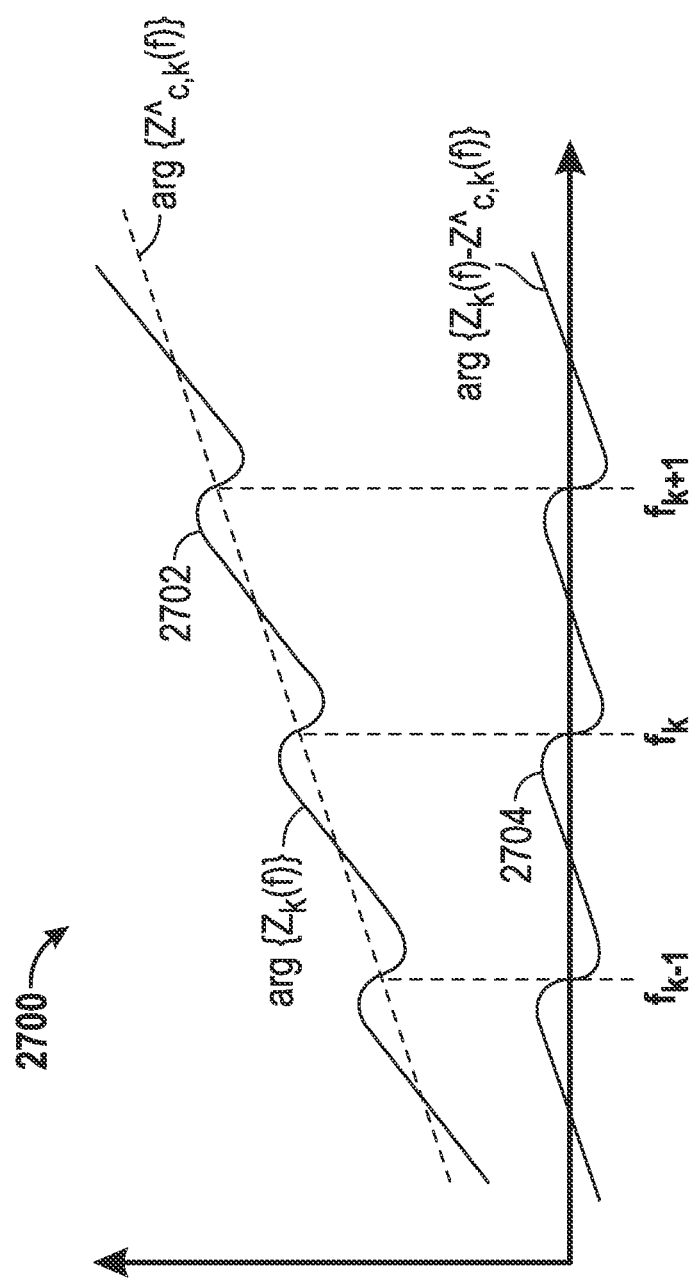
FIG. 27 is a plot showing a phase response of an inductively coupled resonant loop array before and after compensating for an impedance of a coupling loop, in accordance with an exemplary embodiment.

FIG. 27 is a plot 2700 showing a phase response of an inductively coupled resonant loop array before and after compensating for an impedance of a coupling loop, in accordance with an exemplary embodiment. FIG. 27 illustrates the procedure of subtracting the estimated coupling loop/lead impedance and measuring the resonant frequencies in the phase function of the resulting differential impedance function.

A similar method/procedure may apply for a capacitively coupled loop array. Instead of searching local maxima in $Z_k(f)$, item 5 is modified to local minima of the real part of the differential impedance function $\text{Re}\{\Delta Z_k(f)\}$ and determine the minima as produced by each sense loop's resonance.

Computing and evaluating of at least one of a first, second, and third derivative of the impedance function may also be useful to identify positions of poles/zeros of the impedance function $Z_k(f)$.

As already described in a subsection above, the Q-factors or the dampening coefficients defined as the real part of the complex poles or zeros of the impedance function $Zk(f)$ $$p_{k,i} = -\sigma_{p,k,i} \pm j\omega_{p,k,i}, \text{ or } z_{k,i} = -\sigma_{z,k,i} \pm j\omega_{z,k,i}$$

respectively, may be measured additionally for each resonance $\omega_{k,i}$ to enhance metal object detection based on the multiple coupled resonant loop approach.

As already mentioned above, switching noise may be induced into the sense loops. To maximize signal-to-noise ratio and thus measurement accuracy at resonance frequencies, a current source-like high frequency generator may be used to measure $Z_k(f)$ in case of inductive coupling, whilst for capacitive coupling, a voltage source-like generator is preferably employed. This approach avoids measuring impedance in current minima thus at low signal-to-noise ratio. The coupling loop/lead's inductance may already suffice to mimic a current source-like characteristic provided that the HF source generates enough high voltage.

As described above, for example with reference to FIGS. 23 and 24, assigning resonant frequencies to sense loops may also be provided. Preferably, resonant frequencies (poles/zeros) of sense loops belonging to the same group are adequately and smartly spaced apart so that they can be easily identified and accurately measured. This assignment may take into account the Q-factor of the sense loops, design constraints of the impedance analyzer circuits, bandwidth constraints, noise and environmental disturbance effects, as well as detuning effects that may occur when integrated the sense loop array into the target magnetic pad.

For example, for a sense loop size of 35×35 mm, a Q-factor in the range from 50-80 may be achieved corresponding to a 3 dB fractional bandwidth of 0.02-0.013. Assuming a total fractional bandwidth of 1 for a high frequency sensing system operating e.g., in the range from 5 to 15 MHz, up to about 40 resonant frequencies may be allocated e.g., equidistantly spaced. These resonant frequencies may have to be selectively assigned to loops and groups of loops in order to optimally use and reuse the available bandwidth in different groups of loops. The number of loops per group may be the result of a trade-off between complexity and detection sensitivity.

According to an embodiment, the number of loops per group may vary between 20 and 30 given the above example of an available bandwidth. Thus, a complexity reduction in wiring and multiplexing up to a factor of 30 may be expected.

Measuring bandwidth may be expanded towards even higher frequencies. It shall be noted however, that sensitivity on dielectric objects (e.g., water, snow, ice, foliage) may also increase. This undesirable effect may be diminished by a lower turn count for those sense loops/coils tuned to upper edge frequencies. This may result in single turn loops in the end. Multi-turn loops are considered most appropriate at lower frequencies e.g., <10 MHz if maximum Q-factor has to be targeted.

Figure 28:
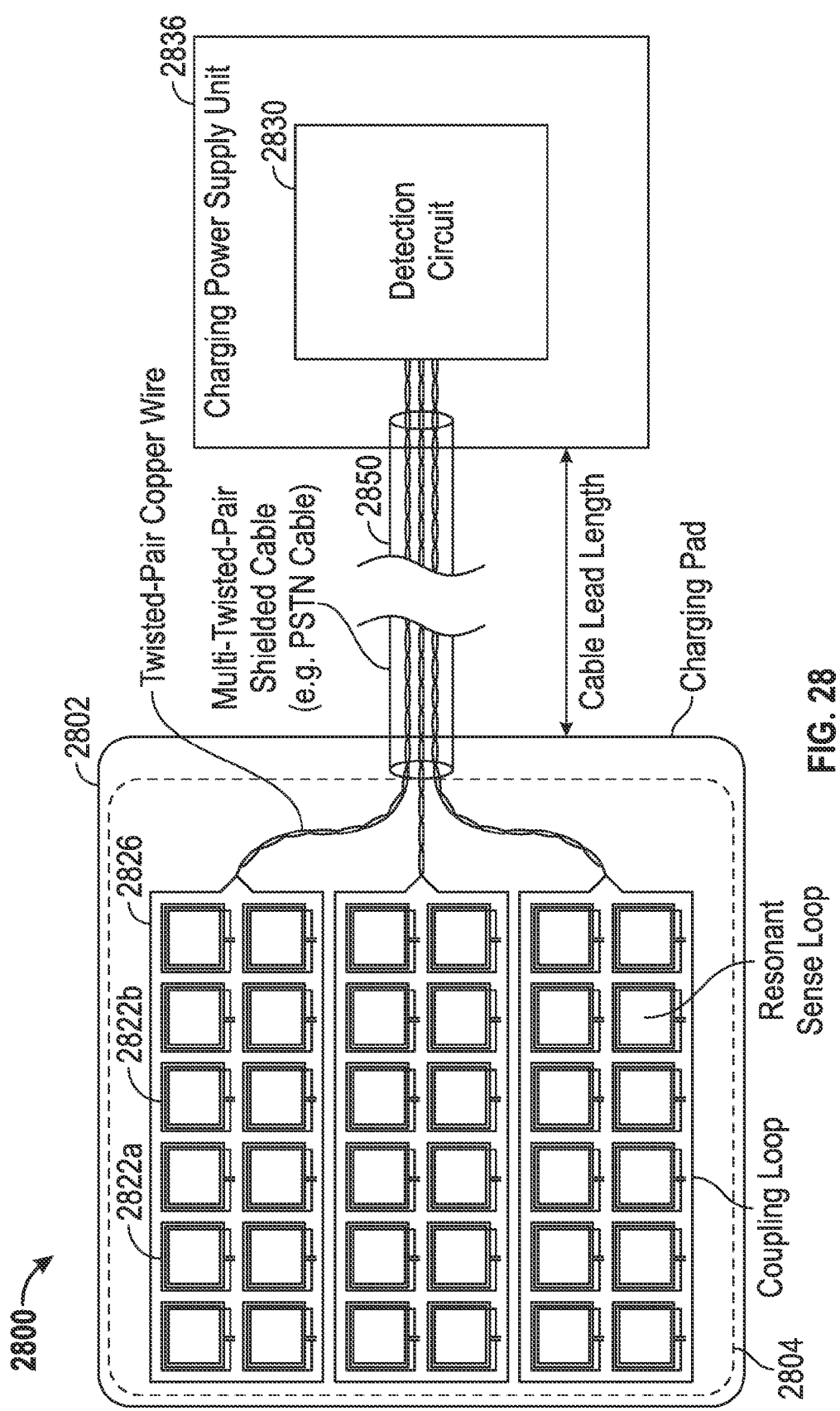
FIG. 28 is a functional block diagram of an exemplary circuit for detecting an object integrated within a inductive charging pad configured to wirelessly transmit power, in accordance with an exemplary embodiment.

FIG. 28 is a functional block diagram of an exemplary apparatus 2800 for detecting an object integrated within a inductive charging pad 2802 configured to wirelessly transmitting power, in accordance with an exemplary embodiment. The inductive charging pad 2802 includes an electrically conductive structure 2804 (e.g., an induction coil 104a as described above with reference to FIG. 1) that is configured to wirelessly transmit power via a magnetic field at a level sufficient to power or charge a load. The apparatus 2800 includes an array of sense loops 2822a, 2822b (hereinafter 2822) for detecting objects may be provided across the surface of the pad 2802. The array of sense loops 2822 may include coupling loops such as loop 2826 configured to inductively couple multiple sense loops 2822a and 2822b to a detection circuit 2830 via a lead line shown in cable 2850. The detection circuit 2830 may be integrated within a charging power supply unit 2836. As shown in FIG. 28, the multiple coupled resonant loop approach may provide solutions that integrate an entirely passive sensor network into the charging pad 2802 requiring considerable reduction of wiring complexity. A bundle of twisted pair lines e.g., a PSTN cable may be used to connect the resonant sense loop array to the multiplexer that may be part of the remotely located detection circuit 2830 (i.e., foreign object detection electronics). A non-entirely passive solution with a multiplexer on the charging pad may also be provided according to another embodiment. It is noted that the apparatus 2800 may be adapted to use any of the sense loop/coupling circuit configurations of FIGS. 14-24.

Coupled Resonator Filter

Figure 29:
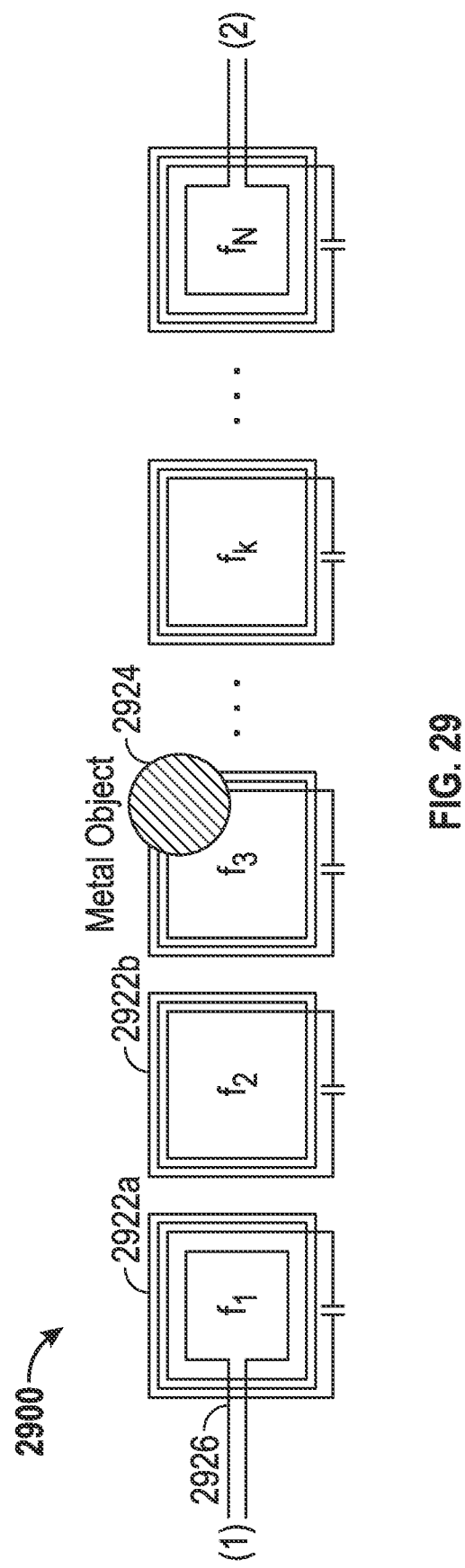
FIG. 29 is a functional block diagram of an exemplary inductively coupled resonant filter for detecting an object, in accordance with an exemplary embodiment.

Forming a propagation medium (transmission line) using canonical structures of coupled resonant loops may be another approach to metal object detection. FIG. 29 is a functional block diagram of an exemplary inductively coupled resonant filter 2900 for detecting objects, in accordance with an exemplary embodiment. FIG. 29 shows an embodiment using inductively coupled wire loops 2922a and 2922b. The circuit 2900 may be also considered as a high order filter with an inductively coupled input and output terminal 2926. Resonators may be all tuned to the same frequency or to slightly different frequencies as required for optimum sensitivity and detectability of an object.

Here, metal objects may be detected by measuring reflection characteristics at port 1 and/or port 2 and/or transmission characteristics between port 1 and port 2, which may change in presence of a metal object.

Other structures combining the multiple coupled resonant loop approach with the coupled resonator filter approach, or topologies using capacitive coupling may also be provided. Loop structures extending in two or three dimensions and defining multiple measuring ports are also possible.

Evaluation (Post-processing) Methods and Procedures

As illustrated in conceptual diagrams above, the output of a magnetic field or impedance analyzer may have to be further processed in an evaluation unit (e.g., evaluation unit 2232 of FIG. 22) of a detection circuit. With reference to FIG. 22, for example, besides subtracting reference/calibration values and making decisions, the evaluation unit 2232 may perform a modification on the measurement samples as delivered by the analyzer unit. This modification may be part of a post processing method. An example of such a modification and a method is provided above for the case of the magnetic field sensing method (least mean square method).

Similar methods may be also employed to enhance the loop impedance or loop resonant frequency sensing approach to compensate for residual effects e.g., from the vehicle pad, vehicle's underbody structure, temperature drift, dielectric objects (water, snow, ice, foliage), aging, etc.

These residual effects may be recognized in the patterns that are produced if measured values/samples are mapped onto a 2-dimensional array according to the array of loop sensors resulting in a 2-dimensional value matrix consisting of rows and columns.

By using artificial intelligence including neuronal networks, fuzzy logic, etc., such effects may be effectively compensated or cancelled out increasing detection probability and/or reducing false alarm probability of the metal object detector.

Such methods may include detecting metal objects in their context or background pattern rather than using absolute detection criteria, e.g., automatically assessing the detection threshold and detection rules based on the back ground pattern.

If the pattern appears noisy, meaning that time sequentially acquired patterns show a variance, a temporal and/or a spatial averaging technique may apply e.g., moving average, exponential decay averaging (e.g., $1^{st}$ order infinite response filter) over sequentially acquired patterns and/or spatial filtering/smoothing.

The decision threshold may be set lower e.g., for detecting sudden/abrupt and local changes in a measured pattern since such changes are unlikely to occur from temperature drift and aging or from a vehicle parking on the charging pad. This approach may provide increased sensitivity for detecting objects that enter the critical space when FOD is active.

Spatial interpolation over the array of samples e.g., over rows and columns may enhance detection particularly for small objects that are placed on corners or edges of sense loops where innate sensitivity may be lower. Using interpolation, an object positioned in the corner of four adjacent loops may provide a similar response as a coin positioned in the center of a loop.

Moreover, information from other sensors, vehicle positioning system, vehicle detection and identification system, power and efficiency measurements (power budget) on the energy transfer system may be taken into account in the pattern recognition and decision process.

Joint use of different detection techniques, methods, procedures as described above may provide solutions with enhanced detection sensitivity, reliability and/or resilience to environmental impacts. For example, the loop induced voltage may be combined with the loop impedance measuring method, or any of the inductive sensing method may be combined with at least one of an optical, acoustical, or uW sensing method.

Trouble Shooting and Recalibration Methods and Procedures

Embodiments further may provide for trouble shooting and recalibration of an object detection system.

It may happen over the years that one or more loops of a pad integrated loop array may break or modify its impedance e.g., due to mechanical or environmental impacts (damage), mechanical stress, aging or by other reasons. Impedance as measured at these loop ports in such event may be completely out of range or may mimic a foreign object that is actually not present.

Such a fault event may be detected and reported to a central management system of an infrastructure operator or to an electronic device of the user/owner of the system if installed e.g., in a home garage. Reporting may be via standard communications links as they may be available to monitor and manage a charging infrastructure.

The following trouble shooting and recalibration method may apply:
1. Request visual inspection of the charging pad by a service personnel/trouble shooter (in case of public infrastructure) or by the user/owner of a privately owned system
2. Check if the pad is clean from any metal object
3. Interrogate system to get error status info about failed loop sensors and how many loops are out of spec
4. If number of failed loops does not exceed permitted number and if failed loops do not form unacceptable clusters, recalibrate the FOD system, else initiate replacement of the pad Other pads of a charging infrastructure that do not signal faults may not need periodic recalibration and maintenance.

In contrast to implementations using inductive sensing, other types of systems may be provided in accordance with other embodiments. Microwave or Millimeter wave radar sensing for object detection is used in security systems described in Li, Yong, et. al, "A microwave measurement system for metallic object detection using swept-frequency radar", Millimetre Wave and Terahertz Sensors and Technology, Proc. of SPIE Vol. 7117 71170K-1, 2008. Ultra high frequencies e.g., in the Terrahertz range and ultra wide processing bandwidth may be used to resolve a small and thin object e.g., a coin placed on a surface. Microwave radar techniques in general may however be useful to detect small hazardous objects, which are not located on a solid surface but elsewhere in the space between the primary and secondary magnetic structure (air gap). Similarly to active acoustic sensing, electromagnetic waves are reflected or scattered by a foreign object and may be detected by a microwave sensor array that is integrated in the peripheral area of an energy transfer pad. Propagation delay may be used as a criterion to distinguish a foreign object from reflections of the ground, the adjacent magnetic pad, or the vehicle's underbody structure. However, this method may not be able to distinguish metal objects from other solid but non-hazardous objects.

In another embodiment, microwave sensing may use the vibration of metal objects as a peculiar characteristic to distinguish metal objects from non-metal objects. A metal object exposed to a strong alternating magnetic field vibrates at a frequency twice that of the magnetic field. If irradiated by a microwave source, this vibration causes a micro-phase (frequency) modulation in the reflected or scattered waves. This micro-Doppler effect may be visible as two weak responses at frequencies $$f_{1,2} = f_c \pm f_m$$

where $f_m$ denotes the magnetic field frequency and $f_c$ the microwave carrier frequency. In other words, metal objects may be detected by their characteristic signature in the Doppler frequency domain.

This microwave-Doppler-based approach may be supplemented by a magnetic pulse generator. A strong enough magnetic pulse will shake a metal object causing a more pronounced Doppler response. Such a magnetic pulse may be generated by temporarily connecting a high voltage pulse generator to the magnetic structure as used for the inductive energy transfer. A high current pulse may be generated by charging a large high voltage capacitor and discharging it directly via the pad's coil. This method may consume considerable amount of energy and may produce an EMC issue if continuously applied e.g. by periodic pulsing. However, it may serve temporarily for a relatively short period of time as a second (post detection analysis) method for substantiating a positive detection hypothesis that was obtained using a first method. The first method that is continuously running may use at least one of a method described above. This two stage approach to foreign object detection may provide improved reliability (higher detection probability and/or lower false alarm probability).

Figure 30A:
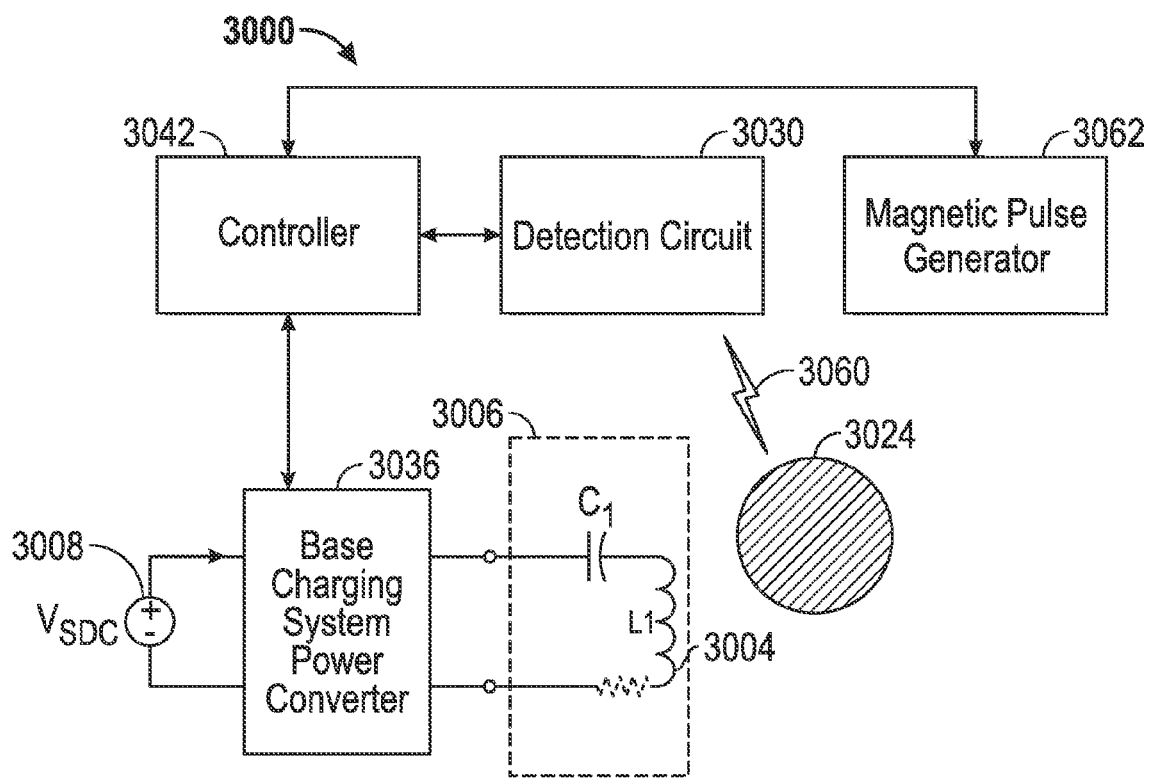
FIG. 30A is a functional block diagram of another exemplary system for detecting an object, in accordance with an exemplary embodiment.

FIG. 30A is a functional block diagram of another exemplary system 3000 for detecting an object 3024, in accordance with an exemplary embodiment. The system includes a power source 3008, a base charging system power converter 3036 and a transmit circuit 2006 including a base system induction coil 3004 as described above with reference to FIG. 2. These components may form, at least in part, a power circuit configured to generate a magnetic field and transfer power wirelessly at a level sufficient to power or charge, for example, an electric vehicle via the magnetic field. The system further includes a detection circuit 3030 configured to transmit signals and detect a frequency of vibration of an object 3024 based on a reflection of signal. For example, the detection circuit 3030 may be configured to transmit microwave signals and configured to detect a frequency of vibration based on a micro-Doppler effect as described above. For example, the detection circuit 3030 may be configured to detect an object 3024 is metal based on a particular frequency of vibration (e.g., twice the frequency of the alternating current of the power source 3008 used to generate the alternating magnetic field at the frequency). The system 3000 further includes a magnetic pulse generator 3062 configured to generate a magnetic pulse stronger than the magnetic field generated by the power circuit. This may be done in response to initially detecting an object. After the pulse is generated, the detection circuit may be configured to 3030 re-detect the frequency of vibration of an object 3024 to confirm a positive detection of a metal object 3024 based on the detected frequency.

According to this embodiment, the magnetic field generated may be leveraged to further provide a magnetic field for detection of objects. Using the existing magnetic field used for power transfer, the detection circuit 3030 may be configured to detect vibration of objects to identify metal objects.

Figure 30B:
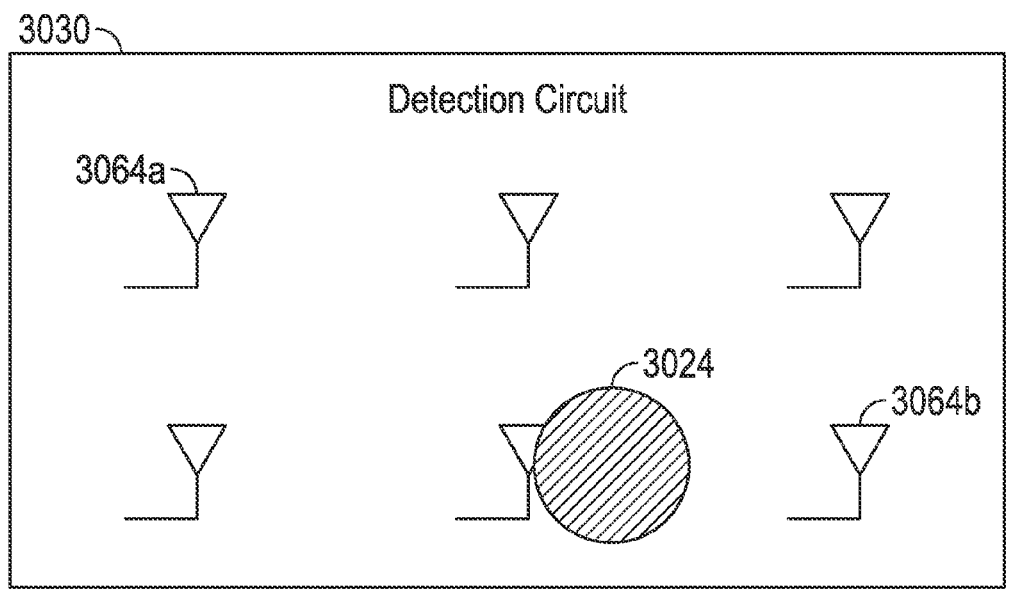
FIG. 30B is a functional block diagram of a detection circuit of the system of FIG. 30A, in accordance with an exemplary embodiment.

FIG. 30B is a functional block diagram of a detection circuit 3030 of the system of FIG. 30A, in accordance with an exemplary embodiment. As shown, the detection circuit 330 includes several sensors 3064a and 3064b that may form an array covering some area, for example corresponding to an area above a charging pad. Each of the sensors 3064a and 3064b may be configured to transmit signals and each determines a frequency of vibration of an object along with other information based on reflected signals. In this way spatial resolution may be provided allowing the detection circuit 3030 to be able to determine a type, shape, or distance of the object from the detection circuit. As such an array of sensors is provided to provide for spatial resolution to allow for detecting various characteristics of an object to be detected. In one sense, an "image" of the pad may be provided using an array of sensors. As the pad itself may vibrate from the magnetic field, the array of sensors may allow for distinguishing the pad and other objects. Stated another way, a three-dimensional "microwave" image may be provided to detect objects throughout the space between a pad and an area for detecting.

In addition, as mentioned above, the embodiments described above may be used in a variety of different applications. For example, an embodiment according to those described above may be configured to detect an absence of an object, for e.g., an anti-theft system. For example, the detection circuit and sense loops may be placed proximate an object and configured to detect if the object has been removed based on a change in an electrical characteristic of the sense loop. More particularly, as another example, the detection circuit may be configured to detect that a frequency at which a sense loop resonate changes when the object is removed. In this case the reference resonant frequency may be the frequency at which the sense loop resonates in the presence of an object.

Figure 31:
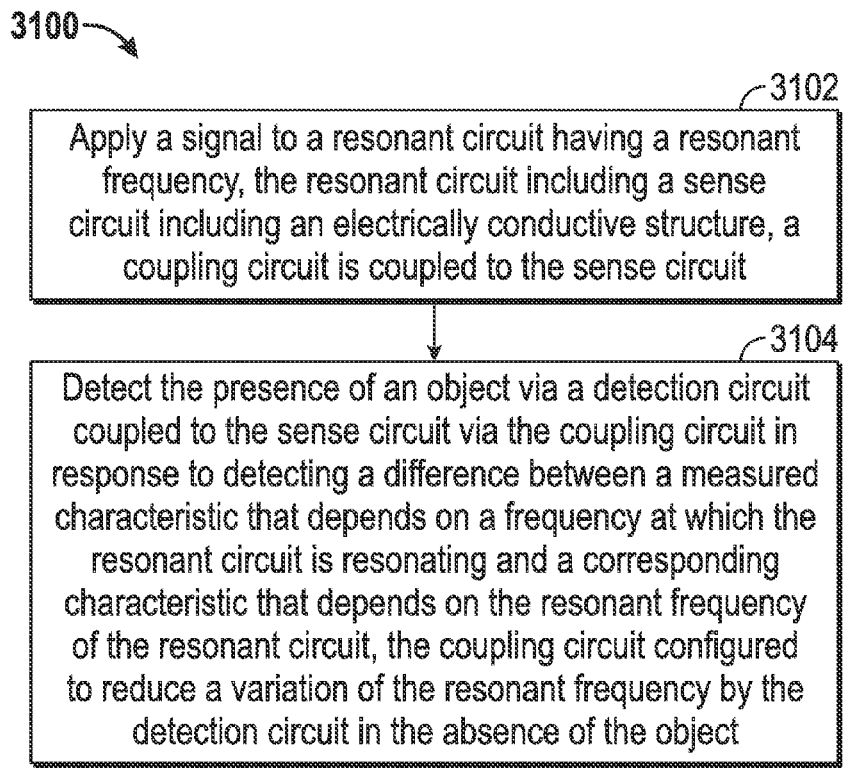
FIG. 31 is a flowchart of an exemplary method for detecting the presence of an object, in accordance with an exemplary embodiment.

FIG. 31 is a flowchart of an exemplary method 3100 for detecting the presence of an object, in accordance with an exemplary embodiment. At block 3102, a signal is applied to a resonant circuit having a resonant frequency. The resonant circuit includes a sense circuit including an electrically conductive structure. A coupling circuit is coupled to the sense circuit. At block 3104, the presence of an object is detected via a detection circuit coupled to the sense circuit via the coupling circuit in response to detecting a difference between a measured characteristic that depends on a frequency at which the resonant circuit is resonating and a corresponding characteristic that depends on the resonant frequency of the resonant circuit. The coupling circuit is configured to reduce a variation of the resonant frequency by the detection circuit in the absence of the object. In an embodiment, the method 3100 may be performed by the circuit 1400A.

Figure 32:
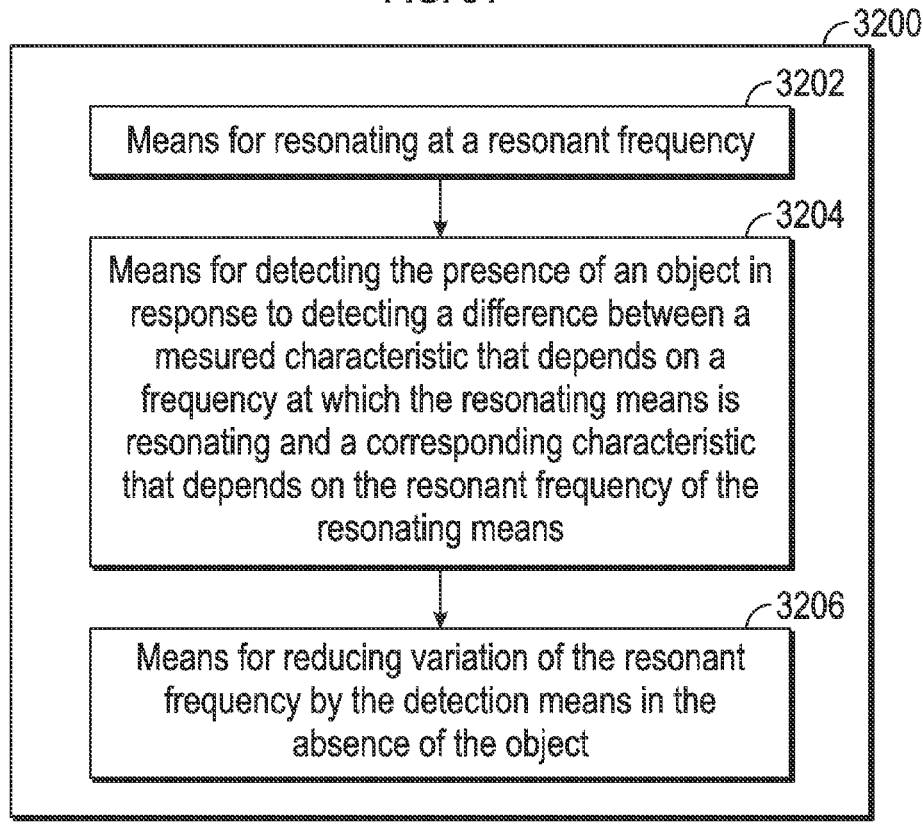
FIG. 32 is a functional block diagram of an apparatus for detecting the presence of an object, in accordance with an exemplary embodiment.

FIG. 32 is a functional block diagram of an apparatus 3200 for detecting the presence of an object, in accordance with an exemplary embodiment. The apparatus 3200 includes means 3202, 3204, and 3206 for the various actions discussed with respect to FIGS. 1-29.

Figure 33:
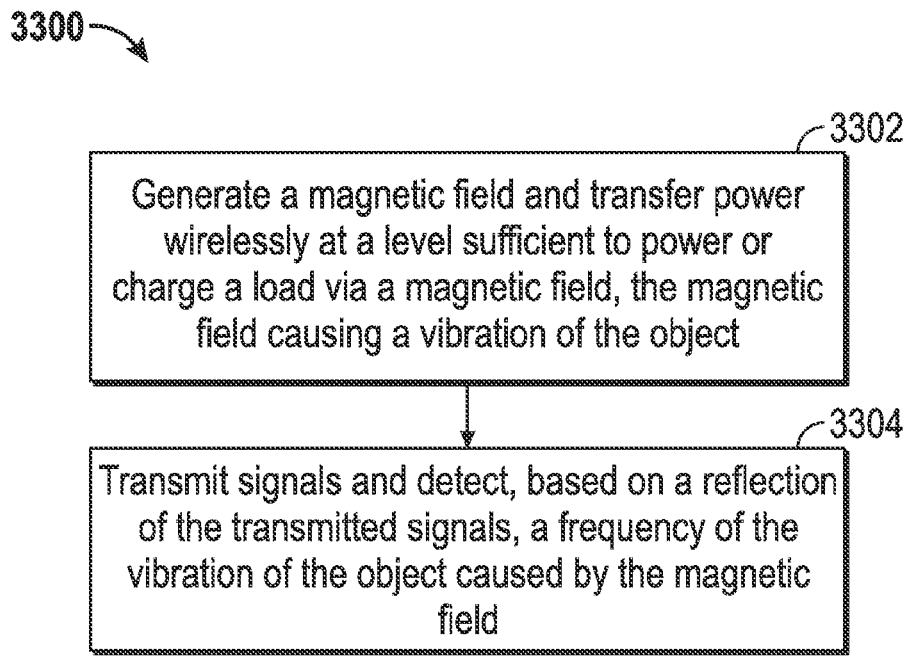
FIG. 33 is a flowchart of an exemplary method for detecting the presence of an object in a magnetic field, in accordance with an exemplary embodiment.

FIG. 33 is a flowchart of an exemplary method 3300 for detecting the presence of an object in a magnetic field, in accordance with an exemplary embodiment. At block 3302, a magnetic field is generated and power is transferred wirelessly at a level sufficient to power or charge a load via the magnetic field. The magnetic field causes a vibration of an object. At block 3304, signals are transmitted and a frequency of vibration of the object caused by the magnetic field is detected based on a reflection of the transmitted signals.

Figure 34:
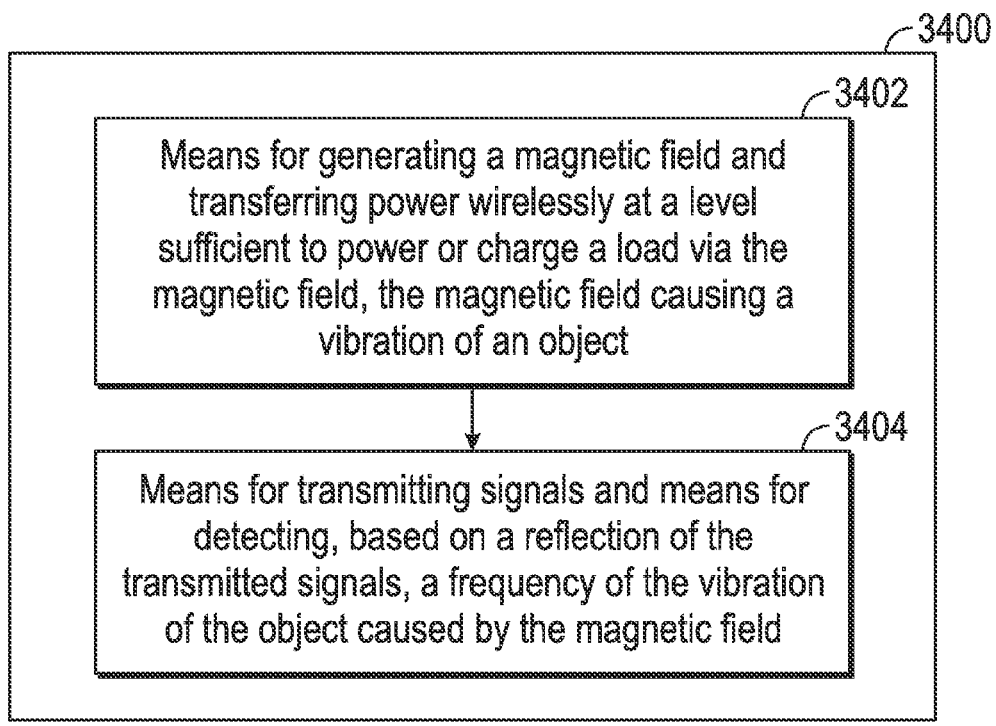
FIG. 34 is a functional block diagram of an apparatus for detecting the presence of an object in a magnetic field, in accordance with an exemplary embodiment.

FIG. 34 is a functional block diagram of an apparatus for detecting the presence of an object in a magnetic field, in accordance with an exemplary embodiment. The apparatus 3400 includes means 3402 and 3404 for the various actions discussed with respect to FIGS. 30A, 30B, and 33.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations. For example, a means for generating a magnetic field may comprise an antenna or other conductive structure. A means for resonating may comprise a resonant circuit. A means for detecting may comprise a detection circuit or other controller. A means for reducing variation of a resonant frequency may comprise a coupling circuit.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and method steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

For purposes of summarizing the disclosure, certain aspects, advantages and novel features s have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

Various modifications of the above described embodiments will be readily apparent, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An apparatus for detecting a presence of an object, the apparatus comprising:
    a plurality of resonant sense circuits, each having a resonant frequency, each resonant sense circuit comprising an electrically conductive structure and a coupling circuit configured to determine resonance and an amount of coupling, the electrically conductive structure comprising a loop positioned within a multidimensional loop array;
    a multiplexer coupled to the plurality of resonant sense circuits;
    at least one capacitor coupled between the plurality of resonant sense circuits and the multiplexer; and
    a detection circuit coupled to the multiplexer, the detection circuit configured to detect the presence of the object in response to detecting a difference between a measured characteristic that depends on a frequency at which a resonant sense circuit of the plurality of resonant sense circuits is resonating and a corresponding characteristic that depends on the resonant frequency of the resonant sense circuit.

2. The apparatus of claim 1, wherein each coupling circuit comprises one of:
    a capacitor electrically connected between the electrically conductive structure and the multiplexer, the resonant sense circuit comprising the capacitor and the electrically conductive structure;
    at least one capacitor and a coupling loop electrically connected to the multiplexer, the coupling loop inductively coupled to the electrically conductive structure; or
    a capacitive voltage divider configured to capacitively couple the multiplexer to the resonant sense circuits.

3. The apparatus of claim 2, wherein the coupling circuit is configured to reduce a variation of the resonant frequency by the multiplexer in the absence of the object, the capacitor further configured to attenuate electrical signals having frequencies lower than the resonant frequency.

4. The apparatus of claim 2, wherein each resonant sense circuit comprises an electrically conductive structure, a capacitor electrically connected to the electrically conductive structure, the electrically conductive structure comprising an inductor, and wherein the capacitor and the electrically conductive structure substantially form the resonant circuit and substantially determine the resonant frequency.

5. The apparatus of claim 2, wherein the capacitive voltage divider comprises a first capacitor and a second capacitor, wherein each resonant sense circuit comprises the first capacitor that is coupled to the electrically conductive structure that comprises an inductor, wherein the first capacitor and the electrically conductive structure substantially form the resonant circuit and substantially determine the resonant frequency, the second capacitor determining an amount of coupling between the resonant sense circuit and the detection circuit.

6. The apparatus of claim 2, wherein each resonant sense circuit comprises an electrically conductive structure, a capacitor electrically connected to the electrically conductive structure, the electrically conductive structure comprising an inductor, and wherein the capacitor and the electrically conductive structure substantially form the resonant sense circuit and substantially determine the resonant frequency, and wherein the electrically conductive structure is inductively coupled to the multiplexer, determining an amount of coupling between the resonant sense circuit and the detection circuit.

7. The apparatus of claim 1, wherein the measured characteristic comprises at least one of a measured resonant frequency or a measured quality factor (Q-factor) of the resonant circuit, and wherein the corresponding characteristic is at least one of the resonant frequency or the Q-factor of the resonant circuit.

8. The apparatus of claim 1, wherein the multiplexer comprises a lead line electrically connected to the coupling circuit, and wherein the coupling circuit is further configured to reduce a variation of the resonant frequency by the lead line in the absence of the object.

9. The apparatus of claim 1, wherein the plurality of electrically conductive structures comprise a first electrically conductive structure and a second electrically conductive structure, different from the first electrically conductive structure, the second electrically conductive structure configured to wirelessly transmit power via a magnetic field at a level sufficient to power or charge a load.

10. The apparatus of claim 9, further comprising a transmit circuit configured to apply an alternating current to the second electrically conductive structure at a frequency, wherein the resonant frequency of the resonant circuit is higher than the frequency of the alternating current.

11. The apparatus of claim 9, wherein the first electrically conductive structure comprises a first loop defining a first plane, wherein the second electrically conductive structure comprises a second loop defining a second plane substantially parallel with the first plane, wherein the first loop is positioned over at least one of an area enclosed by the second loop or overlapping the second loop.

12. The apparatus of claim 11, wherein the loops of the plurality of sense circuits positioned in the multi-dimensional loop array collectively defining a third plane, and wherein the loops collectively cover at least the area enclosed by the second loop.

13. The apparatus of claim 12, wherein a diameter of each of the loops of the plurality of resonant sense circuits is substantially equal to or less than ten percent of a diameter of the second loop.

14. The apparatus of claim 12, wherein a diameter of each of the loops of the plurality of sense circuits is substantially equal to or greater than twice a size of the object.

15. The apparatus of claim 12, wherein the detection circuit is further configured to detect the presence of the object in response to detecting a difference between respective measured characteristics that depend on frequencies at which each of the resonant sense circuits are resonating and corresponding characteristic that depend on the respective resonant frequencies.

16. The apparatus of claim 1, wherein the measured characteristic comprises a measured resonant frequency, and wherein the detection circuit is configured to measure an impedance response of the resonant sense circuit over a range of frequencies including the resonant frequency and configured to determine the measured resonant frequency based on the impedance response.

17. The apparatus of claim 1, wherein the measured characteristic comprises a measured resonant frequency, wherein the detection circuit comprises at least one of:
a swept frequency generator configured to drive the resonant circuit with a signal over a range of frequencies and stopping driving the resonant circuit when resonance is detected to determine the measured resonant frequency;
a pulse generator configured to measure a frequency response of the resonant circuit to determine the measured resonant frequency; or
a pseudo-random noise generator configured to measure the frequency response of the resonant circuit to determine the measured resonant frequency.

18. The apparatus of claim 1 wherein the resonant sense circuit is a first resonant sense circuit, wherein the resonant frequency is a first resonant frequency, wherein the coupling circuit is a first coupling circuit,
wherein the apparatus further comprises a second resonant sense circuit having a second resonant frequency comprising a second electrically conductive structure, the apparatus further comprising a second coupling circuit, the detection circuit coupled to the second resonant sense circuit via the multiplexer, and
wherein the detection circuit is configured to detect the presence of the object further in response to detecting a difference between a second measured characteristic that depends on a frequency at which the second resonant sense circuit is resonating and a corresponding second characteristic that depends on the second resonant frequency of the second resonant sense circuit, the second coupling circuit further configured to reduce variation of the second resonant frequency by the detection circuit in the absence of the object.

19. The apparatus of claim 18, wherein the first resonant frequency of the first resonant sense circuit is different than the second resonant frequency of the second resonant sense circuit.

20. The apparatus of claim 18, wherein the first and second resonant sense circuits comprise a first and a second loop, respectively, the first and second loops substantially co-planar.

21. The apparatus of claim 20, wherein the first loop at least partially overlaps the second loop.

22. The apparatus of claim 1, wherein the coupling circuit provides at least one of a weak coupling or a galvanic isolation between the resonant sense circuit and the multiplexer.

23. The apparatus of claim 1, further comprising at least one capacitor coupled between the multiplexer and the detection circuit.

24. A method for detecting a presence of an object, the method comprising:
applying a signal to a plurality of resonant sense circuits, each having a resonant frequency, each resonant sense circuit coupled to a multiplexer and comprising a respective first electrically conductive structure and a coupling circuit configured to determine resonance and an amount of coupling, the first electrically conductive structures comprising a plurality of first loops collectively defining a first plane, and wherein the plurality of resonant sense circuits and the multiplexer are coupled with at least one capacitor therebetween;
wirelessly transmitting power via a second electrically conductive structure different from the first electrically conductive structures, the power transmitted via a magnetic field at a sufficient level to power or charge a load, the second electrically conductive structure comprising a second loop defining a second plane substantially parallel with the first plane, the plurality of first loops at least overlapping an area enclosed by the second loop; and
detecting the presence of the object via a detection circuit coupled to the multiplexer in response to detecting a difference between a measured characteristic that depends on a frequency at which the resonant sense circuit is resonating and a corresponding characteristic that depends on the resonant frequency of the resonant sense circuit.

25. The method of claim 24, wherein the coupling circuit comprises one of:
a capacitor electrically connected between the electrically conductive structure and the multiplexer, the resonant sense circuit comprising the capacitor and the electrically conductive structure;
at least one capacitor and a coupling loop electrically connected to the multiplexer, the coupling loop inductively coupled to the electrically conductive structure; or
a capacitive voltage divider configured to capacitively couple the multiplexer to the resonant sense circuits.

26. The method of claim 24, wherein the multiplexer and the detection circuit are coupled with at least one capacitor therebetween.

27. An apparatus for detecting a presence of an object, the apparatus comprising:
a plurality of means for resonating at a plurality of resonant frequencies, the plurality of resonating means positioned in a multi-dimensional array;
means for determining resonance and an amount of coupling;
means for multiplexing coupled to the plurality of resonating means with at least one capacitor therebetween
means for wirelessly transmitting power via a magnetic field at a level sufficient to power or charge a load; and
means for detecting the presence of the object in response to detecting a difference between a measured characteristic that depends on frequencies at which each of the plurality of resonating means is resonating and a corresponding characteristic that depends on the resonant frequencies of each the plurality of resonating means.

28. The apparatus of claim 27, wherein the determining means comprises one of:
a capacitor electrically connected between the resonating means and the multiplexing means, the resonating means comprising the capacitor;
at least one capacitor and a coupling loop electrically connected to the multiplexing means, the coupling loop inductively coupled to the resonating means; or
a capacitive voltage divider configured to capacitively couple the multiplexing means to the resonating means.

29. An apparatus for detecting a presence of an object, the apparatus comprising:
a plurality of sense circuits comprising respective electrically conductive structures, the plurality of sense circuits including at least a first sense circuit and a second sense circuit, the first sense circuit comprising a first electrically conductive structure and forming a first resonant circuit having a first resonant frequency, and the second sense circuit comprising a second electrically conductive structure and forming a second resonant circuit having a second resonant frequency different than the first resonant frequency;
wherein the respective electrically conductive structures each form respective loops, the loops positioned in a multi-dimensional array defining a first plane;
a detection circuit coupled to the first and second sense circuits, the detection circuit configured to detect the presence of the object in response to detecting:
a difference between a first measured characteristic that depends on a frequency at which the first resonant circuit is resonating and a first corresponding characteristic that depends on the first resonant frequency, or
a difference between a second measured characteristic that depends on a frequency at which the second resonant circuit is resonating and a second corresponding characteristic that depends on the second resonant frequency; and
a coupling circuit coupled between the first and second sense circuits and the detection circuit, the coupling circuit configured to reduce variation of the first and second resonant frequencies by the detection circuit in the absence of the object,
wherein the first and second sense circuits further comprise a first and second capacitor, respectively, the first and second capacitors each having values tuned to determine the first and second resonant frequencies, respectively, wherein the coupling circuit comprises a third capacitor coupled between the detection circuit and the first and second sense circuits, at least the third capacitor and the first capacitor forming a capacitive voltage divider.

30. The apparatus of claim 29, wherein the detection circuit is further configured detect a position of the object relative to at least one of the first and second electrically conductive structures in response to the detecting.

31. The apparatus of claim 29, wherein the first and second sense circuits each comprise a capacitor having a value tuned to determine the first and second resonant frequencies, respectively.

32. The apparatus of claim 29, wherein the coupling circuit comprises:
a coupling loop electrically connected the detection circuit, the coupling loop inductively coupled to the first and second sense circuits, the first and second sense circuits substantially alone forming the first and second resonant frequencies, respectively.

33. The apparatus of claim 29, wherein the first and second sense circuits comprise a first and second capacitor, respectively, the first and second capacitors each having values tuned to determine the first and second resonant frequencies, respectively, wherein the coupling circuit comprises a third capacitor coupled between the detection circuit and the first sense circuit and a fourth capacitor coupled between the detection circuit and the second sense circuit, the third capacitor and the first capacitor forming a first capacitive voltage divider, and the fourth capacitor and the first capacitor forming a second capacitive voltage divider.

34. The apparatus of claim 29, wherein the apparatus further comprises a third electrically conductive structure, different from the first and second electrically conductive structures, the third electrically conductive structure configured to wirelessly transmit power via a magnetic field at a level sufficient to power or charge a load.

35. The apparatus of claim 34, wherein the first plane is substantially parallel with a second plane defined by the third electrically conductive structure, wherein the loops collectively cover at least an area covered by the third electrically conductive structure.

36. The apparatus of claim 35, wherein at least each of the plurality of sense circuits form respective resonant circuits having respective resonant frequencies, wherein the detection circuit is configured detect the presence of the object in response to detecting a difference between respective measured characteristics that depend on frequencies at which the respective resonant circuits are resonating and respective corresponding characteristics that depend on the respective resonant frequencies.

37. The apparatus of claim 29, wherein the first and second measured characteristics are at least one of first and second measured resonant frequencies or first and second measured quality factors (Q-factor) of the first and second resonant circuits.

38. The apparatus of claim 29, wherein the first and second electrically conductive structure comprise first and second loops, respectively, a diameter of each of the first and second loops substantially equal to or less than twice a size of the object.

39. An apparatus for detecting a presence of an object, the apparatus comprising:
  a plurality of resonant sense circuits, each having a resonant frequency, each resonant sense circuit comprising an electrically conductive structure and a coupling circuit configured to determine resonance and an amount of coupling, the electrically conductive structure comprising a loop positioned within a multidimensional loop array;
  a multiplexer coupled to the plurality of resonant sense circuits; and
  a detection circuit coupled to the multiplexer, the detection circuit configured to detect the presence of the object in response to detecting a difference between a measured characteristic that depends on a frequency at which a resonant sense circuit of the plurality of resonant sense circuits is resonating and a corresponding characteristic that depends on the resonant frequency of the resonant sense circuit at least one capacitor coupled between the multiplexer and the detection circuit.

* * * * *